United States Patent
Lin et al.

(10) Patent No.: US 7,365,211 B2
(45) Date of Patent: Apr. 29, 2008

(54) HETEROCYCLIC GABAA SUBTYPE SELECTIVE RECEPTOR MODULATORS

(75) Inventors: Xao-Fa Lin, Palo Alto, CA (US); David Garrett Loughhead, Belmont, CA (US); Sanja Novakovic, San Jose, CA (US); Counde O'Yang, Sunnyvale, CA (US); Michael Soth, Milpitas, CA (US); David George Putman, Stow, MA (US)

(73) Assignee: Roche Palo Alto LLC, Palo Alto, CA (US)

( * ) Notice: Subject to any disclaimer, the term of this patent is extended or adjusted under 35 U.S.C. 154(b) by 463 days.

(21) Appl. No.: 10/916,073

(22) Filed: Aug. 11, 2004

(65) Prior Publication Data

US 2005/0101614 A1    May 12, 2005

Related U.S. Application Data

(60) Provisional application No. 60/574,384, filed on May 25, 2004, provisional application No. 60/495,179, filed on Aug. 14, 2003.

(51) Int. Cl.
*C07D 231/54* (2006.01)
*C07D 231/56* (2006.01)

(52) U.S. Cl. .................. 548/360.1; 548/360.5; 548/361.1; 548/361.5; 548/362.1; 548/362.5

(58) Field of Classification Search ............ 548/360.1, 548/360.5, 361.1, 361.5, 362.1, 362.5
See application file for complete search history.

(56) References Cited

U.S. PATENT DOCUMENTS

| | | |
|---|---|---|
| 6,399,608 B1 | 6/2002 | Dawson |
| 2002/0119972 A1 | 8/2002 | Leftheris |
| 2004/0110815 A1 | 6/2004 | Cournoyer |

FOREIGN PATENT DOCUMENTS

| | | |
|---|---|---|
| WO | WO 01/77111 A1 | 10/2001 |
| WO | WO 02/16348 A1 | 2/2002 |
| WO | WO 02/20492 A1 | 3/2002 |
| WO | WO 2004/050634 A1 | 6/2004 |

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Cooke & N. M. Hamilton, "α-Subunit selective modulators of GABAA receptor function as CNS tyherapeutics," Exp. Opin. Ther. Patents 2002 12(10):1491-1501.
M. Chebib & G.A.R. Johnston, "GABA-Activated Ligand Gated Ion Channels: Medicinal Chemistry and Molecular Biology," J. Med. Chem. 2000 43(8):1427-1447.
Shawali, A.S., "Synthesis and Tautomeric Structure of some 2*H*-Pyrazolo[3,4-*d*] pyradazines", *J. of Heterocyclic Chem.*, 1977, 14(3):375-81.

* cited by examiner

*Primary Examiner*—Janet L. Andres
*Assistant Examiner*—Raymond Covington
(74) *Attorney, Agent, or Firm*—Brian L. Buckwalter

(57) ABSTRACT

This invention relates to a method for modulating $\alpha_2$ subtype $GABA_A$ receptors with heterocyclic compounds of formula I, and salts, solvates and prodrugs thereof. The invention further relates to said heterocyclic compounds and pharmaceutical compositions containing said compounds. In addition the invention relates to the treatment of depression, an anxiety disorder, a psychiatric disorder, a learning or cognitive disorder, a sleep disorder, a convulsive or seizure disorder or pain

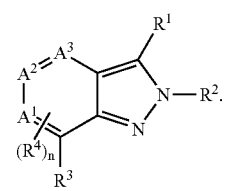

(I)

5 Claims, No Drawings

HETEROCYCLIC GABAA SUBTYPE SELECTIVE RECEPTOR MODULATORS

CROSS REFERENCE TO PRIOR APPLICATIONS

This application claims benefit under Title 35 U.S.C. 119(e) of U.S. Provisional Application Nos. 60/495,179, filed Aug. 14, 2003 and 60/574,384, filed May 25, 2004, which are hereby incorporated by reference in their entirety.

FIELD OF THE INVENTION

This invention relates to a method for modulating $\alpha_2$ subtype $GABA_A$ receptors and method for treating a subject afflicted with a disease alleviated by modulating $GABA_A$ receptors with heterocyclic compounds, more particularly, to substituted 7-arylindazole, 7-aryl-2H-pyrazolo[3,4-c]pyridine, 7-aryl-2H-pyrazolo[4,3-c]pyridine and 7-aryl-2H-pyrazolo[4,3-b]pyridine compounds and salts thereof. The invention further relates to novel heterocyclic compounds and pharmaceutical compositions containing said compounds.

BACKGROUND

GABA, 4-aminobutyric acid, is the primary inhibitory transmitter in the brain and maintains a balance between excitation and inhibition of neurons. Three major classes of GABA receptors have been identified: $GABA_A$, $GABA_B$ and $GABA_C$ receptors. $GABA_A$ and $GABA_C$ receptors are ligand-gated ion channels (LGIC), while $GABA_B$ receptors are G-protein coupled receptors. The LGIC receptors are heteropentamers comprised of $\alpha_{1-6}$, $\beta_{1-3}$, $\gamma_{1-3}$, $\rho_{1-3}$, $\delta$, $\epsilon$, $\pi$, and $\theta$ subunits. Each subunit contains four membrane-spanning domains. The N-terminal domain and C-domain are extracellular and the agonist/antagonist binding site is situated on the N-terminus. There is an intracellular loop between the $3^{rd}$ and $4^{th}$ membrane spanning regions (M. Chabib and G. A. R. Johnston, *J. Med. Chem.* 2000 43(8): 1427-1447).

While studies are continuing to define the composition and anatomical distribution of GABA LGIC receptors, it is known that the dominant motif is $2\alpha 2\beta_1\gamma$ with varying $\alpha$ subtypes. Subtype assemblies containing an $\alpha_1$ subunit are present in most areas of the brain and are thought to account for over 40% of $GABA_A$ receptors in the rat. Subtype assemblies containing $\alpha_2\beta_{2/3}\gamma_2$ and $\alpha_3\beta_n\gamma_{2/3}$ oligomers are thought to account for about 18% and 17% respectively of $GABA_A$ receptors in the rat (R. M. McKeman et al. *Trend Neurosci* 1996 19:139-143). Subtype assemblies containing an $\alpha_5$ subunit are expressed predominantly in the hippocampus and cortex and are thought to represent about 4% of $GABA_A$ receptors in the rat. The most common receptor subtype assemblies appear to be the $\alpha_1\beta_2\gamma_2$, $\alpha_2\beta_3\gamma_2$, $\alpha_3\beta_3\gamma_2$ and $\alpha_5\beta_3\gamma_2$ assemblies (H. Mohler et al. *Neuroch. Res.* 1995 20(5):631-636).

All known $GABA_A$ receptors contain a plurality of distinct modulatory sites, one of which is the benzodiazepine (BZ) binding site. Other modulatory sites include allosteric sites for picrotoxin, barbiturates, neuroactive steroids and ethanol. The BZ binding site is the most explored of the $GABA_A$ receptor modulatory sites, and is the site through which anxiolytic drugs such as diazepam exert their effect. Early radioligand binding studies suggested the existence of two distinct benzodiazepine-binding sites: BZ1 and BZ2.

The BZ1 subtype has been shown to be pharmacologically equivalent to a $GABA_A$ receptor comprising the $\alpha_1$ subunit in combination with a $\beta$ subunit and $\gamma_2$. This is the most abundant $GABA_A$ receptor subtype. Two other major populations are the $\alpha_2\beta\gamma_2$ and $\alpha_3\beta_{2/3}\gamma_2$ subtypes. Together these constitute approximately a further 35% of the total $GABA_A$ receptor repertoire. Pharmacologically, the $\alpha_2\beta\gamma_2$ and $\alpha_3\beta_{2/3}\gamma_2$ subtypes appear to be equivalent to the BZ2 subtype. The physiological role of these subtypes has hitherto been unclear because sufficiently selective agonists or antagonists were unknown.

The barbiturates and benzodiazepines were among the first clinically useful modulators of the GABA receptors and are among the most widely prescribed medications for anxiety, depression and other psychiatric disorders and as anticonvulsants. Benzodiazepines, with relatively mild side effects, afforded an alternative to barbiturates which possess more potent side effects. Unfortunately, many of the early benzodiazepines had relative limited subtype selectivity resulting in sedation, dependence, cognitive impairment, ataxia, potentiation of ethanol effects, tolerance and withdrawal.

The advances in genetics and molecular biology have afforded more subtle probes of receptor subtype selectivity and hold out the promise of more selective agents. Receptors containing the $\alpha_1$, $\alpha_2$, $\alpha_3$ or $\alpha_5$ subunit have been classified as diazepam sensitive receptors while $\alpha_4$, or $\alpha_6$, are classified as diazepam insensitive receptors. In particular, the $\alpha_1$ subtype has been associated with sedation and $\alpha_1$ selective ligands have potential as sedatives (R. M. McKernan et al. *Nature Neurosci.* 2000 3(6): 587-592). Hypnotic/sedative compounds with preferential binding for the $\alpha_1$ subtype have been identified (D. J. Sanger and H. Depoortere, *CNS Drug Reviews,* 1998 47(5):323-340). Sedation, however, is undesirable in an anxiolytic agent.

Compounds that selectively bind to the benzodiazepine site, or to other allosteric sites, and enhance the ability of GABA to open $GABA_A$ receptor channels are agonists (or positive allosteric modulators) of GABA receptors. Compounds that interact with allosteric sites but negatively modulate the action of GABA are called inverse agonists (negative allosteric modulators). Inverse agonists diminish the ability of GABA to open receptor channels. A third class of compounds that bind selectively to the benzodiazepine site and yet have little or no effect on GABA activity, but can block the action of $GABA_A$ receptor agonists or inverse agonists that act at this site are referred to as antagonists. Agonists that act at the benzodiazepine site exhibit anxiolytic, sedative, and hypnotic effects, while compounds that act as inverse agonists at this site elicit anxiogenic, cognition enhancing, and proconvulsant effects.

The $\alpha_1$ selective $GABA_A$ receptor agonists alpidem and zolpidem are clinically prescribed as hypnotic agents, further suggesting that at least some of the sedation associated with known anxiolytic drugs is mediated through $GABA_A$ receptors containing the $\alpha_1$ subunit. Accordingly, $GABA_A$ receptor agonists which interact more selectively with the $\alpha_2$ and/or the $\alpha_3$ subunit relative to the $\alpha_1$ subunit should retain anxiolytic activity with a reduced propensity to cause sedation. Also, agents which are antagonists or inverse agonists at the $\alpha_1$ subtype might antagonize sedation or hypnosis caused by $\alpha_1$ modulators.

Selective $\alpha_2$ and $\alpha_3$ ligands have been more difficult to identify and cross-reactivity between these receptors is common. Compounds with ten to one hundred-fold selectivity for $\alpha_{2/3}$ relative to $\alpha_1$ have been reported (see, e.g., W. R. Carling et al., WO 0044752). Experiments with point mutated mice lines suggest that the α$_2$, not the α$_3$, subtype is responsible for the anxiolytic activity (U. Rudolph et al. *Trends Pharmacol. Sci.* 2001 22(4):188-194; K. Löw et al. *Science* 2000 290:131-134); however, α$_3$-selective inverse agonists appear to be anxiogenic and proconvulsant (I. J. Collins et al. WO 9855480). Since α$_2$ and perhaps α$_3$ and α$_5$ selective ligands have the potential to modulate the (BZ2) site without activating the hypnotic sedative site (BZ1) they could afford a new class of non-sedating anxiolytics. Other non-BZ selective α$_2$ GABA modulators may also exhibit anxiolytic properties without many of unwanted effects.

The α$_5$ subtype is located predominantly in the hippocampus and thought to be associated with learning and cognition. Approximately 20% of the hippocampal GABA receptors contain the α$_5$ subtype. The hippocampus is the region of the brain associated with learning and memory. Inverse α$_5$ agonists improve memory and cognition in animal behavioral models; however, their use is limited by the anxiogenic and convulsant effects of non selective compounds. Selective α$_5$ inverse agonists are potentially useful in the treatment Alzheimer's disease and related dementias (M. S. Chambers et al., *J. Med. Chem.* 2003 46(11):2227-40).

The selective ligands for GABA$_A$ receptors of the present invention are useful in the treatment and/or prevention of anxiety disorders, such as panic disorder with or without agoraphobia, agoraphobia without history of panic disorder, phobias including social phobias, obsessive-compulsive disorder, stress disorders including post-traumatic and acute stress disorder, and generalized or substance-induced anxiety disorder; depression or bipolar disorders such as single-episode or recurrent major depressive disorder, dysthymic disorder, bipolar I and bipolar II manic disorders; schizophrenia; learning and cognitive disorder such as Alzheimer's disease and attention deficit hyperactivity disorder; sleep disorders and disorders of circadian rhythm, e.g. in subjects suffering from the effects of jet lag or shift work; convulsive or seizure disorders such as epilepsy and pain.

Other neurotransmitter systems have been explored and drugs modulating serotonergic neurotransmission have been shown promise in the treatment of anxiety related disorders. Recently, drugs such as buspirone, a partial agonist at 5HT1A receptor, and serotonin reuptake inhibitors, commonly used as antidepressants, have been introduced. GABA$_A$ selective ligands may potentiate the effects of certain other CNS active compounds. There is evidence that selective serotonin reuptake inhibitors (SSRIs) show greater antidepressant activity when used in combination with GABA$_A$ selective ligands than when used alone.

Some indazoles of the present invention have been disclosed to be antagonists of the Corticotropin Releasing Factor receptor in U.S. Ser. No. 60/430,168 filed Dec. 2, 2002 and U.S. Ser. No. 10/724,971 filed Dec. 1, 2003 both of which are herein incorporated by reference in its entirety.

SUMMARY OF THE INVENTION

The present invention is directed toward pharmaceutical compositions and toward methods of preventing or treating a disorder alleviated by a positive allosteric modulator of a GABA$_A$ receptor which selectively modulates the α$_2$ subtype in presence of the α$_1$ subtype, comprising administering an effective amount of a compound according to formula I wherein:

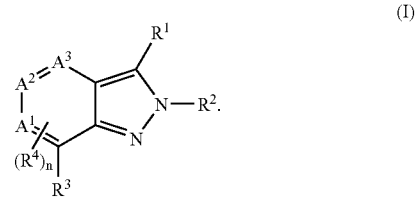

(I)

$R^1$ is —$NR^aR^b$, —$CR^cR^dR^e$, $CHR^fR^g$, $CO_2R^a$, —C(O)$NR^aR^b$, hydrogen, $C_{2-10}$ alkynyl, $C_{1-6}$ haloalkyl, cycloalkenyl, halogen, cyano, —C(=Z)R$^o$, —X$^2$C(=O)X$^1$R$^f$, NR$^f$SO$_2$R$^o$, —N[C(=O)OR$^m$]$_2$, —N=CR$^j$NR$^j$R$^k$, —S(O)$_m$R$^h$, CONR$^i$NHR$^o$, aryl, heteroaryl, where each aryl or heteroaryl is optionally substituted with one or more substituents independently selected from $C_{1-6}$ alkyl, $C_{1-6}$ alkoxy, $C_{1-16}$ alkylthio, $C_{1-6}$ alkylsulfonyl, halogen, haloalkyl, cyano, nitro, —C(O)NR$^{a'}$R$^{b'}$, and —NR$^{a'}$R$^{b'}$, where R$^{a'}$ and R$^{b'}$ are each independently selected from the group consisting of hydrogen, $C_{1-9}$ alkyl, and $C_{1-9}$ alkylcarbonyl or $R^1$ is $C_{1-10}$ alkyl wherein 2 or 3 nonadjacent carbon atoms in the alkyl chain can be replaced with —O—, —S— or —NR$^f$;

$R^2$ is hydrogen, $C_{1-6}$ alkyl, $C_{1-6}$ haloalkyl; $C_{3-6}$ cycloalkyl, $C_{3-6}$ cycloalkyl-$C_{1-3}$ alkyl, $C_{1-3}$ alkoxycarbonyl-$C_{1-3}$ alkyl; $C_{1-6}$ alkylcarbonyl, $C_{1-6}$ alkylsulfonyl, aryl, or arylalkyl, wherein said aryl or arylalkyl is optionally substituted with one or more substituents independently selected from $C_{1-6}$ alkyl, haloalkyl, $C_{1-6}$ alkoxy, and halogen;

$R^3$ is aryl or heteroaryl, each optionally substituted with one or more substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —NR$^{a''}$R$^{b''}$, where R$^{a''}$ and R$^{b''}$ are each independently selected from the group consisting of hydrogen, $C_{1-9}$ alkyl, and $C_{1-9}$ alkylcarbonyl;

$R^4$ is $C_{1-10}$ alkyl, $C_{1-10}$ alkoxy, $C_{1-6}$ haloalkyl, cyano, nitro, halogen, —NR$^{a''}$R$^{b''}$, and aryl optionally substituted with $C_{1-6}$ alkyl, $C_{1-6}$ alkoxy, $C_{1-6}$ alkylthio, $C_{1-6}$ alkyl-S(O)$_m$— (where m is 0 to 2), aminosulfonyl, monoalkylaminosulfonyl, dialkylaminosulfonyl, halogen, haloalkyl, cyano, nitro, and —NR$^{a''}$R$^{b''}$ where R$^{a''}$ and R$_{b''}$ are each independently selected from the group consisting of hydrogen, $C_{1-9}$ alkyl, and $C_{1-9}$ alkylcarbonyl;

$R^a$ and $R^b$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenylalkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or, $R^a$ and $R^b$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

$R^c$ is hydrogen, hydroxy, $C_{1-6}$ alkoxy, or $-NR^{a'''}R^{b'''}$;

$R^d$ and $R^e$ are each independently selected from the group consisting of hydrogen, $C_{1-9}$ alkyl, hydroxyalkyl, $C_{1-6}$ alkoxyalkyl, $C_{1-6}$ alkylthioalkyl, heteroalkyl, heterocyclyl, heterocyclylalkyl, $C_{3-6}$ cycloalkyl, $C_{3-6}$ cycloalkyl-$C_{1-3}$ alkyl, di-$C_{3-6}$ cycloalkyl-$C_{1-3}$ alkyl, aryl, arylalkyl, heteroaryl, heteroarylalkyl, phenylalkyl, diphenyl-$C_{1-3}$ alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, and halogen; or, $R^c$ and $R^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl, $C_{3-6}$ cycloalkyl-$C_{1-3}$ alkyl-alkylidenyl, $C_{3-6}$ heterocyclylidenyl, $C_{3-6}$ heterocyclyl-$C_{1-3}$ alkylidenyl, $C_{3-6}$ heterocyclylalkyl-$C_{1-3}$ alkylidenyl, aryl-$C_{1-3}$ alkylidenyl, aryl-$C_{1-3}$ alkyl-alkylidenyl, heteroaryl-$C_{1-3}$ alkylidenyl, and heteroarylalkyl-$C_{1-3}$ alkylidenyl, wherein each of said cycloalkyl, aryl, or heteroaryl groups is optionally substituted with one or more substituents independently selected from $C_{1-6}$ alkyl, haloalkyl, $C_{1-6}$ alkoxy, amino, alkylamino, dialkylamino, and halogen; or, $R^d$ and $R^e$ are taken together with the carbon to which they are attached to form a cycloalkyl or heterocyclyl ring;

$R^f$ is hydrogen or $C_{1-10}$ alkyl;

$R^g$ is $C_{2-10}$ alkenyl, $-NHNH_2$, cyano, $-OC(=O)R^f$, $S(O)_mR^h$ or $-X^2(C=O)X^1R^f$;

$R^h$ is $C_{1-6}$ alkyl $C_{1-6}$ heteroalkyl, $C_{2-6}$ alkenyl, $NR^jR^k$ or phenyl optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen;

$R^i$ is $R^o$, hydrogen, $C_{3-6}$ cycloalkyl or $C_{3-6}$ cycloalkyl-$C_{1-3}$ alkyl;

$R^j$ and $R^k$ are (i) independently hydrogen, $C_{1-6}$ alkyl, $C_{1-6}$ heteroalkyl, or (ii) taken together along with the nitrogen atom to which they are attached are $C_{4-6}$ alkylene or $(CH_2)_2X^1(CH_2)_2$;

$R^m$ is $C_{1-10}$ alkyl;

$R^o$ is $C_{1-6}$ alkyl, $C_{2-6}$ alkenyl or phenyl optionally substituted with one or more substituents independently selected from the group consisting of $C_{1-6}$ alkyl, haloalkyl, $C_{1-6}$ alkoxy, amino, $C_{1-6}$ alkylamino, $C_{1-6}$ dialkylamino, hydroxyalkyl, cyano, acylamino, alkylsulfonyl, alkylsulfonyloxy, and halogen;

$X^1$ and $X^2$ are independently $-O-$ or $-NR^{f1}-$ wherein at each occurrence $R^{f1}$ is an independently selected $R^f$ radical or if $R^f$ and $R^{f1}$ are attached to the same nitrogen atom, $R^f$ and $R^{f1}$ can, in addition, be taken together as $C_{4-6}$ alkylene or $(CH_2)_2X^1(CH_2)_2$;

Z is O or $NOR^o$;

m is an integer from 0 to 2;

n is an integer from 0 to p, where p=3 minus the number of A1, A2 and A3 which are nitrogen;

$R^{a'''}$ and $R^{b'''}$ are each independently selected from the group consisting of hydrogen, $C_{1-9}$ alkyl, hydroxyalkyl, $C_{1-6}$ alkoxyalkyl, $C_{1-6}$ alkylthioalkyl, carboxyalkyl, acyl, $C_{3-6}$ cycloalkyl, $C_{3-6}$ cycloalkyl-$C_{1-3}$ alkyl, di-$C_{3-6}$ cycloalkyl-$C_{1-3}$ alkyl, $C_{1-6}$ heteroalkyl, aminoalkyl, aminocarbonylalkyl, cyanoalkyl, $C_{5-8}$ heterocyclyl, heterocyclylalkyl, aryl, arylalkyl, heteroaryl, heteroarylalkyl, phenylalkyl, diphenyl-$C_{1-3}$ alkyl, and $C_{1-3}$ alkyl substituted with both a $C_{3-6}$ cycloalkyl and a phenyl group, wherein each of said cycloalkyl, phenyl, aryl, or heteroaryl groups is optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen, and each of said amino groups is optionally monosubstituted or disubstituted with alkyl; or, $R^{a'''}$ and $R^{b'''}$ are taken together with the nitrogen to which they are attached form an heterocyclyl or heteroaryl ring selected from the group consisting of pyrrolidine, piperidine, homopiperidine, tetrahydropyridine, 1,2,3,4-tetrahydroquinoline, 1,2,3,4-tetrahydroisoquinoline, tetrahydropyrimidine, hexahydropyrimidine, pyrazolidine, piperazine, morpholine, imidazoline, pyrrole, pyrazole, and imidazole, where each of said rings is optionally substituted with one or more substituents selected from the group consisting of hydroxy, oxo, alkyl, hydroxyalkyl, alkoxy, alkoxyalkyl, aminoalkyl, acyl, acylamino, aminocarbonyl, aminocarbonylalkyl, aminocarbonylamino, aminosulfonyl, alkylsulfonylamino, aminosulfonylamino, and phenyl, wherein each of said phenyl groups is optionally substituted with one or more groups independently selected from $C_{1-6}$ alkyl, haloalkyl, $C_{1-6}$ alkoxy, amino, alkylamino, dialkylamino, and halogen, and each of said amino groups is optionally monosubstituted or disubstituted with alkyl, or is contained in a pyrrolidinyl, piperidinyl, morpholinyl, or piperazinyl group;

$A^1$, $A^2$ and $A^3$ are independently C or N with the proviso that at least one of $A^1$, $A^2$ and $A^3$ is CH or $CR^4$; and, individual isomers, racemic or non-racemic mixtures of isomers, solvates hydrates, prodrugs or pharmaceutically acceptable salts thereof.

The present invention also is directed at novel compounds according to formula I which are useful in preventing or treating a disorder alleviated by a positive allosteric modulator of a $GABA_A$ receptor comprising administering an effective amount of a compound according to formula I.

DETAILED DESCRIPTION OF THE INVENTION

In one embodiment of the present invention there is provided compounds useful for preventing or treating disorders alleviated by administering a positive allosteric modulator of the $GABA_A$ receptor said compound comprising a compound according to formula I wherein $R^1$ is $CHR^fR^g$, $C_{2-10}$ alkynyl, $C_{1-6}$ haloalkyl, halogen, cyano, —C(=Z)R$^o$, —X$^2$C(=O)X$^1$R$^f$, NR$^f$SO$_2$R$^o$, —N[C(=O)OR$^m$]$_2$, —N=CR$^j$NR$^j$R$^k$, —S(O)$_m$R$^h$, CONR$^i$NHR$^o$ or $C_{1-10}$ alkyl wherein 2 or 3 nonadjacent carbon atoms in the alkyl chain can be replaced with —O—, —S— or —NR$^f$; $R^2$ is hydrogen, $C_{1-6}$ alkyl, $C_{3-6}$ cycloalkyl, $C_{3-6}$ cycloalkyl-$C_{1-3}$ alkyl, $C_{1-3}$ alkoxycarbonyl-$C_{1-3}$ alkyl, $C_{1-6}$ haloalkyl, or aralkyl; and, $R^3$, $R^4$, $R^{a''}$, $R^{b''}$, $R^f$, $R^{f1}$, $R^g$, $R^h$, $R^i$, $R^j$, $R^k$, $R^m$, $R^o$, $X^1$, $X^2$, $Z$, $A^1$, $A^2$, $A^3$, m, n are as defined hereinabove.

In another embodiment of the present invention there is provided compounds useful for preventing or treating disorders alleviated by administering a positive allosteric modulator of the $GABA_A$ receptor said compound comprising a compound according to formula I wherein $R^1$ is $CHR^fR^g$, $C_{2-10}$ alkynyl, $C_{1-6}$ haloalkyl, halogen, cyano, —C(=Z)R$^o$, —NR$^f$SO$_2$R$^o$, —S(O)$_m$R$^o$, CONR$^i$NHR$^o$ or $C_{1-10}$ alkyl wherein 2 or 3 nonadjacent carbon atoms in the alkyl chain can be replaced with —O—, —S— or —NR$^f$; $R^2$ is hydrogen, $C_{1-6}$ alkyl, $C_{3-6}$ cycloalkyl, $C_{3-6}$ cycloalkyl-$C_{1-3}$ alkyl, $C_{1-3}$alkoxycarbonyl-$C_{1-3}$ alkyl, $C_{1-6}$ haloalkyl, or aralkyl; and, $R^{a''}$, $R^{b''}$, $R^3$, $R^4$, $R^f$, $R^g$, $R^i$, $R^j$, $R^m$, $R^o$, $Z$, $A^1$, $A^2$, $A^3$, m, n are as defined hereinabove.

In another embodiment of the present invention there is provided compounds useful for preventing or treating disorders alleviated by administering a positive allosteric modulator of the $GABA_A$ receptor said compound comprising a compound according to formula I wherein $R^1$ is $CHR^fR^g$, $C_{2-10}$ alkynyl, $C_{1-6}$ haloalkyl, halogen; $R^2$ is hydrogen, $C_{1-6}$ alkyl; $R^3$ is optionally substituted aryl; and, $R^4$, $R^{a''}$, $R^{b''}$, $R^f$, $R^h$, $R^g$, $R^j$, $R^k$, $R^m$, $R^o$, $X^1$, $X^2$, $A^1$, $A^2$, $A^3$, m, n are as defined hereinabove.

In another embodiment of the present invention there is provided compounds useful for preventing or treating disorders alleviated by administering a positive allosteric modulator of the $GABA_A$ receptor said compound comprising a compound according to formula I wherein $R^1$ is —X$^2$C(=O)X$^1$R$^f$ or —S(O)$_m$R$^h$; $R^2$ is hydrogen or $C_{1-6}$alkyl; $R^3$ is optionally substituted aryl; $X^2$ is NR$^{f1}$; m is 2; and, $R^4$, $R^{a''}$, $R^{b''}$, $R^f$, $R^{f1}$, $R^h$, $R^j$, $R^k$, $R^o$, $X^1$, $A^1$, $A^2$, $A^3$, n are as defined hereinabove.

In another embodiment of the present invention there is provided compounds useful for preventing or treating disorders alleviated by administering a positive allosteric modulator of the $GABA_A$ receptor said compound comprising a compound according to formula I wherein $R^1$ is $CHR^fR^g$; $R^g$ is —X$^2$C(=O)X$^1$R$^f$; $R^2$ is hydrogen or $C_{1-6}$ alkyl; $R^3$ is optionally substituted aryl; and, $R^4$, $R^{a''}$, $R^{b''}$, $R^f$, $R^{f1}$, $X^1$, $X^2$, $A^1$, $A^2$, $A^3$, n are as defined hereinabove.

In another embodiment of the present invention there is provided a method for preventing or treating disorders alleviated by administering a positive allosteric modulator of the $GABA_A$ receptor said compound comprising a compound according to formula I wherein $R^1$, $R^2$, $R^3$, $R^4$, $R^a$, $R^{a'}$, $R^{a''}$, $R^{a'''}$, $R^b$, $R^{b'}$, $R^{b''}$, $R^{b'''}$, $R^c$, $R^d$, $R^e$, $R^f$, $R^{f1}$, $R^g$, $R^h$, $R^i$, $R^j$, $R^k$, $R^m$, $R^o$, $X^1$, $X^2$, $Z$, $A^1$, $A^2$, $A^3$, m, n are as defined hereinabove.

In another embodiment of the present invention there is provided a method for preventing or treating disorders alleviated by administering a positive allosteric modulator of the $GABA_A$ receptor said compound comprising a compound according to formula I wherein $R^1$ is —NR$^a$R$^b$, —CR$^c$R$^d$R$^e$, CHR$^f$R$^g$, CO$_2$R$^a$, —C(O)NR$^a$R$^b$; hydrogen, $C_{2-10}$ alkynyl, $C_{1-6}$ haloalkyl, cycloalkenyl, halogen, cyano, —C(=Z)R$^o$, —NR$^f$SO$_2$R$^o$, —S(O)$_m$R$^o$, CONR$^i$NHR$^o$, aryl, heteroaryl, where each aryl or heteroaryl is optionally substituted with one or more substituents independently selected from $C_{1-6}$ alkyl, $C_{1-6}$ alkoxy, $C_{1-6}$ alkylthio, $C_{1-6}$ alkylsulfonyl, halogen, haloalkyl, cyano, nitro, —C(O)NR$^{a'}$R$^{b'}$, and —NR$^{a'}$R$^{b'}$, where R$^{a'}$ and R$^{b'}$ are each independently selected from the group consisting of hydrogen, $C_{1-9}$ alkyl, and $C_{1-9}$ alkylcarbonyl or $R^1$ is $C_{1-10}$ alkyl wherein 2 or 3 nonadjacent carbon atoms in the alkyl chain can be replaced with —O—, —S— or —NR$^f$; $R^2$ is hydrogen, $C_{1-6}$ alkyl, $C_{3-6}$ cycloalkyl, $C_{3-6}$ cycloalkyl-$C_{1-3}$ alkyl, $C_{1-6}$ alkylcarbonyl, $C_{1-6}$ alkylsulfonyl, aryl, or arylalkyl, wherein said aryl or arylalkyl is optionally substituted with one or more substituents independently selected from $C_{1-6}$ alkyl, haloalkyl, $C_{1-6}$ alkoxy, and halogen; $R^g$ is $C_{2-10}$ alkenyl; and, $R^3$, $R^4$, $R^a$, $R^{a'}$, $R^{a''}$, $R^{a'''}$, $R^b$, $R^{b'}$, $R^{b''}$, $R^{b'''}$, $R^c$, $R^d$, $R^e$, $R^f$, $R^{f1}$, $R^i$, $R^o$, $Z$, $A^1$, $A^2$, $A^3$, m, n are as defined hereinabove.

In another embodiment of the present invention there is provided a method for preventing or treating disorders alleviated by administering a positive allosteric modulator of the $GABA_A$ receptor said compound comprising a compound according to formula I wherein $R^1$ is —NR$^a$R$^b$, —CR$^c$R$^d$R$^e$, CHR$^f$R$^g$, CO$_2$R$^a$, —C(O)NR$^a$R$^b$, hydrogen, $C_{2-10}$ alkynyl, $C_{1-6}$ haloalkyl, cycloalkenyl, halogen, cyano, —C(=Z)R$^o$, —NR$^f$SO$_2$R$^o$, —S(O)$_m$R$^o$, CONR$^i$NHR$^o$, or $R^1$ is $C_{1-10}$ alkyl wherein 2 or 3 nonadjacent carbon atoms in the alkyl chain can be replaced with —O—, —S— or —NR$^f$; R$^c$ is hydrogen, hydroxy, $C_{1-6}$ alkoxy, or —NR$^{a'''}$R$^{b'''}$; $R^d$ and $R^e$ are each independently selected from the group consisting of hydrogen, $C_{1-9}$ alkyl, hydroxyalkyl, $C_{1-6}$ alkoxyalkyl, $C_{1-6}$ alkylthioalkyl, $C_{3-6}$ cycloalkyl $C_{1-3}$ alkyl; or R$^c$ and R$^d$ are taken together to form a divalent group selected from $C_{1-6}$ alkylidenyl, $C_{1-6}$ heteroalkylidenyl, $C_{3-6}$ cycloalkylidenyl, $C_{3-6}$ cycloalkyl-alkylidenyl; or $R^d$ and $R^e$ are taken together with the carbon to which they are attached to form a cycloalkyl or heterocyclyl ring; $R^g$ is $C_{2-10}$ alkenyl; and, $R^2$, $R^3$, $R^4$, $R^a$, $R^{a''}$, $R^{a'''}$, $R^b$, $R^{b''}$, $R^{b'''}$, $R^f$, $R^i$, $R^o$, $Z$, $A^1$, $A^2$, $A^3$, m, n are as defined hereinabove.

In another embodiment of the present invention there is provided a method for preventing or treating disorders alleviated by administering a positive allosteric modulator of the $GABA_A$ receptor said compound comprising a compound according to formula I wherein $R^1$ is —X$^2$C(=O)X$^1$R$^f$ or —S(O)$_m$R$^h$; $R^2$ is hydrogen or $C_{1-6}$alkyl; $R^3$ is optionally substituted aryl; $X^2$ is NR$^{f1}$; m is 2; and, $R^4$, $R^{a''}$, $R^{b''}$, $R^f$, $R^{f1}$, $R^h$, $R^j$, $R^k$, $R^o$, $X^1$, $A^1$, $A^2$, $A^3$, n are as defined hereinabove.

In another embodiment of the present invention there is provided a method for preventing or treating disorders alleviated by administering a positive allosteric modulator of the $GABA_A$ receptor said compound comprising a compound according to formula I wherein $R^1$ is $CHR^fR^g$; $R^g$ is —X$^2$C(=O)X$^1$R$^f$; $R^2$ is hydrogen or $C_{1-6}$ alkyl; $R^3$ is optionally substituted aryl; and, $R^4$, $R^{a''}$, $R^{b''}$, $R^f$, $R^{f1}$, $X^1$, $X^2$, $A^1$, $A^2$, $A^3$, n are as defined hereinabove.

In another embodiment of the present invention there is provided a method for preventing or treating depression, anxiety, bipolar manic disorder, schizophrenia, learning or cognitive disorders, convulsions, seizures or pain by administering a positive allosteric modulator of the $GABA_A$ receptor said compound comprising a compound according to formula I wherein $R^1$, $R^2$, $R^3$, $R^4$, $R^a$, $R^{a'}$, $R^{a''}$, $R^{a'''}$, $R^b$, $R^{b'}$, $R^{b''}$, $R^{b'''}$, $R^c$, $R^d$, $R^e$, $R^f$, $R^{f1}$, $R^g$, $R^h$, $R^i$, $R^j$, $R^k$, $R^m$, $R^o$, $X^1$, $X^2$, Z, $A^1$, $A^2$, $A^3$, m, n are as defined hereinabove.

In another embodiment of the present invention there is provided a method for preventing or treating depression, anxiety, bipolar manic disorder, schizophrenia, learning or cognitive disorders, convulsions, seizures or pain by co-administering a positive allosteric modulator of the GABA$_A$ receptor said compound comprising a compound according to formula I wherein $R^1$, $R^2$, $R^3$, $R^4$, $R^a$, $R^{a'}$, $R^{a''}$, $R^{a'''}$, $R^b$, $R^{b'}$, $R^{b''}$, $R^{b'''}$, $R^c$, $R^d$, $R^e$, $R^f$, $R^{f1}$, $R^g$, $R^h$, $R^i$, $R^j$, $R^k$, $R^m$, $R^o$, $X^1$, $X^2$, Z, $A^1$, $A^2$, $A^3$, m, n are as defined hereinabove in combination with a selective serotonin reuptake inhibitor, a corticotropin releasing factor antagonist, or a phosphodiesterase IV inhibitor.

In another embodiment of the present invention there is provided a method for preventing or treating disorders alleviated by administering a selective positive allosteric modulator of the α2 subtype of the GABA$_A$ receptor with respect to the α1 subtype comprising a compound according to formula I wherein $R^1$, $R^2$, $R^3$, $R^4$, $R^a$, $R^{a'}$, $R^{a''}$, $R^{a'''}$, $R^b$, $R^{b'}$, $R^{b''}$, $R^{b'''}$, $R^c$, $R^d$, $R^e$, $R^f$, $R^{f1}$, $R^g$, $R^h$, $R^i$, $R^j$, $R^k$, $R^m$, $R^o$, $X^1$, $X^2$, Z, $A^1$, $A^2$, $A^3$, m, n are as defined hereinabove.

In another embodiment of the present invention there is provided a pharmaceutical composition for preventing or treating disorders alleviated by a positive allosteric modulator of a GABA$_A$ receptor said composition comprising a therapeutically effective amount of a compound according to formula I wherein $R^1$ is $CHR^fR^g$, $C_{2-10}$ alkynyl, $C_{1-6}$ haloalkyl, halogen, cyano, —C(=Z)R$^o$, —X$^2$C(=O)X$^1$R$^f$, NR$^f$SO$_2$R$^o$, —N[C(=O)OR$^m$]$_2$, —N=CR$^f$NR$^j$R$^k$; —S(O)$_m$R$^h$, CONR$^i$NHR$^o$ or $C_{1-10}$ alkyl wherein 2 or 3 nonadjacent carbon atoms in the alkyl chain can be replaced with —O—, —S— or —NR$^f$; $R^2$ is hydrogen, $C_{1-6}$ alkyl, $C_{3-6}$ cycloalkyl, $C_{3-6}$ cycloalkyl-$C_{1-3}$ alkyl, $C_{1-3}$alkoxycarbonyl-$C_{1-3}$ alkyl, $C_{1-6}$ haloalkyl, or aralkyl; and, $R^3$, $R^4$, $R^{a''}$, $R^{b''}$, $R^f$, $R^{f1}$, $R^g$, $R^{h6}$, $R^i$, $R^j$, $R^k$, $R^m$, $R^o$, $X^1$, $X^2$, Z, $A^1$, $A^2$, $A^3$, m, n are as defined hereinabove, admixed with at least one diluent, excipient or carrier.

In another embodiment of the present invention there is provided a pharmaceutical composition for preventing or treating disorders alleviated by a positive allosteric modulator of a GABA$_A$ receptor said composition comprising a therapeutically effective amount of a compound according to formula I wherein $R^1$ is $CHR^fR^g$, $C_{2-10}$ alkynyl, $C_{1-6}$ haloalkyl, halogen, cyano, —C(=Z)R$^o$, —NR$^f$SO$_2$R$^o$, —S(O)$_m$R$^o$, CONR$^i$NHR$^o$ or $C_{1-10}$ alkyl wherein 2 or 3 nonadjacent carbon atoms in the alkyl chain can be replaced with —O—, —S— or —NR$^f$; $R^2$ is hydrogen, $C_{1-6}$alkyl, $C_{3-6}$ cycloalkyl, $C_{3-6}$ cycloalkyl-$C_{1-3}$ alkyl, $C_{1-3}$ alkoxycarbonyl-$C_{1-3}$ alkyl; $C_{1-6}$ haloalkyl, or aralkyl; and, $R^3$, $R^4$, $R^{a''}$, $R^{b''}$, $R^f$, $R^g$, $R^i$, $R^j$, $R^m$, $R^o$, Z, $A^1$, $A^2$, $A^3$, m, n are as defined hereinabove, admixed with at least one diluent, excipient or carrier.

In another embodiment of the present invention there is provided a pharmaceutical composition for preventing or treating disorders alleviated by a positive allosteric modulator of a GABA$_A$ receptor said composition comprising both a therapeutically effective amount of a compound according to formula I wherein $R^1$ is $CHR^fR^g$, $C_{2-10}$ alkynyl, $C_{1-6}$ haloalkyl, halogen, cyano, —C(=Z)R$^o$, —X$^2$C(=O)X$^1$R$^f$, NR$^f$SO$_2$R$^o$, —N[C(=O)OR$^m$]$_2$, —N=CR$^f$NR$^j$R$^k$; —S(O)$_m$R$^h$, CONR$^i$NHR$^o$ or $C_{1-10}$ alkyl wherein 2 or 3 nonadjacent carbon atoms in the alkyl chain can be replaced with —O—, —S— or —NR$^f$; $R^2$ is hydrogen, $C_{1-6}$ alkyl, $C_{3-6}$ cycloalkyl, $C_{3-6}$ cycloalkyl-$C_{1-3}$ alkyl, $C_{1-3}$alkoxycarbonyl-$C_{1-3}$ alkyl; $C_{1-6}$ haloalkyl, or aralkyl; and, $R^3$, $R^4$, $R^{a''}$, $R^{b''}$, $R^f$, $R^{f1}$, $R^g$, $R^h$, $R^i$, $R^j$, $R^k$, $R^m$, $R^o$, $X^1$, $X^2$, Z, $A^1$, $A^2$, $A^3$, m, n are as defined hereinabove, and selective serotonin reuptake inhibitor, or a corticotropin releasing factor antagonist, or a phosphodiesterase IV inhibitor, the combination being admixed with at least one diluent, excipient or carrier.

Definitions

Unless otherwise stated, the following terms used in this Application, including the specification and claims, have the definitions given below.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Detailed Description of the Invention.

The term "alkyl" as used herein means a monovalent unbranched or branched saturated hydrocarbon radical, consisting solely of carbon and hydrogen atoms, having from one to ten carbon atoms inclusive, unless otherwise indicated. Examples of alkyl radicals include, but are not limited to, methyl, ethyl, propyl, iso-propyl, iso-butyl, sec-butyl, tert-butyl, pentyl, n-hexyl, and the like. The term "lower alkyl" lower alkyl refers to alkyl group having from one to six carbon atoms.

The term "alkenyl" as used herein denotes an unsubstituted hydrocarbon chain radical having from 2 to 10 carbon atoms having one or two olefinic double bonds, preferably one olefinic double bond. $C_{2-10}$ alkenyl" as used herein refers to an alkenyl composed of 2 to 10 carbons. Examples are vinyl, 1-propenyl, 2-propenyl (allyl) or 2-butenyl (crotyl).

The term "alkylene" as used herein means a divalent unbranched or branched saturated hydrocarbon radical consisting solely of carbon and hydrogen atoms, having from one to ten carbon atoms inclusive, unless otherwise indicated. Examples of alkylene radicals include, but are not limited to, methylene, ethylene, propylene, 2-methylethylene, 3-methylpropylene, 2-ethylethylene, pentylene, hexylene, and the like.

The term "alkynyl" as used herein denotes an unbranched or branched hydrocarbon chain radical having from 2 to 10 carbon atoms, preferably 2 to 4 carbon atom, and having one or where possible two triple bonds, preferably one triple bond. $C_{2-10}$ alkenyl" as used herein refers to an alkenyl composed of 2 to 10 carbons Examples are ethynyl, 1-propynyl, 2-propynyl, 1-butynyl, 2-butynyl or 3-butynyl.

The term "alkoxy" as used herein means a radical —OR, wherein R is a lower alkyl radical as defined herein. Examples of alkoxy radicals include, but are not limited to, methoxy, ethoxy, isopropoxy, and the like.

The terms "alkoxycarbonyl" and "aryloxycarbonyl" as used herein denotes a group of formula —C(=O)OR wherein R is alkyl or aryl respectively and alkyl and aryl are as defined.

The terms "alkylsulfonyl" and "arylsulfonyl" as used herein denotes a group of formula —S(=O)$_2$R wherein R is alkyl or aryl respectively and alkyl and aryl arenas defined herein. The terms "alkylsulfonyloxy" and "arylsulfonyloxy" as used herein denotes a group of formula —OS(=O)$_2$R wherein R is alkyl or aryl respectively and alkyl and aryl are as defined herein.

The term "acylamino" as used herein denotes a group of formula —NHC(=O)R wherein R is hydrogen or lower alkyl as defined herein The terms "alkoxycarbonylalkyl" and "aryloxycarbonylalkyl" as used herein denotes the radical R'R" where R' is an alkoxycarbonyl or aryloxycarbonyl radical and R" is alkylene as defined herein and the attachment point of the aryl(alkoxy)carbonylalkyl radical will be on the alkylene radical.

The term "alkylthio" or "thioalkyl" as used herein denotes an —S-alkyl group, wherein alkyl is as defined above such as meththio, ethylthio, n-propylthio, i-propylthio, n-butylthio, hexylthio, including their isomers. "Lower alkylthio" or "lower thioalkyl" as used herein denotes an alkylthio group with a "lower alkyl" group as previously defined. "$C_{1-10}$ alkylthio" as used herein refers to an-S-alkyl wherein alkyl is $C_{1-10}$.

The term "alkylthioalkyl" as used herein denotes the radical R'R" where R' is an alkylthio radical and R" is alkylene as defined herein and the attachment point of the alkylthioalkyl radical will be on the alkylene radical.

The term "aminosulfonyl" as used herein refers to the radical —S(O)$_2$NH$_2$. The terms "alkylaminosulfonyl" and "dialkylaminosulfonyl" as used herein refers to the radical —S(O)$_2$NR'R", wherein R' and R" are hydrogen and lower alkyl and R' and R" are independently lower alkyl respectively. Examples of alkylaminosulfonyl include, but are not limited to methylaminosulfonyl, iso-propylaminosulfonyl. Examples of dialkylaminosulfonyl include, but are not limited to dimethylaminosulfonyl, iso-propyl-methylaminosulfonyl.

The term "cycloalkyl" as used herein means a monovalent saturated carbocyclic radical consisting of one or more rings, and consisting solely of carbon and hydrogen atoms, having from three to eight carbon atoms inclusive, unless otherwise indicated. Examples of cycloalkyl radicals include, but are not limited to, cyclopropyl, cyclobutyl, cyclopentyl, cycloheptyl, and the like.

The term "substituted cycloalkyl" as used herein means the cycloalkyl as defined herein, including one to three substituents, such as hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino. Examples of cycloalkyl radicals include, but are not limited to, 3-ethylcyclobutyl, 4-hydroxycyclohexyl 3-chlorcyclopentyl and the like.

The term "cycloalkylalkyl" as used herein means a radical —R'R", wherein R' is an alkylene radical, and R" is a cycloalkyl or substituted cycloalkyl radical as defined herein. Examples of cycloalkylalkyl radicals include, but are not limited to, cyclopropylmethyl, cyclohexylmethyl, cyclopentylethyl, and the like.

The term "cycloalkenyl" as used herein means a monovalent unsaturated carbocyclic radical consisting of one or more rings, and consisting solely of carbon and hydrogen atoms, having from one to ten carbon atoms inclusive, unless otherwise indicated. Examples of cycloalkenyl radicals include, but are not limited to, cyclobuten-1-yl, cyclopenten-1-yl and the like.

The term "substituted cycloalkenylyl" as used herein means the cycloalkenyl as defined herein, including one to three substituents, such as hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, and sulfonylamino, unless otherwise indicated. Examples of substituted cycloalkenyl radicals include, but are not limited to 3-ethylcyclobuten-1-yl, 3-fluorocyclohepten-1-yl, and the like.

The term "cyano" as used herein refers to a carbon linked to a nitrogen by a triple bond, i.e., —C≡N.

The term "halogen" or "halo" as used herein means the radical fluoro, bromo, chloro, or iodo, and combinations thereof.

The term "haloalkyl" as used herein means a lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl and the like.

The term "aryl" or "aromatic" as used herein means a monocyclic or bicyclic radical of 6 to 12 ring carbon atoms having at least one aromatic ring, with the understanding that the attachment point of the aryl radical will be on an aromatic ring. The aryl radical is optionally substituted independently with one or more substituents selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —SO$_2$NR'R" (where R' and R" are independently hydrogen or alkyl), alkoxy, haloalkoxy, alkoxycarbonyl, carbamoyl, hydroxy, halo, nitro, cyano, thio, methylenedioxy or ethylenedioxy. More specifically the term aryl includes, but is not limited to, phenyl, naphthyl, tetrahydronaphthyl, 3,4-methylenedioxyphenyl, 1,2,3,4-tetrahydroquinolin-7-yl, 1,2,3,4-tetrahydro-isoquinoline-7-yl, and the like.

The terms "heteroaryl" and "heteroaromatic" as used herein means a monocyclic or bicyclic radical of 5 to 12 ring atoms having at least one aromatic ring containing one, two, or three ring heteroatoms selected from nitrogen, oxygen, and sulfur, the remaining ring atoms being carbon, with the understanding that the attachment point of the heteroaryl radical will be on an aromatic ring. The heteroaryl ring is optionally substituted independently with one or more substituents selected from alkyl, haloalkyl, hydroxyalkyl, heteroalkyl, acyl, acylamino, amino, alkylamino, dialkylamino, alkylthio, alkylsulfinyl, alkylsulfonyl, alkylsulfonyloxy, —SO$_2$NR'R" (where R' and R" are independently hydrogen or alkyl), alkoxy, haloalkoxy, alkoxycarbonyl, carbamoyl; hydroxy, halo, nitro, cyano, thio, methylenedioxy or ethylenedioxy. Examples of heteroaryl moieties include monocyclic aromatic heterocycles having 5 to 6 ring atoms and 1 to 2 heteroatoms include, but is not limited to, including, and includes, but is not limited to, pyridinyl, furanyl, thienyl, thiazolyl, isothiazolyl, triazolyl, imidazolyl, isoxazolyl, pyrrolyl, pyrazolyl, and pyrimidinyl, and derivatives thereof, and bicyclic aromatic moieties having 9 to 10 ring atoms, including 1 to 3 heteroatoms, and includes, but is not limited to, benzofuranyl, tetrahydrobenzofuranyl, isobenzofuranyl, benzothiazolyl, benzoisothiazolyl, benzotriazolyl, indolyl, isoindolyl, benzoxazolyl, quinolinyl, 5,6,7,8-tetrahydroquinolinyl, isoquinolinyl, 5,6,7,8-tetrahydroisoquinolinyl, benzimidazolyl, benzisoxazolyl, and benzothienyl, and derivatives thereof.

The term "heteroalkyl" as used herein means an alkyl radical as defined herein wherein one, two, or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkyl-C$_{1-3}$ alkyl; and R$^b$ and R$^c$ are independently selected from the group consisting of hydrogen, acyl, alkyl, cycloalkyl, or cycloalkyl-C$_{1-3}$ alkyl; when n is 0, R$^d$ is hydrogen, alkyl, cycloalkyl, and cycloalkyl-C$_{1-3}$ alkyl and when n is 1 or 2, $R^d$ is alkyl, cycloalkyl, cycloalkyl-$C_{1-3}$ alkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-methoxyethyl, 2-ethoxyethyl, 3-methoxypropyl, 2-aminoethyl, 3-aminopropyl, 2-methylsulfonylethyl, aminosulfonylmethyl, aminosulfonylethyl, aminosulfonylpropyl, methylaminosulfonyl-methyl, methylaminosulfonylethyl, methylaminosulfonylpropyl, and the like.

The term "heterocyclyl" as used herein means a saturated or unsaturated non-aromatic monocyclic or bicyclic radical of 3 to 10 ring atoms in which one or two ring atoms are heteroatom containing groups selected from NR', O, or S(O)$_n$ (where R' is alkyl, heteroalkyl, or hydrogen, and n is an integer from 0 to 2), the remaining ring atoms being carbon. The heterocyclyl radical is optionally substituted with one or more substituents selected from the group consisting of hydroxy, oxo, alkyl, haloalkyl, hydroxyalkyl, heteroalkyl, and acyl. The term heterocyclyl includes, but is not limited to, tetrahydropyranyl, piperidino, tetrahydropyrimidin-5-yl, tetrahydropyrimidin-1-yl, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, tetrahydroquinolin-1-yl and tetrahydroisoquinolin-2-yl, and the like.

The term "arylalkyl" or "aralkyl" as used herein means a radical —R'R" where R' is an alkylene radical and R" is an aryl radical as defined herein. Examples of arylalkyl radicals include, but are not limited to, 4-fluorophenylmethyl, 3,4-dichlorophenylethyl, and the like.

The term "heteroarylalkyl" as used herein means a radical —R'R" where R' is an alkylene radical and R" is a heteroaryl radical as defined herein. Examples of heteroarylalkyl radicals include, but are not limited to, such as 3-pyridinylmethyl, 4-chloropyrimidin-2-ylmethyl, 2-thiophen-2-ylethyl, and the like.

The term "heterocyclylalkyl" as used herein means a radical —R'R" where R' is an alkylene radical and R" is a heterocyclyl radical as defined herein. Examples of heterocyclylalkyl radicals include, but are not limited to, tetrahydropyran-2-ylmethyl, 2-piperidinylmethyl, 3-piperidinylmethyl, morpholin-1-ylpropyl, and the like.

The terms "amino", "alkylamino" and "dialkylamino" as used herein refer to —$NH_2$, —NHR and —$NR_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2(CH_2)$n-, $RHN(CH_2)$n-, and $R_2N(CH_2)$n- respectively wherein n is 1 to 6 and R is alkyl as defined above. "$C_{1-10}$ alkylamino" as used herein refers to an-aminoalkyl wherein alkyl is $C_{1-10}$. Examples of alkylamino and dialkylamino radicals include, but are not limited to, methylamino, ethylamino, cyclopropylmethylamino, dicyclopropylmethylamino, dimethylamino, methylethylamino, diethylamino, di(1-methylethyl)amino, and the like.

The term "acyl" means a formyl radical of the formula —C(O)H, or a carbonyl radical of the formula —C(O)R', where R' is selected from the group consisting of $C_{1-18}$ alkyl, cycloalkyl, cycloalkylalkyl, haloalkyl, heteroalkyl, heterocyclyl, heterocyclylalkyl, aryl, arylalkyl, heteroaryl, heteroarylalkyl, alkoxy, or NR'R", as defined herein, wherein R' and R" are hydrogen of alkyl or R', R" and the nitrogen to which they are attached are a pyrrolidinyl, piperidinyl, morpholinyl, or piperazinyl group.

The term "alkylidenyl" as used herein means a bivalent radical =CRR', wherein R and R' are independently an alkyl radical or hydrogen, as defined herein. Examples of alkylidenyl radicals include, but are not limited to, ethylidenyl, propylidenyl, butylidenyl, and the like.

The term "cycloalkylidenyl" as used herein means a bivalent radical =CRR', wherein R and R' are taken together with the carbon to which they are attached to form a bivalent cycloalkyl radical, as defined herein. Examples of cycloalkylidenyl radicals include, but are not limited to, cyclopentylidenyl, 3-fluorocyclohexylidenyl, and the like.

The term "cycloalkyl-alkylidenyl" as used herein means a bivalent radical =CRR', wherein R is an alkyl radical or hydrogen, and R' is a cycloalkyl radical, as defined herein. Examples of cycloalkyl-alkylidenyl radicals include, but are not limited to, cyclopropylmethylidenyl, cyclohexylmethylidenyl, 1-cyclopentylethylidenyl, and the like.

The term "cycloalkylalkyl-alkylidenyl" as used herein means a bivalent radical =CRR', wherein R is an alkyl radical or hydrogen, and R' is a cycloalkylalkyl radical, as defined herein. Examples of cycloalkylalkyl-alkylidenyl radicals include, but are not limited to, 2-cyclopentylethylidenyl, 1-cyclohexylpropyliden-2-yl, and the like.

The term "heteroalkylidenyl" as used herein means a bivalent radical =CRR', wherein R is an heteroalkyl radical, an haloalkyl radical, an alkyl radical, or hydrogen, and R' is an heteroalkyl radical or an haloalkyl radical, as defined herein. Examples of heteroalkylidenyl radicals include, but are not limited to, 3,3,3-trifluoropropylidenyl, 2-hydroxybutylidenyl, 3-aminopropylidenyl, and the like.

The term "heterocyclylidenyl" as used herein means a bivalent radical =CRR', wherein R and R' are taken together with the carbon to which they are attached to form a bivalent heterocyclyl radical, as defined herein. Examples of heterocyclylidenyl radicals include, but are not limited to, pyrrolidinyliden-2-yl, tetrahydropyranyliden4-yl, piperidinyliden4-yl, and the like.

The term "heterocyclyl-alkylidenyl" as used herein means a bivalent radical =CRR', wherein R is an alkyl radical or hydrogen, and R' is a heterocyclyl radical, as defined herein. Examples of heterocyclyl-alkylidenyl radicals include, but are not limited to, 4-piperidinylmethylidenyl, 4-methyl-1-piperazinylmethylidene, and the like.

The term "heterocyclylalkyl-alkylidenyl" as used herein means a bivalent radical =CRR', wherein R is an alkyl radical or hydrogen, and R' is a heterocyclylalkyl radical, as defined herein. Examples of heterocyclylalkyl-alkylidenyl radicals include, but are not limited to, 2-(tetrahydropyran-4-yl)ethylidenyl, 1-(piperidin-3-yl)propyliden-2-yl, and the like.

The term "arylalkylidenyl" as used herein means a bivalent radical =CRR', wherein R is an aryl radical, an alkyl radical, or hydrogen, and R' is an aryl radical, as defined herein. Examples of arylalkylidenyl radicals include, but are not limited to, 4-chlorophenylmethylidenyl, 6,7-dimethoxynaphth-2-ylmethylidenyl, and the like.

The term "arylalkyl-alkylidenyl" as used herein means a bivalent radical =CRR', wherein R is an alkyl radical or hydrogen, and R' is an arylalkyl radical, as defined herein. Examples of arylalkyl-alkylidenyl radicals include, but are not limited to, 2-(4-trifluoromethylphenyl)ethylidenyl, 1-(3,4-dichlorophenyl)propyliden-2-yl, and the like.

The term "heteroarylalkylidenyl" as used herein means a bivalent radical =CRR', wherein R is an alkyl radical or hydrogen, and R' is a heteroaryl radical, as defined herein.

Examples of heteroarylalkylidenyl radicals include, but are not limited to, 3-pyridinylmethylidenyl, 4-chloro-2-pyrimidinylmethylidenyl, and the like.

The term "heteroarylalkyl-alkylidenyl" as used herein means a bivalent radical =CRR', wherein R is an alkyl radical or hydrogen, and R' is a heteroarylalkyl radical, as defined herein. Examples of heteroarylalkyl-alkylidenyl radicals include, but are not limited to, 2-(4-trifluoromethylpyrimidinyl)ethylidenyl, 1-(thiophen-2-yl)propyliden-2-yl, and the like.

The terms "hydroxyalkyl" and "alkoxyalkyl" as used herein denotes the radical R'R" where R' is an hydroxy radical or a alkoxy radical respectively and R" is alkylene as defined herein and the attachment point of the hydroxyalkyl radical will be on the alkylene radical.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like.

The term "optional" or "optionally" as used herein means that a subsequently described event or circumstance may, but need not, occur, and that the description includes instances where the event or circumstance occurs and instances in which it does not. For example, "optional bond" means that the bond may or may not be present, and that the description includes single, double, or triple bonds.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are nonsuperimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia* 1956, 12, 81; Cahn, *J. Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

The phrase "substantially pure" as used herein means at least about 90 mole percent, of the desired compound, enantiomer or stereoisomer is present compared to other possible configurations.

The phrase "pharmaceutically acceptable" as used herein means that which is useful in preparing a pharmaceutical composition that is generally safe, non-toxic, and neither biologically nor otherwise undesirable and includes that which is acceptable for veterinary as well as human pharmaceutical use.

The phrase "pharmaceutically acceptable salts" of a compound as used herein means salts that are pharmaceutically acceptable, as defined herein, and that possess the desired pharmacological activity of the parent compound. Such salts include:

(i) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (ii) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

The term "crystal forms" or "polymorphs" means crystal structures in which a compound can crystallize in different crystal packing arrangements, all of which have the same elemental composition. Different crystal forms usually have different X-ray diffraction patterns, infrared spectra, melting points, density, hardness, crystal shape, optical and electrical properties, stability and solubility. Recrystallization solvent, rate of crystallization, storage temperature, and other factors may cause one crystal form to dominate.

The term "solvates" as used herein means solvent additions forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like.

Examples of non-mammals include, but are not limited to, birds, and the like. The term "subject" does not denote a particular age or sex.

"Disease state" means any disease, condition, symptom, or indication. "Treating" or "treatment" of a disease state includes: (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms, or (iii) relieving the disease state, i.e., causing temporary or permanent regression of the disease state or its clinical symptoms.

"Mood disorders" or "affective disorders" means psychopathologic conditions in which a pervasive disturbance of mood constitutes the core manifestation. These terms subsume anxiety and related neuroses, especially the depressive form. Examples of "mood disorders" or "affective disorders" include, but are not limited to, depression, major depressive disorder, single episode depression, recurrent depression, child abuse induced depression, postpartum depression, dysthemia, unipolar disorder, bipolar disorder with manifestations of insomnia and eating disorder, dysthymic disorder, double depression, morbid and clinical depression, mania and cyclothymia.

"Obsessive-compulsive disorder" is characterized by recurrent, unwanted, intrusive ideas, images or impulses and an urge to do something to lessen the discomfort caused by the ideas, images or impulses. A "post traumatic stress disorder" occurs when a patient reexperiences a traumatic event that has occurred, which reexperience causes intense fear, helplessness, horror and results in the avoidance of stimuli associated with the trauma. Adjustment disorder with anxious mood is a type of anxiety, which unlike post traumatic stress disorder that results from an extreme stimuli, results from less extreme stimuli. The emotional or behavioral symptoms usually are in response to an identifiable psychosocial stressor.

"Social anxiety disorder" and "social phobia" are characterized by anxiety resulting from a specific social situations or performance based situations. Specific social phobia is a disorder in which a patient avoids a specific social situation. Social phobia can be contrasted with social anxiety disorder because the patient's anxiety can be attributed to a specific social or performance based situation, rather than social or performance based situations in general. For example, the patient may be uncharacteristically anxious about public speaking.

"Specific phobia" is an excessive or unreasonable fear, without apparent justification. Typically, an adult patient recognizes that the fear is excessive or unreasonable, but children may not recognize this. "Phobias" includes agoraphobia, specific phobias and social phobias. "Agoraphobia" is characterized by an anxiety about being in places or situations from which escape might be difficult or embarrassing or in which help may not be available in the event of a panic attack. Agoraphobia may occur without history of a panic attack. A "specific phobia" is characterized by clinically significant anxiety provoked by feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type where fear is cued by other stimuli. Specific phobias may also be referred to as simple phobias.

The disorders and conditions above are well known to those skilled on the art. Methods of diagnosing and a description of these conditions can be found in Diagnostic And Statistical Manual of Mental Disorders, Fourth Edition, American Psychiatric Association, Washington, D.C., 1994.

Combination therapy refers to the use of compounds of the present invention with other agents which are serotonin reuptake inhibitors, corticotrophin releasing factor antagonists or phosphodiesterase 4 inhibitors (PDE IV). Compounds which are in use or in development have been reviewed (P. Farvolden et al. *Exp Opin. Investig. Drugs* 2003 12(1):65-861; E. P. Zorrilla and G. F. Koob *Exp Opin. Investig. Drugs* 2004 13(7):799-828; T. E. Renau, *Cur. Opin. Investig. Drugs* 2004 5(1):2004. These references are incorporated by reference in their entirety.

| ABBREVIATIONS | |
|---|---|
| Ac | acetyl |
| AIBN | azo-bis-isobutyrylnitrile |
| Atm | atmospheres |
| BBN | 9-borabicyclo[3.3.1]nonane (9-BBN) |
| Boc | tert-butoxycarbonyl |
| BOC$_2$O | Di-tert-butyl pyrocarbonate or bocanhydride |
| Bn | benzyl |
| Bu | butyl |
| cbz or Z | benzyloxycarbonyl |
| DABCO | 1,4-diazabicyclo[2.2.2]octane |
| DAST | diethylaminosulfur trifluoride |
| Dba | dibenzylideneacetone |
| DBN | 1,5-diazabicyclo[4.3.0]non-5-ene |
| DBU | 1,8-diazabicyclo[5.4.0]undec-7-ene |
| DCE | 1,2-dichloroethane |
| DCM | dichloromethane |
| DEAD | diethyl azodicarboxylate |
| DIAD | di-iso-propylazodicarboxylate |
| DEIPA | diethyl iso-propylamine |
| DIBAL-H | di-iso-butylaluminumhydride |
| DMA | N,N-dimethyl acetamide |
| DMAP | 4-N,N-dimethylaminopyridine |
| DMF | N,N-dimethylformamide |
| DMSO | dimethyl sulfoxude |
| dppf | 1,1'-Bis(diphenylphosphino)ferrocene |
| EDCI | 1-(3-dimethylaminopropyl)-3-ethylcarbodiimide hydrochloride |
| EtOAc | ethyl acetate |
| Et$_2$O | diethyl ether |
| Et | ethyl |
| LiHMDS | lithium hexamethyl disilazane |
| i-Pr | iso-propyl |
| EtOH | ethanol |
| HOAc | acetic acid |
| HOBT | 1-N-hydroxybenzotriazole |
| HPLC | high pressure liquid chromatography |
| Me | methyl |
| MeCN | acetonitrile |
| MeOH | methanol |
| Mp | melting point |
| Ms | mass spectrum |
| MTBE | methyl t-butyl ether |
| NCA | N-carboxyanhydride |
| NBS | N-bromosuccinimide |
| NMP | N-methylpyrrolidone |
| PCC | pyridinium chlorochromate |
| PDC | pyridinium dichromate |
| Pr | propyl |
| Ph | phenyl |
| psi | pounds per square inch |
| pyr | pyridine |
| rt or RT | room temperature |
| TEA | Triethylamine (Et$_3$N) |

| ABBREVIATIONS | |
|---|---|
| Tf | triflate CF$_3$SO$_2$— |
| TFA | trifluoroacetic acid |
| TMHD | 2,2,6,6-tetramethylheptane-2,6-dione |
| TLC | thin layer chromatography |
| THF | tetrahydrofuran |
| TMS | trimethylsilyl |
| TsOH | p-toluenesulfonic acid monohydrate |
| UNCA | N-urethane-N-carboxyanhydride |

EXAMPLES OF COMPOUNDS

Examples of representative compounds within the scope of the invention provided in Table A-E depict representative compounds encompassed by the present invention. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. The following numbering system for these ring systems are as follows:

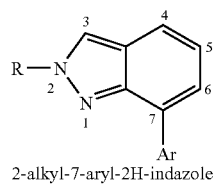

2-alkyl-7-aryl-2H-indazole

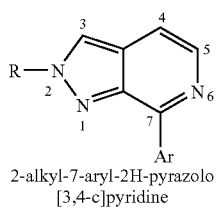

2-alkyl-7-aryl-2H-pyrazolo
[3,4-c]pyridine

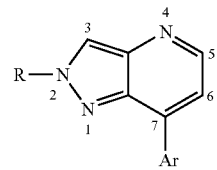

2-alkyl-7-aryl-2H-pyrazolo[4,3-b]
pyridine

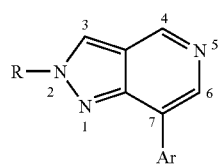

2-alkyl-7-aryl-2H-pyrazolo[4,3-c]
pyridine

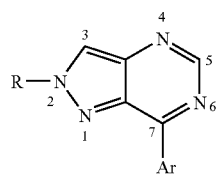

2-alkyl-7-aryl-2H-pyrazolo
[4,3-d]pyrimidine

The indazole compounds in Table A were prepared as depicted in Scheme 1. 3-Substituted indazoles in Table A were prepared by deprotonation of C-3 and quenching the resulting carbanion with alkyl halides, alkenyl halides, alkynyl halides or carbonyl compounds which directly afford compounds of the present invention or intermediates which further transformed to prepare said compounds. Alternatively direct electrophic substitution of the C-3 position can also be exploited to prepare compounds of the invention (e.g., 3-halo compounds). These processes are depicted in Schemes 2 and 4-7.

TABLE A

| Cpd # | Structure | Name | mp °C. | MH+ calcd (found) |
|---|---|---|---|---|
| A1 | 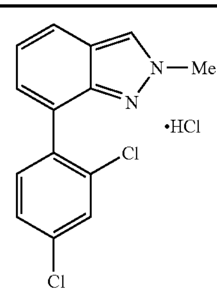 | 7-(2,4-Dichloro-phenyl)-2-methyl-2H-indazole; hydrochloride | 133-147 | 277 (277) |

TABLE A-continued

| Cpd # | Structure | Name | mp ° C. | MH+ calcd (found) |
|---|---|---|---|---|
| A2 | 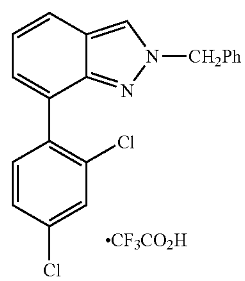 | 2-Benzyl-7-(2,4-dichloro-phenyl)-2H-indazole; compound with trifluoro-acetic acid | | 353 (353) |
| A3 | 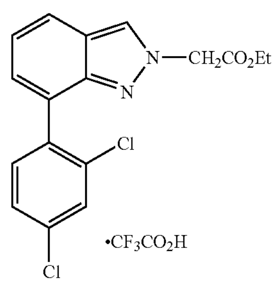 | [7-(2,4-Dichloro-phenyl)-indazol-2-yl]-acetic acid ethyl ester; compound with trifluoro-acetic acid | | 349 (349) |
| A5 | 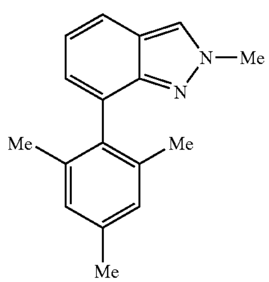 | 2-Methyl-7-(2,4,6-trimethyl-phenyl)-2H-indazole | 180-182 | 251 (251) |
| A6 | 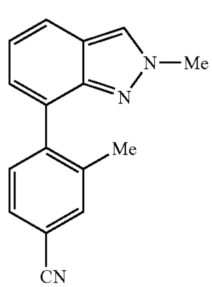 | 3-Methyl-4-(2-methyl-2H-indazol-7-yl)-benzonitrile | 101-105 | 248 (248) |
| A7 | 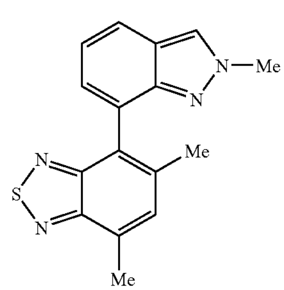 | 5,7-Dimethyl-4-(2-methyl-2H-indazol-7-yl)-benzo[1,2,5]-thiadiazole | | 295 (295) |

TABLE A-continued

| Cpd # | Structure | Name | mp ° C. | MH+ calcd (found) |
|---|---|---|---|---|
| A8 | 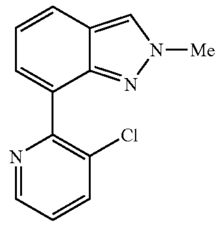 | 7-(3-Chloro-pyridin-2-yl)-2-methyl-2H-indazole | | 24 (244) |
| A9 | 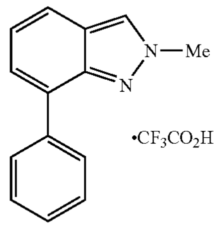 | 2-Methyl-7-phenyl-2H-indazole; compound with trifluoro-acetic acid | | 209 (209) |
| A10 | 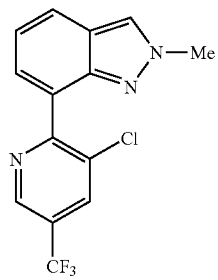 | 7-(3-Chloro-5-trifluoromethyl-pyridin-2-yl)-2-methyl-2H-indazole | | 312 (312) |
| A11 | 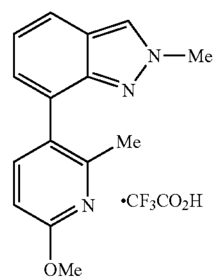 | 7-(6-Methoxy-2-methyl-pyridin-3-yl)-2-methyl-2H-indazole; compound with trifluoro-acetic acid | | 254 (254) |
| A12 | 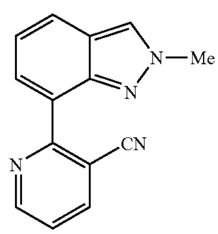 | 2-(2-Methyl-2H-indazol-7-yl)-nicotinonitrile | | 235 (235) |
| A13 | 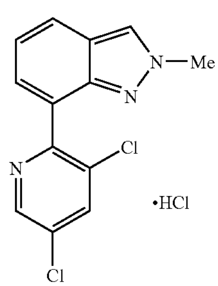 | 7-(3,5-Dichloro-pyridin-2-yl)-2-methyl-2H-indazole; hydrochloride | | 278 (278) |

TABLE A-continued

| Cpd # | Structure | Name | mp ° C. | MH+ calcd (found) |
|---|---|---|---|---|
| A14 | 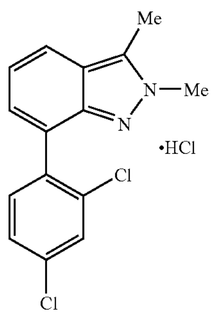 | 7-(2,4-Dichloro-phenyl)-2,3-dimethyl-2H-indazole; hydrochloride | 147-150 | 265 (265) |
| A15 | 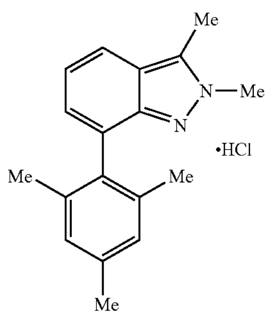 | 2,3-Dimethyl-7-(2,4,6-trimethyl-phenyl)-2H-indazole; hydrochloride | | 265 (265) |
| A16 | 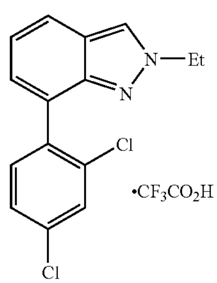 | 7-(2,4-Dichloro-phenyl)-2-ethyl-2H-indazole; compound with trifluoro-acetic acid | | 291 (291) |
| A17 | 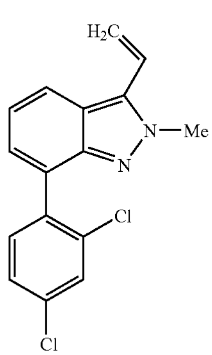 | 7-(2,4-Dichloro-phenyl)-2-methyl-3-vinyl-2H-indazole | | 303 (303) |

TABLE A-continued

| Cpd # | Structure | Name | mp ° C. | MH+ calcd (found) |
|---|---|---|---|---|
| A18 | 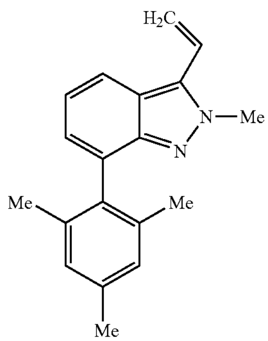 | 2-Methyl-7-(2,4,6-trimethyl-phenyl)-3-vinyl-2H-indazole | 85-95 | 277 (277) |
| A19 | 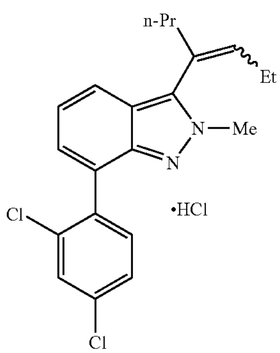 | 7-(2,4-Dichloro-phenyl)-2-methyl-3-((E)-1-propyl-but-1-enyl)-2H-indazole; hydrochloride | 148-150 | 373 (373) |
| A20 | 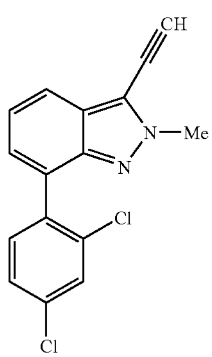 | 7-(2,4-Dichloro-phenyl)-3-ethynyl-2-methyl-2H-indazole | 129.9-130.9 | 301 (301) |
| A21 | 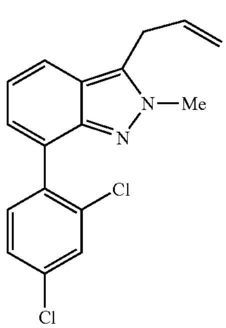 | 3-Allyl-7-(2,4-dichloro-phenyl)-2-methyl-2H-indazole | | 317 (317) |

TABLE A-continued

| Cpd # | Structure | Name | mp ° C. | MH+ calcd (found) |
|---|---|---|---|---|
| A22 | 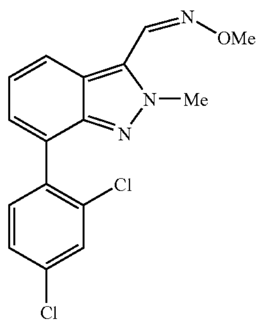 | 7-(2,4-Dichloro-phenyl)-2-methyl-2H-indazole-3-carbaldehyde O-methyl-oxime | 159.2-160.5 | 334 (334) |
| A23 | 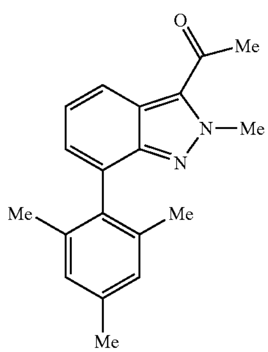 | 1-[2-Methyl-7-(2,4,6-trimethyl-phenyl)-2H-indazol-3-yl]-ethanone | | 293 (293) |
| A24 | 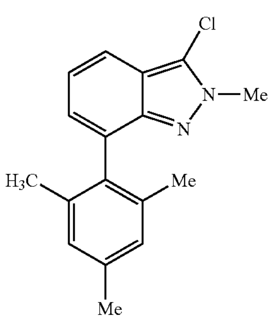 | 3-Chloro-2-methyl-7-(2,4,6-trimethyl-phenyl)-2H-indazole | | 285 (285) |
| A25 | 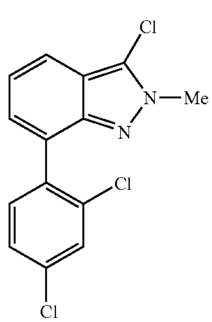 | 3-Chloro-7-(2,4-dichloro-phenyl)-2-methyl-2H-indazole | | 311 (311) |

TABLE A-continued

| Cpd # | Structure | Name | mp ° C. | MH+ calcd (found) |
|---|---|---|---|---|
| A26 | 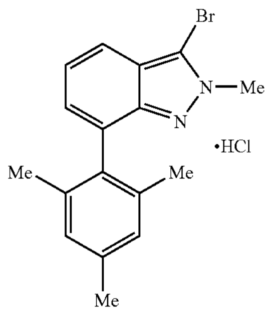 | 3-Bromo-2-methyl-7-(2,4,6-trimethyl-phenyl)-2H-indazole; hydrochloride | | 355 (355) |
| A27 | 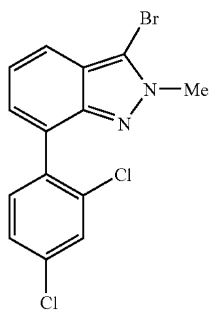 | 3-Bromo-7-(2,4-dichloro-phenyl)-2-methyl-2H-indazole | 137-139 | 355 (355) |
| A28 | 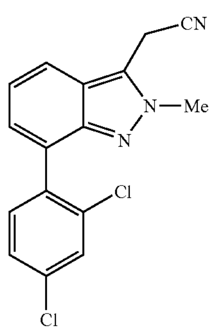 | [7-(2,4-Dichloro-phenyl)-2-methyl-2H-indazol-3-yl]-acetonitrile | | 316 (316) |
| A29 | 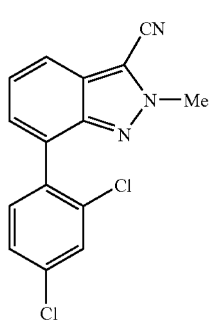 | 7-(2,4-Dichloro-phenyl)-2-methyl-2H-indazole-3-carbonitrile | 137-139 | 302 (302) |

TABLE A-continued

| Cpd # | Structure | Name | mp ° C. | MH+ calcd (found) |
|---|---|---|---|---|
| A30 | 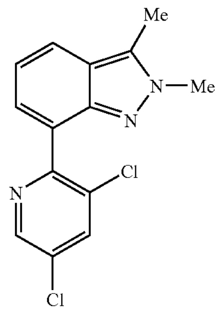 | 7-(3,5-Dichloro-pyridin-2-yl)-2,3-dimethyl-2H-indazole | | 292 (292) |
| A31 | 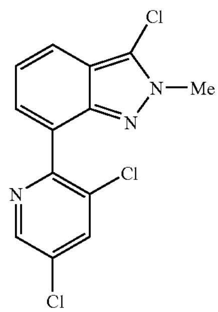 | 3-Chloro-7-(3,5-dichloro-pyridin-2-yl)-2-methyl-2H-indazole | | 312 (312) |
| A32 | 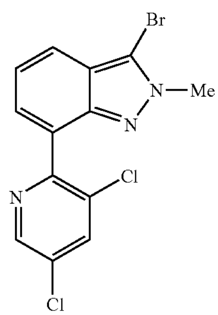 | 3-Bromo-7-(3,5-dichloro-pyridin-2-yl)-2-methyl-2H-indazole | 154.5-156.2 | 356 (356) |
| A33 | 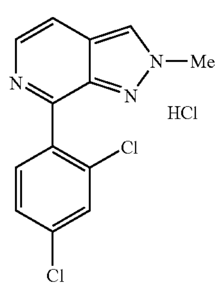 | 7-(2,4-Dichloro-phenyl)-2-methyl-2H-pyrazolo[3,4-c]pyridine; hydrochloride | 190.9-195.5 | 314.60 (278) |
| A34 | 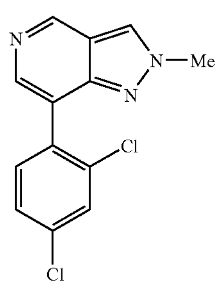 | 7-(2,4-Dichloro-phenyl)-2-methyl-2H-pyrazolo[4,3-c]pyridine | 153.9-155.3 | 278.14 (278) |

TABLE A-continued

| Cpd # | Structure | Name | mp ° C. | MH+ calcd (found) |
|---|---|---|---|---|
| A35 | 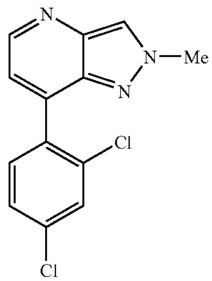 | 7-(2,4-Dichloro-phenyl)-2-methyl-2H-pyrazolo[4,3-b]pyridine | 160.5-162.8 | 278. (278) |
| A36 | 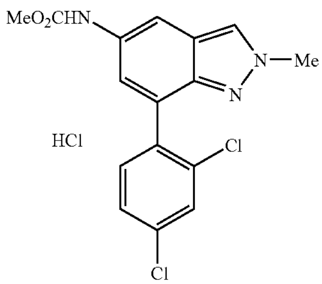 | [7-(2,4-Dichloro-phenyl)-2,3-dimethyl-2H-indazol-5-yl]-carbamic acid methyl ester; hydrochloride | | 364 (364) |

The compounds in Table B are carboxylic acid esters and amides prepared from 2-methyl-7-phenyl-2H-indazole-3-carboxylic acid (12a: E=CO$_2$H) or 2-methyl-7-bromo-2H-indazole-3-carboxylic acid (12b: E=CO$_2$H) in Scheme 4.

The carboxylic acids are prepared by quenching a 3-lihio compound with carbon dioxide. When the indazole compound is a 7-halo compound (e.g. 11b), deprotonation of the 3-position is accomplished with LDA to avoid concomitant transmetallation

TABLE B

| Cpd # | Structure | Name | mp ° C. | MH+ calcd (found) |
|---|---|---|---|---|
| B1 | 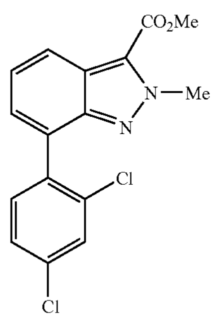 | 7-(2,4-Dichloro-phenyl)-2-methyl-2H-indazole-3-carboxylic acid methyl ester | 128-131 | 334 (334) |
| B2 | 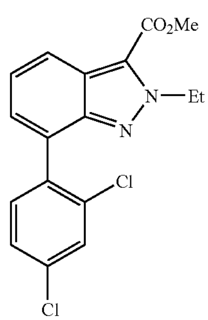 | 7-(2,4-Dichloro-phenyl)-2-ethyl-2H-indazole-3-carboxylic acid methyl ester | | 349 (349) |

TABLE B-continued

| Cpd # | Structure | Name | mp ° C. | MH+ calcd (found) |
|---|---|---|---|---|
| B3 | 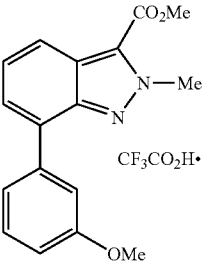 | 7-(3-Methoxy-phenyl)-2-methyl-2H-indazole-3-carboxylic acid methyl ester; compound with trifluoro-acetic acid | | 261 (261) |
| B4 | 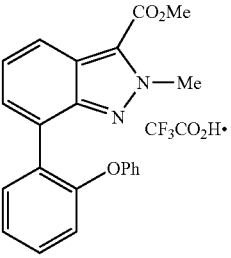 | 2-Methyl-7-(2-phenoxy-phenyl)-2H-indazole-3-carboxylic acid methyl ester; compound with trifluoro-acetic acid | | 359 (359) |
| B5 | 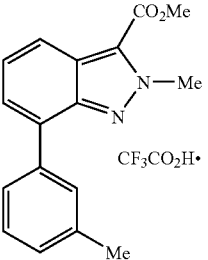 | 2-Methyl-7-m-tolyl-2H-indazole-3-carboxylic acid methyl ester; compound with trifluoro-acetic acid | | 281 (281) |
| B6 | 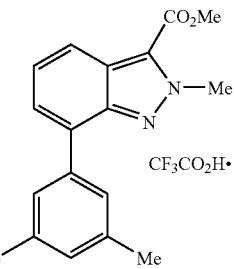 | 7-(3,5-Dimethyl-phenyl)-2-methyl-2H-indazole-3-carboxylic acid methyl ester; compound with trifluoro-acetic acid | | 295 (295) |
| B7 | 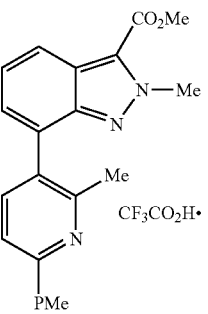 | 7-(4-Methoxy-2-methyl-pyridin-3-yl)-2-methyl-2H-indazole-3-carboxylic acid methyl ester; compound with trifluoro-acetic acid | | 312 (312) |

TABLE B-continued

| Cpd # | Structure | Name | mp ° C. | MH+ calcd (found) |
|---|---|---|---|---|
| B8 | 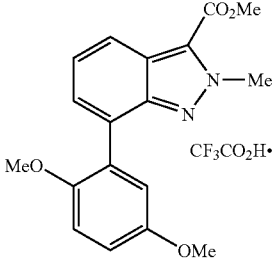 | 7-(2,5-Dimethoxy-phenyl)-2-methyl-2H-indazole-3-carboxylic acid methyl ester; compound with trifluoro-acetic acid | | 327 (327) |
| B9 | 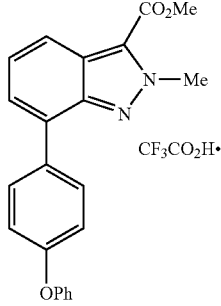 | 2-Methyl-7-(4-phenoxy-phenyl)-2H-indazole-3-carboxylic acid methyl ester; compound with trifluoro-acetic acid | | 359 (359) |
| B10 | 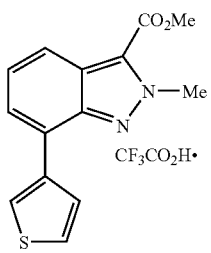 | 2-Methyl-7-thiophen-3-yl-2H-indazole-3-carboxylic acid methyl ester; compound with trifluoro-acetic acid | | 273 (273) |
| B11 | 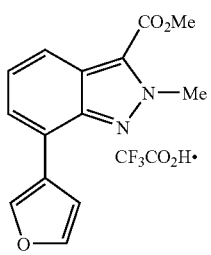 | 7-Furan-3-yl-2-methyl-2H-indazole-3-carboxylic acid methyl ester; compound with trifluoro-acetic acid | | 257 (257) |
| B12 | 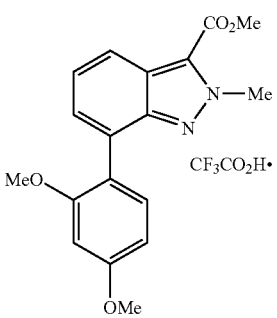 | 7-(2,4-Dimethoxy-phenyl)-2-methyl-2H-indazole-3-carboxylic acid methyl ester; compound with trifluoro-acetic acid | | 327 (327) |

TABLE B-continued

| Cpd # | Structure | Name | mp °C. | MH+ calcd (found) |
|---|---|---|---|---|
| B13 | 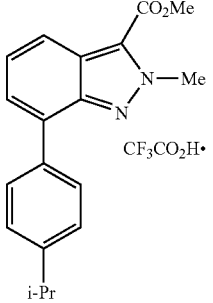 | 7-(4-Isopropyl-phenyl)-2-methyl-2H-indazole-3-carboxylic acid methyl ester; compound with trifluoro-acetic acid | | 309 (309) |
| B14 | 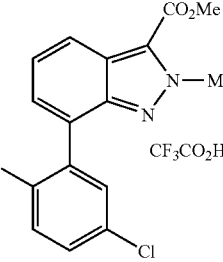 | 7-(2,5-Dichloro-phenyl)-2-methyl-2H-indazole-3-carboxylic acid methyl ester; compound with trifluoro-acetic acid | | 334 (334) |
| B15 | 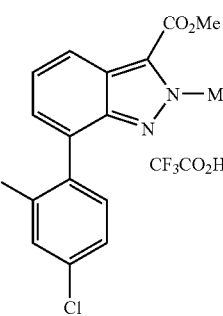 | 7-(2,4-Dichloro-phenyl)-2-methyl-2H-pyrazolo[3,4-c]pyridine; hydrochloride | 191-196 | 278 (278) |
| B16 | 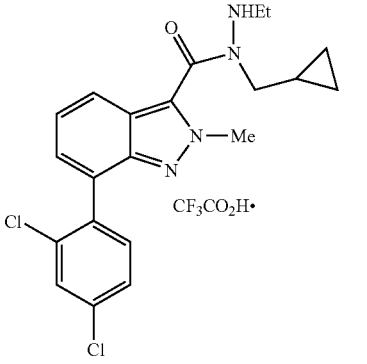 | 7-(2,4-Dichloro-phenyl)-2-methyl-2H-indazole-3-carboxylic acid N-cyclopropylmethyl-N'-ethyl-hydrazide; compound with trifluoro-acetic acid | | 417 (417) |

TABLE B-continued

| Cpd # | Structure | Name | mp ° C. | MH+ calcd (found) |
|---|---|---|---|---|
| B17 | 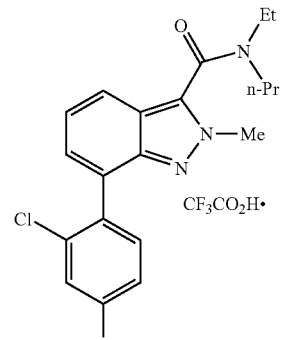 | 7-(2,4-Dichloro-phenyl)-2-methyl-2H-indazole-3-carboxylic acid ethyl-propyl-amide; compound with trifluoro-acetic acid | | 390 (390) |
| B18 | 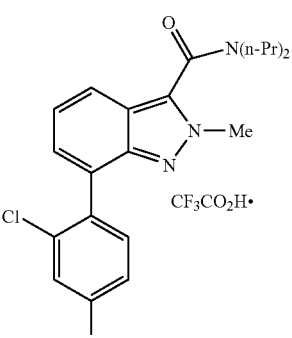 | 7-(2,4-Dichloro-phenyl)-2-methyl-2H-indazole-3-carboxylic acid dipropylamide; compound with trifluoro-acetic acid | | 404 (404) |
| B19 | 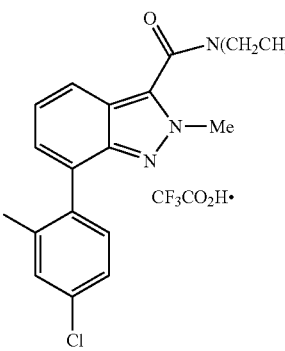 | 7-(2,4-Dichloro-phenyl)-2-methyl-2H-indazole-3-carboxylic acid bis-(2-methoxy-ethyl)-amide; compound with trifluoro-acetic acid | | 436 (436) |
| B20 | 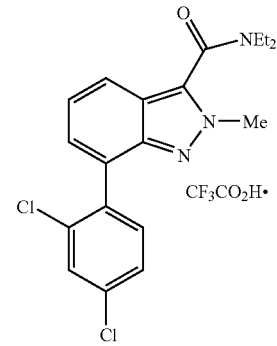 | 7-(2,4-Dichloro-phenyl)-2-methyl-2H-indazole-3-carboxylic acid diethylamide; compound with trifluoro-acetic acid | | 376 (376) |

TABLE B-continued

| Cpd # | Structure | Name | mp ° C. | MH+ calcd (found) |
|---|---|---|---|---|
| B21 | 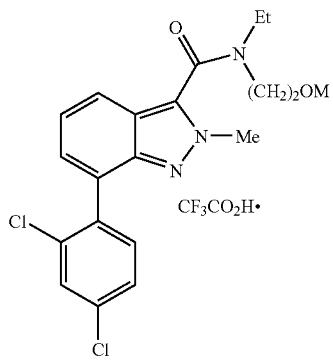 | 7-(2,4-Dichloro-phenyl)-2-methyl-2H-indazole-3-carboxylic acid ethyl-(2-methoxy-ethyl)-amide; compound with trifluoro-acetic acid | | 406 (406) |
| B22 | 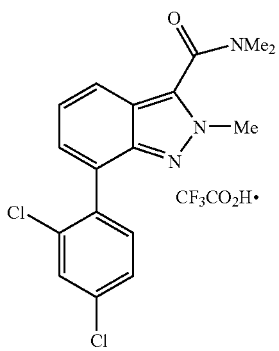 | 7-(2,4-Dichloro-phenyl)-2-methyl-2H-indazole-3-carboxylic acid dimethylamide; compound with trifluoro-acetic acid | | 348 (348) |
| B23 | 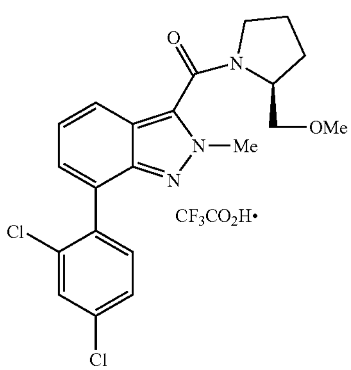 | [7-(2,4-Dichloro-phenyl)-2-methyl-2H-indazol-3-yl]-((S)-2-methoxymethyl-pyrrolidin-1-yl)-methanone; compound with trifluoro-acetic acid | | 418 (418) |
| B24 | 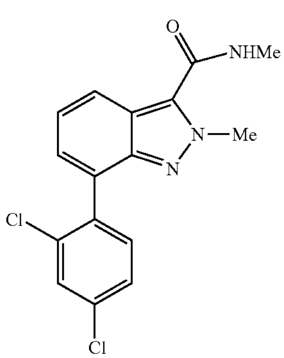 | 7-(2,4-Dichloro-phenyl)-2-methyl-2H-indazole-3-carboxylic acid methylamide | | 334 (334) |

TABLE B-continued

| Cpd # | Structure | Name | mp ° C. | MH+ calcd (found) |
|---|---|---|---|---|
| B25 | 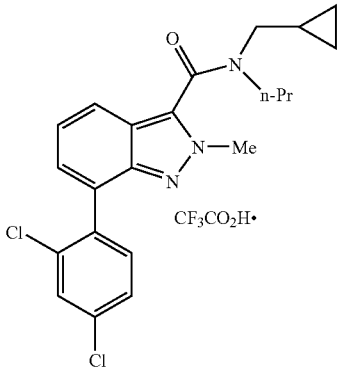 | Cyclopropylmethyl-[7-(2,4-dichloro-phenyl)-2-methyl-2H-indazol-3-ylmethyl]-propyl-amine; compound with trifluoro-acetic acid | | 402 (402) |
| B26 | 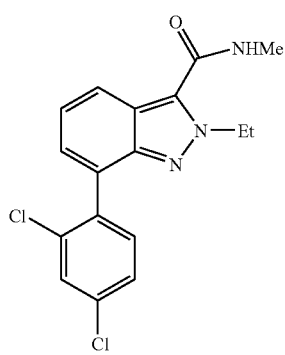 | 7-(2,4-Dichloro-phenyl)-2-ethyl-2H-indazole-3-carboxylic acid methylamide | | 348 (348) |

The compounds in Table C are (2-methyl-7-phenyl-2H-indazol-3-yl)-amine derivatives prepared from 2-methyl-7-phenyl-2H-indazol-3-ylamine as illustrated in Scheme 9. Also in Table C are [2-methyl-7-phenyl-2H-indazol-3-ylmethyl]-dimethyl-amine compounds.

TABLE C

| Cpd # | Structure | Name | mp ° C. | MH+ calcd (found) |
|---|---|---|---|---|
| C1 | 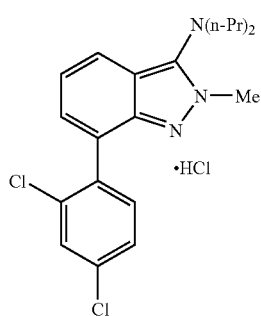 | [7-(2,4-Dichloro-phenyl)-2-methyl-2H-indazol-3-yl]-dipropyl-amine; hydrochloride | 139-140 | 376 (376) |

TABLE C-continued
| Cpd # | Structure | Name | mp ° C. | MH+ calcd (found) |
|---|---|---|---|---|
| C2 | 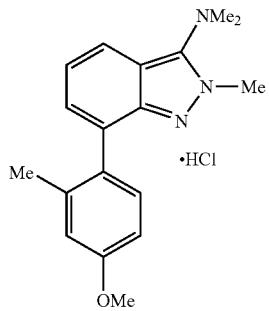 | [7-(4-Methoxy-2-methyl-phenyl)-2-methyl-2H-indazol-3-yl]-dimethyl-amine; hydrochloride | 166-167 | 296 (296) |
| C3 | 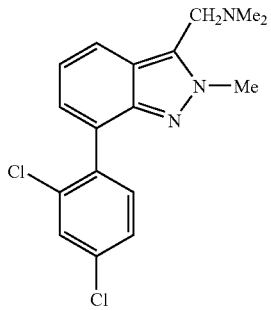 | [7-(2,4-Dichloro-phenyl)-2-methyl-2H-indazol-3-ylmethyl]-dimethyl-amine | | 334 (334) |
| C4 | 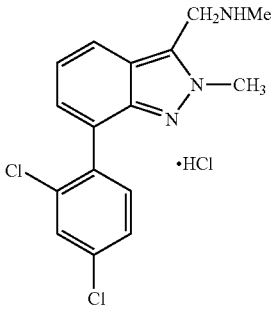 | [7-(2,4-Dichloro-phenyl)-2-methyl-2H-indazol-3-ylmethyl]-methyl-amine; hydrochloride | 211.1-213.0 | 320 (320) |
| C5 | 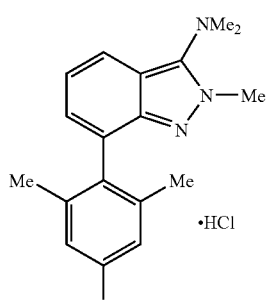 | Dimethyl-[2-methyl-7-(2,4,6-trimethyl-phenyl)-2H-indazol-3-yl]-amine; hydrochloride | 169.9-171.9 | 294 (294) |

TABLE C-continued

| Cpd # | Structure | Name | mp ° C. | MH+ calcd (found) |
|---|---|---|---|---|
| C6 | 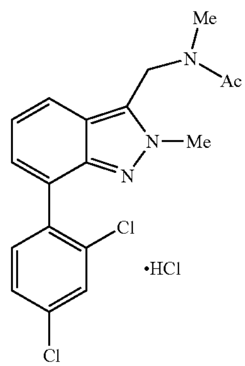 | N-[7-(2,4-Dichloro-phenyl)-2-methyl-2H-indazol-3-ylmethyl]-N-methyl-acetamide | 146.2-147.8 | 362 (362) |
| C7 | 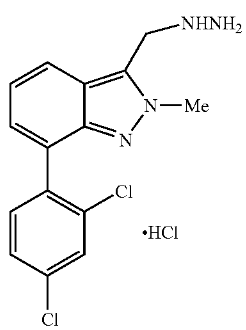 | [7-(2,4-Dichloro-phenyl)-2-methyl-2H-indazol-3-ylmethyl]-hydrazine; hydrochloride | 172.5-176 | 320 $M^+$ = (320) |
| C8 | 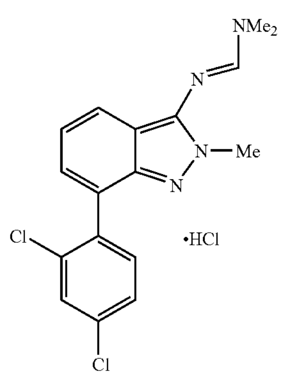 | N'-[7-(2,4-Dichloro-phenyl)-2-methyl-2H-indazol-3-yl]-N,N-dimethyl-formamidine; hydrochloride | | 347 (347) |
| C9 | 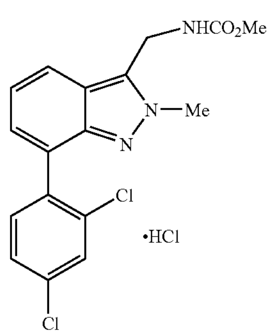 | [7-(2,4-Dichloro-phenyl)-2-methyl-2H-indazol-3-ylmethyl]-carbamic acid methyl ester; hydrochloride | 146.3-148.6 | 363 (364) |

TABLE C-continued

| Cpd # | Structure | Name | mp ° C. | MH+ calcd (found) |
|---|---|---|---|---|
| C10 | 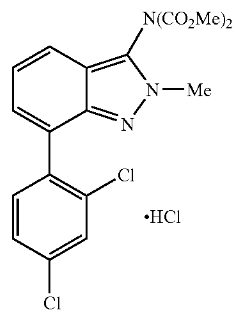 | Dimethoxycarbonylamino-[2-methyl-7-(2,4,6-trimethyl-phenyl)-2H-indazol-3-yl]-amine | | 408 (408) |
| C11 | 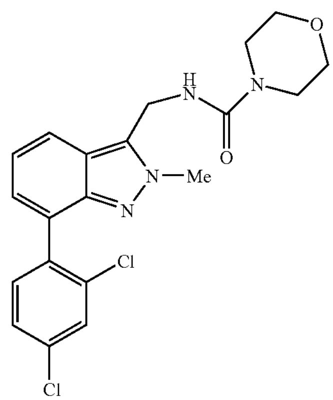 | Morpholine-4-carboxylic acid [7-(2,4-dichloro-phenyl)-2-methyl-2H-indazol-3-ylmethyl]-amide | 98.8-104.5 | 419 (419) |
| C12 | 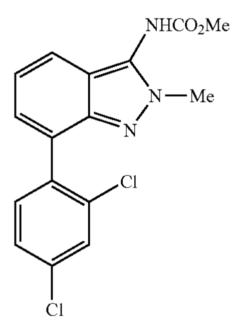 | [7-(2,4-Dichloro-phenyl)-2-methyl-2H-indazol-3-yl]-carbamic acid methyl ester | 219.0-293.3 | 350. (350) |
| C13 | 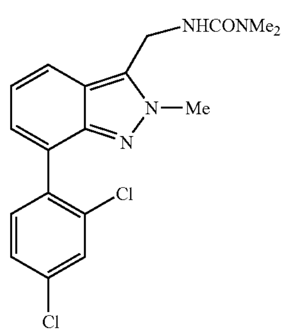 | 3-[7-(2,4-Dichloro-phenyl)-2-methyl-2H-indazol-3-ylmethyl]-1,1-dimethyl-urea | 101.9-105.1 | 377.27 (377) |

TABLE C-continued

| Cpd # | Structure | Name | mp ° C. | MH+ calcd (found) |
|---|---|---|---|---|
| C14 | 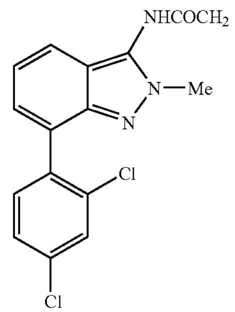 | [7-(2,4-Dichloro-phenyl)-2-methyl-2H-indazol-3-yl]-urea | >300 | 335 (335) |
| C15 | 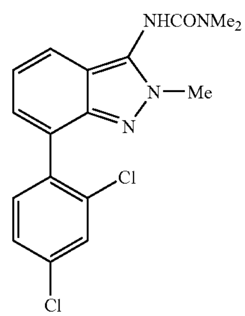 | 3-[7-(2,4-Dichloro-phenyl)-2-methyl-2H-indazol-3-yl]-1,1-dimethyl-urea | 123.3-126.3 | 363 (363) |

The compounds in Table D include sulfones and sulfonamides and precursors thereto.

TABLE D

| Cpd # | Structure | Name | mp ° C. | MH+ calcd (found) |
|---|---|---|---|---|
| D1 | 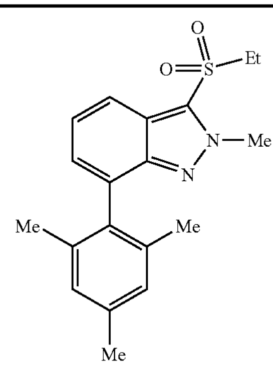 | 3-Ethanesulfonyl-2-methyl-7-(2,4,6-trimethyl-phenyl)-2H-indazole | | 343 (343) |
| D-2 | 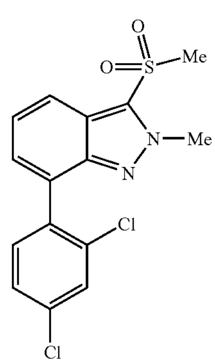 | 3-Methanesulfonyl-2-methyl-7-(2,4-dichloro-phenyl)-2H-indazole | 182.1-183.4 | 355.24 (355) |

TABLE D-continued

| Cpd # | Structure | Name | mp °C. | MH+ calcd (found) |
|---|---|---|---|---|
| D3 | 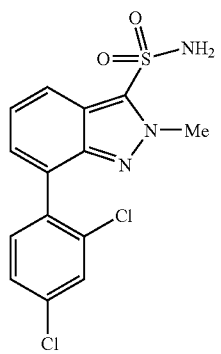 | 7-(2,4-Dichloro-phenyl)-2-methyl-2H-indazole-3-sulfonic acid amide | 170.7-173.6 | 356 (356) |
| D4 | 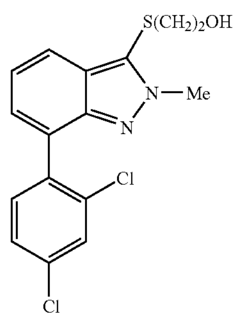 | 2-[7-(2,4-Dichloro-phenyl)-2-methyl-2H-indazol-3-ylsulfanyl]-ethanol | | 353. (353) |
| D5 | 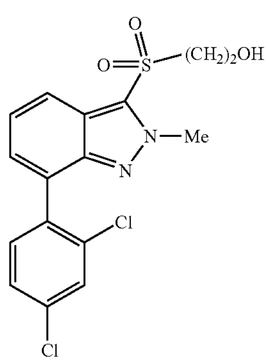 | 2-[7-(2,4-Dichloro-phenyl)-2-methyl-2H-indazole-3-sulfonyl]-ethanol | 157.8-161.7 | 385 (385) |
| D6 | 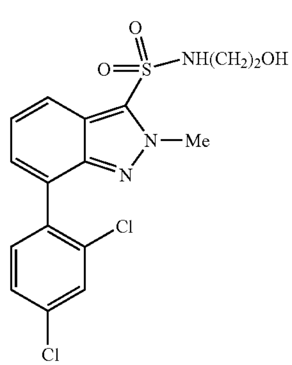 | 7-(2,4-Dichloro-phenyl)-2-methyl-2H-indazole-3-sulfonic acid (2-hydroxy-ethyl)-amide | | 400 (400) |

TABLE D-continued

| Cpd # | Structure | Name | mp ° C. | MH+ calcd (found) |
|---|---|---|---|---|
| D7 | 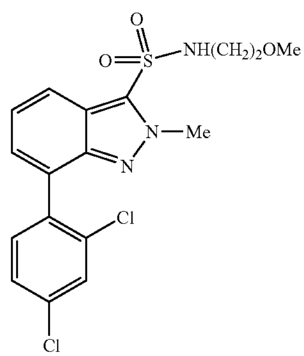 | 7-(2,4-Dichloro-phenyl)-2-methyl-2H-indazole-3-sulfonic acid (2-methoxy-ethyl)-amide | | 414. (414) |
| D8 | 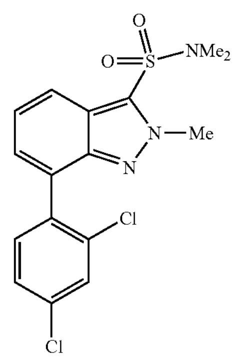 | 7-(2,4-Dichloro-phenyl)-2-methyl-2H-indazole-3-sulfonic acid dimethylamide | | 384 (384) |
| D9 | 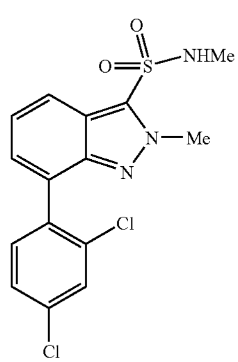 | 7-(2,4-Dichloro-phenyl)-2-methyl-2H-indazole-3-sulfonic acid methylamide | | 370 (370) |
| D10 | 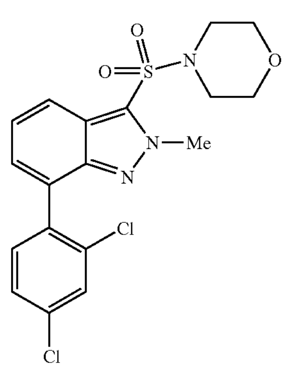 | 7-(2,4-Dichloro-phenyl)-2-methyl-3-(morpholine-4-sulfonyl)-2H-indazole | | 426. (426) |

TABLE D-continued

| Cpd # | Structure | Name | mp ° C. | MH+ calcd (found) |
|---|---|---|---|---|
| D11 | 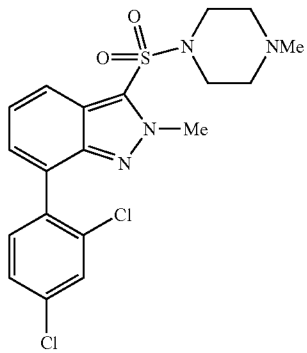 | 7-(2,4-Dichloro-phenyl)-2-methyl-3-(4-methyl-piperazine-1-sulfonyl)-2H-indazole | | 439 (439) |
| D12 | 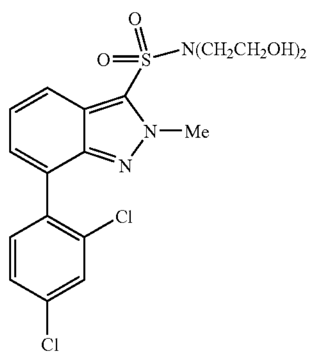 | 7-(2,4-Dichloro-phenyl)-2-methyl-2H-indazole-3-sulfonic acid bis-(2-hydroxy-ethyl)-amide | | 444 (444) |
| D13 | 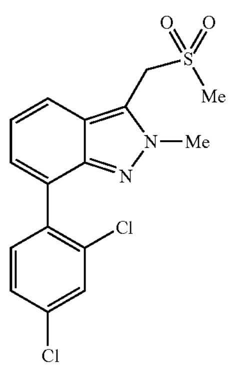 | 7-(2,4-Dichloro-phenyl)-3-methanesulfonylmethyl-2-methyl-2H-indazole | | 369. (369) |
| D14 | 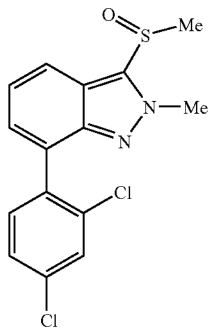 | 7-(2,4-Dichloro-phenyl)-3-methanesulfinyl-2-methyl-2H-indazole | | 339 (339) |

TABLE D-continued

| Cpd # | Structure | Name | mp °C. | MH+ calcd (found) |
|---|---|---|---|---|
| D15 | 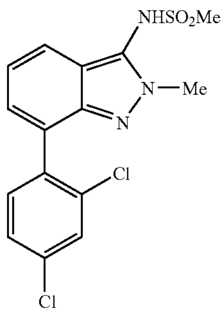 | N-[7-(2,4-Dichloro-phenyl)-2-methyl-2H-indazol-3-yl]-methanesulfonamide | 171.3-173.2 | 370 (370) |

Table E exemplifies 3-hydroxymethyl derivatives representative of compounds of the present invention. 3-Hydroxymethyl indazole compounds of the present invention were prepared by reacting a 3-lithioindazole with an aldehydes or ketone as depicted in Scheme 5. Alternatively a 3-carboxy derivative can be reduced with a suitable metal hydride to afford a hydroxylmethyl compound. Further transformations of the 3-hydroxymethyl compounds by standard methodology afford ethers, esters, carbamates which are encompassed in the present invention.

TABLE E

| Cpd # | Structure | Name | mp | MH+ calcd (found) |
|---|---|---|---|---|
| E1 | 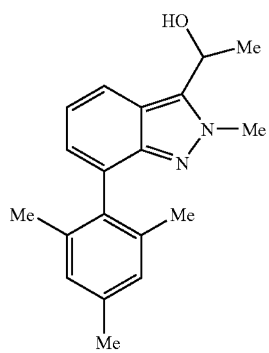 | 1-[2-Methyl-7-(2,4,6-trimethyl-phenyl)-2H-indazol-3-yl]-ethanol | 246-247 | 295 (295) |
| E2 | 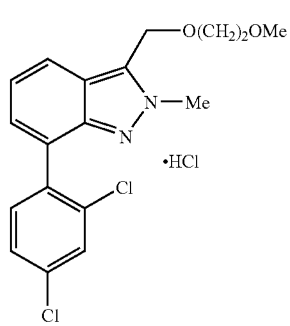 | 7-(2,4-Dichloro-phenyl)-3-(2-methoxy-ethoxymethyl)-2-methyl-2H-indazole | | 299 (299) |

TABLE E-continued

| Cpd # | Structure | Name | mp | MH+ calcd (found) |
|---|---|---|---|---|
| E3 | 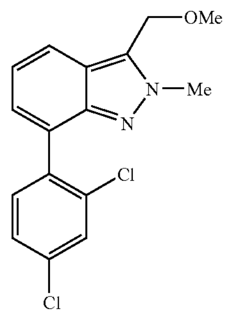 | 7-(2,4-Dichloro-phenyl)-3-methoxymethyl-2-methyl-2H-indazole | 119.0-120.9 | 321.21 (321) |
| E4 | 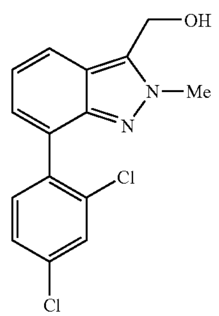 | 7-(2,4-Dichloro-phenyl)-2-methyl-2H-indazol-3-yl]-methanol | 197.3-201.2 | 307 (307) |
| E5 | 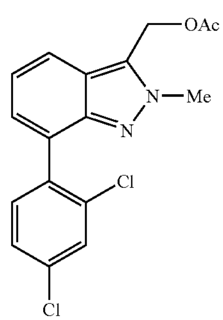 | Acetic acid [7-(2,4-dichloro-phenyl)-2-methyl-2H-indazol-3-yl]-methyl ester | 131.7-135.2 | 349. (349) |
| E6 | 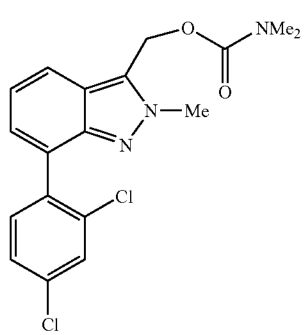 | Dimethyl-carbamic acid 7-(2,4-dichloro-phenyl)-2-methyl-2H-indazol-3-ylmethyl ester | 125.2-128 | 378 (378) |

TABLE E-continued

| Cpd # | Structure | Name | mp | MH+ calcd (found) |
|---|---|---|---|---|
| E7 | 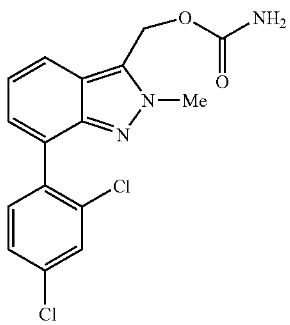 | Carbamic acid 7-(2,4-dichloro-phenyl)-2-methyl-2H-indazol-3-ylmethyl ester | 184.0-185.5 | 350.20 (350) |

Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

In particular, certain compounds of indazole compounds of formula I ($A^1$, $A^2$ and $A^3$ are CH or $CR^4$) may be prepared utilizing 7-bromoindazole (3) as an intermediate, the preparation of which is illustrated in Scheme 1 and described in Example 1. From (3) the compounds of formula I can be prepared by a three-step sequence including N-alkylation, palladium-catalyzed arylation at the 7-position and substitution of the 3-position by electrophilic substitution or deprotonation and quenching the resulting 3-lithioindazole. There is considerable flexibility in the sequence of these three operations which can be exploited to optimize the procedures for individual cases. Thus in sequence A, arylation at the 7-position is carried out prior to N-alkylation and

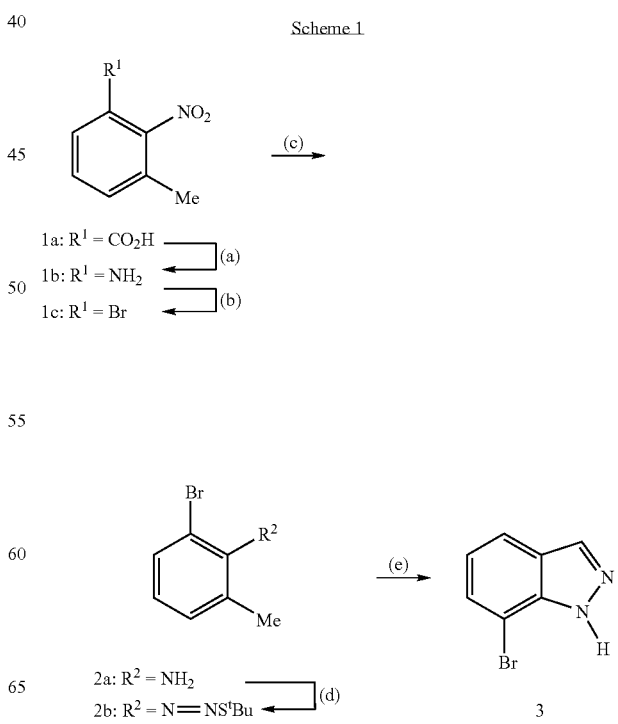

Scheme 1

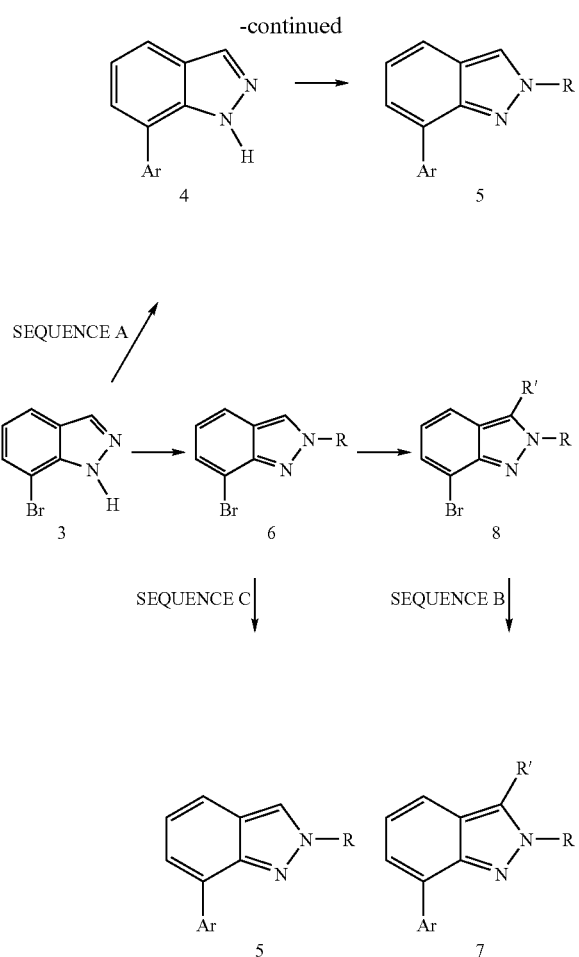

introduction of the substituent at the 3-position is carried out in the final step (Scheme 1; Example 2). The optimal procedure for a particular compound will generally be apparent by inspection and minimal experimentation is required. In another process (Scheme 1; Sequence B), N-alkylation and introduction of the substituent at the 3-position prior to the arylation step (see Example 3). Alternatively, the N-alkylation and arylation can be carried out initially prior to introduction of the 3-position (Scheme 1; Sequence C).

Aryl coupling procedures which can be used advantageously have been described: D. W. Knight *Coupling Reactions Between sp² Carbon Centers in Comprehensive Organic Synthesis*, vol. 3, G. Pattenden (Ed), Pergamon, Oxford. 1991 p 481-520. The Suzuki has been used extensively in preparation of compounds described herein. The Suzuki reaction [Equation (i)] is a palladium-catalyzed coupling of a boronic acid (R=aryl or vinyl) with an aryl or vinyl halide or triflate (R'=aryl or vinyl; Y=halide or —OSO₂CF₃). Typical catalysts include

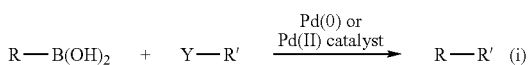

Pd(PPh₃)₃, Pd(OAc)₂ and PdCl₂(dppf). With PdCl₂(dppf), primary alkyl borane compounds can be coupled to aryl or vinyl halide or triflate without β-elimination. The reaction can be carried out in a variety of organic solvents including toluene, THF, dioxane, 1,2-dichloroethane, DMF, DMSO and acetonitrile, aqueous solvents and under biphasic conditions. Reactions are typically run from about room temperature to about 150° C. Additives (e.g. CsF, KF, TlOH, NaOEt and KOH) frequently accelerate the coupling. Although there are numerous components in the Suzuki reaction including the palladium source, the ligand, additive solvent, temperature, etc., numerous protocols have been identified. Highly active catalysts have been identified (see, e.g. J. P. Wolfe et al., *J. Am. Chem. Soc.* 1999 121(41):9550-9561 and A. F. Littke et al., *J. Am. Chem. Soc.* 2000 122(17):4020-4028). One skilled in the art will be able to identify a satisfactory protocol without undue experimentation.

Deprotonation of the 3-position of the 7-aryl-2-alkyl-indazole (5) or the 7-bromo-2-alkyl-indazole compound (6) was achieved with LDA in THF at −78° C. (Scheme 1). The deprotonation of indazoles can also be accomplished with BuLi in THF at −78° C. The latter conditions were acceptable with the trialkylphenyl substituents; however some 7-substituted phenyl indazoles are subject to deprotonation or transmetalation of the 7-aryl substituent when the deprotonation was carried out with n-BuLi. One skilled in the art will readily identify acceptable deprotonation conditions without undue experimentation.

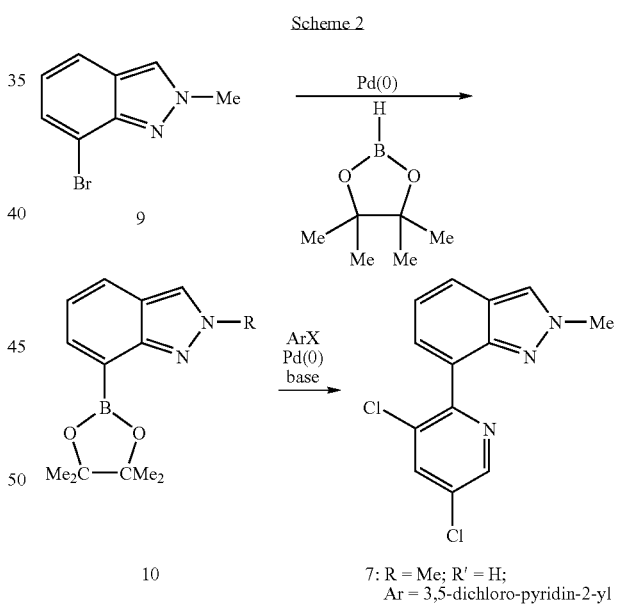

Other embodiments of the invention are more efficiently prepared by introducing a boronic acid derivative at the 7-position of the indazole and coupling 10 with an aryl halide (Example 2). Cross-coupling of aryl halides and aryl triflates and pinacolborane have been used effectively to prepare intermediates for aryl coupling. (T. Ishiyama et al., *Tetrahedron Lett.* 1997 38:3447-3450; A. Wolan and M. Zaidlewicz, *Org. Biomol. Chem.* 2003 1:3274-3276; M. Brimble and M. Y. H. Lai, *Org. Biomol. Chem.* 2003 1:2084-2095)

Scheme 3

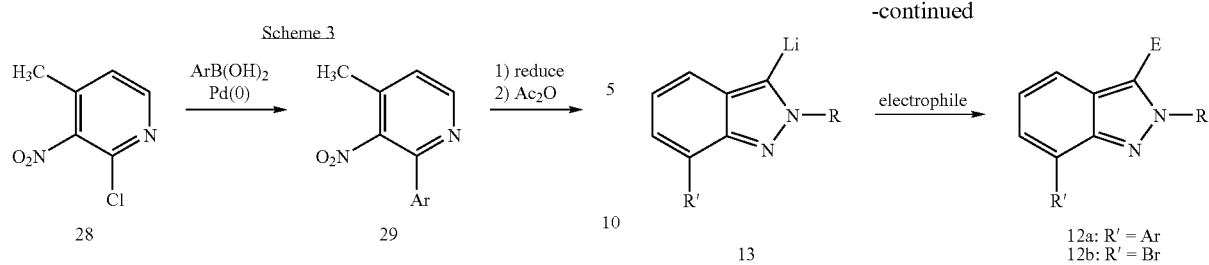

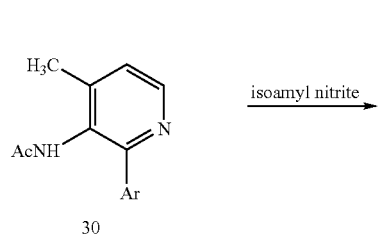

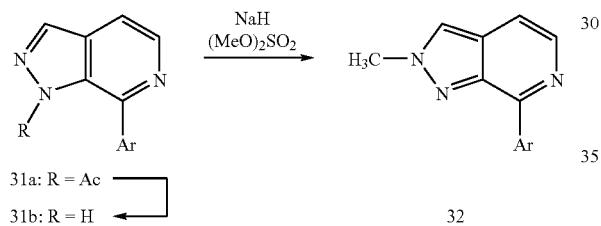

2H-Pyrazolopyridines are prepared from pyridines substituted by a methyl group and an acetamido group at adjacent positions. 2-Chloro-3-nitro-4-methylpyridine (28) was subjected to palladium-mediated coupling of an aryl boronic acid to afford the corresponding 2-arylpyridine (29). After reduction of the nitro to an amine and acetylation, the acetamide was treated with isoamyl nitrite, potassium acetate and acetic anhydride. The intermediate N-nitroso compound cyclizes under the reaction conditions to an acetylated pyrazolopyridine 31a which is hydrolyzed to 31b (P. Marakos et al. *Synth Lett.* 1997 561-62; D. Chapman and J. Hurst, *J. Chem. Soc. Perk. I* 1980 2398). N-alkylation of the 2-position and elaboration of the 3-position proceeds as described for the indazoles. Similar procedures can be adapted to other pyrazolopyridines.

Scheme 4

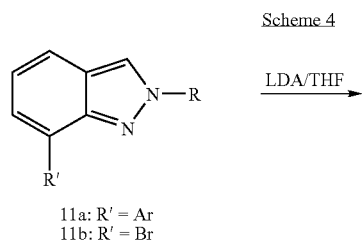

Substitution at the three position is achieved by electrophilic substitution or by deprotonation of the 3-position with strong base. The 3-lithio-7-arylindazole 13 can be reacted with a variety of electrophiles such as alkyl halides (e.g., MeI, E=Me; 2-methoxyethoxymethyl chloride, E=CH$_2$O(CH$_2$)$_2$OMe), alkenyl halides (e.g., allyl bromide, E=allyl), alkynyl halides (e.g., bromopropyne, E=propargyl), aldehydes (e.g., acetaldehyde, E=CH(OH)R), ketones (e.g., acetone, E=C(OH)R'R''), amides (e.g., MeC(=O)N(Me)OMe, E=C(=O)Me; DMF, E=CHO), disulfides (e.g., EtS-SEt, E=SEt) and carbon dioxide (e.g., E=COOH) to produce 3-substituted indazoles.

Scheme 5

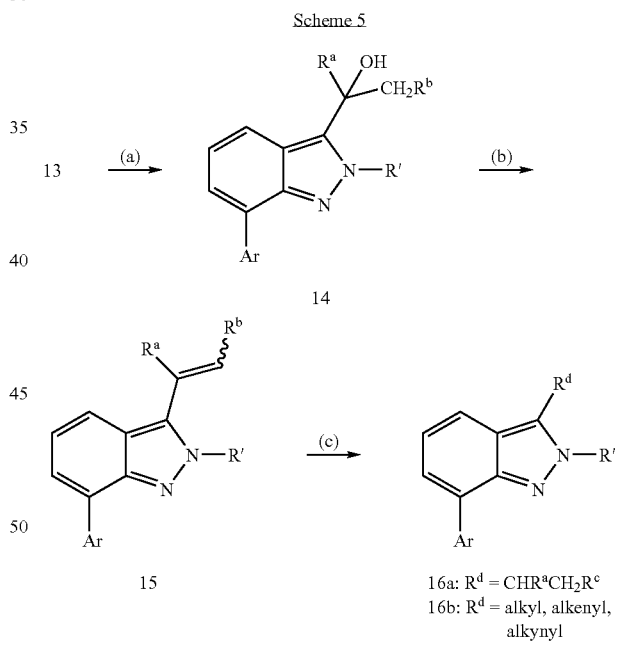

R, R$^a$, R$^b$ R$^c$ = H, alkyl, R' = alkyl; Ar = (substituted) aryl
(a) RC(=O)R'; (b) p-TsOH, PhCH$_3$; (c) H$_2$, Pd/C Embodiments of the present invention include, alkyl alkenyl, alkynyl and hydroxyalkyl substituents. Many of these groups can be directly introduced by reacting the desired substituent with an appropriate leaving group on the atom to be attached to the indazole with the lithiated indazole (Scheme 4) 1-Alkenyl substitution at the 3-position is introduced by a two step sequence wherein an aldehyde or ketone is reacted with 13 to afford a carbinol 14 which can be dehydrated to an olefin. Dehydration generally affords a mixture of E and Z olefins; the present invention includes both the pure E and Z isomers and mixtures thereof. The olefins optionally can be further converted to the corresponding alkane 16a by catalytic hydrogenation.

Scheme 6

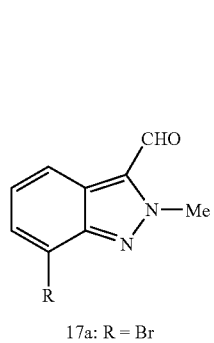

17a: R = Br
17b: R = Ar

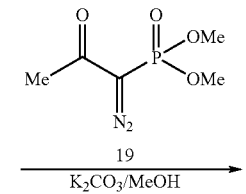

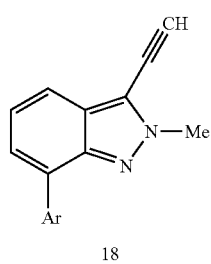

18

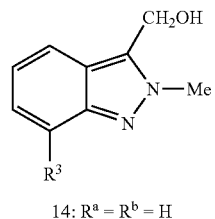 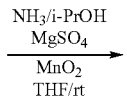 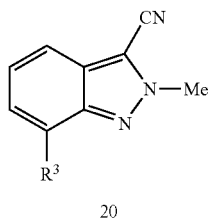

14: $R^a = R^b = H$     20

Similarly whereas 3-alkyn-[n]-yl groups wherein n>2 can be introduced directly by reaction of an alkynyl compound with a suitable leaving group. The 3-ethynyl group is introduced by condensation of (1-diazo-2-oxo-propyl)-phosphonic acid dimethyl ester (19; S. Müller et al., *Syn Lett.* 1996 (6):521-22) with 3-formyl-7-arylindazole (17). 3-Formyl-7-bromoindazole was prepared by condensation of 3-lithio-7-bromoindazole with DMF followed by palladium catalyzed introduction of the aryl substituent. An olefin (e.g., 15: $R^a$=H, $R^c$=alkyl) can be converted to an acetylene by bromination and dehydrohalogenation (J. March *Advanced Organic Chemistry* 4$^{th}$ Ed J Wiley & Sons: New York, 1991; pp 1023-1024). Alternatively, the ethynyl compound 18 can be deprotonated and alkylated (J. March, supra, p. 481). The 3-hydroxymethyl-2-methyl-7-arylindazole (4: $R^a=R^a$=H) was converted to the corresponding 3-cyano a derivative by a tandem oxidation-imination-oxidation sequence (G. D. McAllister, *Syn Lett* 2002 (8):1291-92).

3-Halo-substituted indazoles can be obtained by direct electrophilic substitution of the unsubstituted indazole with a brominating or chlorinating reagent. The preparation of 3-halo compounds is illustrated in scheme 7.

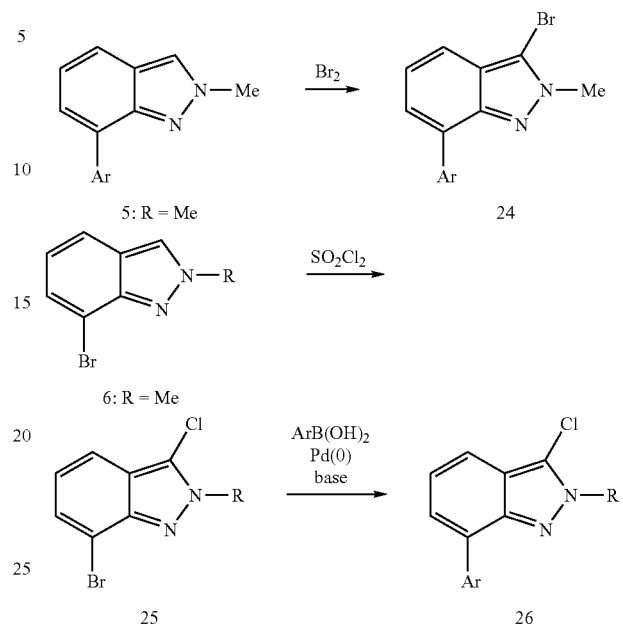

The present invention further includes 3-alkoxycarbonyl-indazoles (34: X=OR) and 3-carbamoyl-indazole (22: X=$NH_2$, NHR' or NR'R") compounds (Table B) prepared by

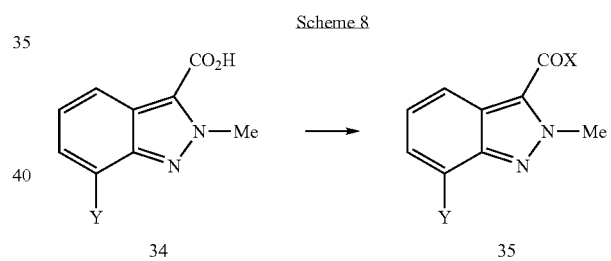

Y = Br or (substituted)aryl
X = OR, NH2, NHR', NR'R"
R, R', R" = alkyl, aralkyl, aryl, cycloalkyl condensation of an activated carboxylic acid derivative with alcohols, ammonia, primary and secondary amines. The carboxylic acid 34 is prepared by contacting 13 with $CO_2$. An "activated carboxylic acid derivative" or "activated 3-carboxy-indazole" refers to a stable reactive derivative (e.g., acyl chloride or acyl bromide or (mixed) anhydride) or a transient reactive form of a carboxylic acid (e.g. a dialkylisouronium salt formed by condensation with a N,N'-dialkyldiimide) which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. Acylation of alcohols (J. March, *Advanced Organic Chemistry* John Wiley & Sons, New York 1992 392-398; J. Mulzer *Synthesis of Esters, Activated Esters & Lactones in Comprehensive Organic Synthesis*, E. Winterfeldt, ed., vol. 6, Pergamon Press, Oxford 1991, pp. 324-340) and amines (J. March, supra pp. 417-425; H. G. Benz, *Synthesis of Amides and Related Compounds in Comprehensive Organic Synthesis*, E. Winterfeldt, ed., vol. 6, Pergamon Press, Oxford 1991 pp. 381-411) have been reviewed. Alternatively, a carboxylic ester, prepared as described above, can be converted to an amide by treatment with a suitable amine. The formation on an amide is accelerated by the presence of a Lewis Acid (e.g., $Me_3Al$)

as molecular sieve or $Ti(IV)(O-i-Pr)_4$ to facilitate formation of the intermediate imine at ambient temperature or with hydrogen in the presence of a hydrogenation catalyst, e.g. in the presence of palladium/charcoal, at a hydrogen pressure of 1 to 5 bar, preferably at temperatures between 20° C. and the boiling temperature of the solvent used. It may also be advantageous during the reaction if reactive groups are protected during the reaction by conventional protecting

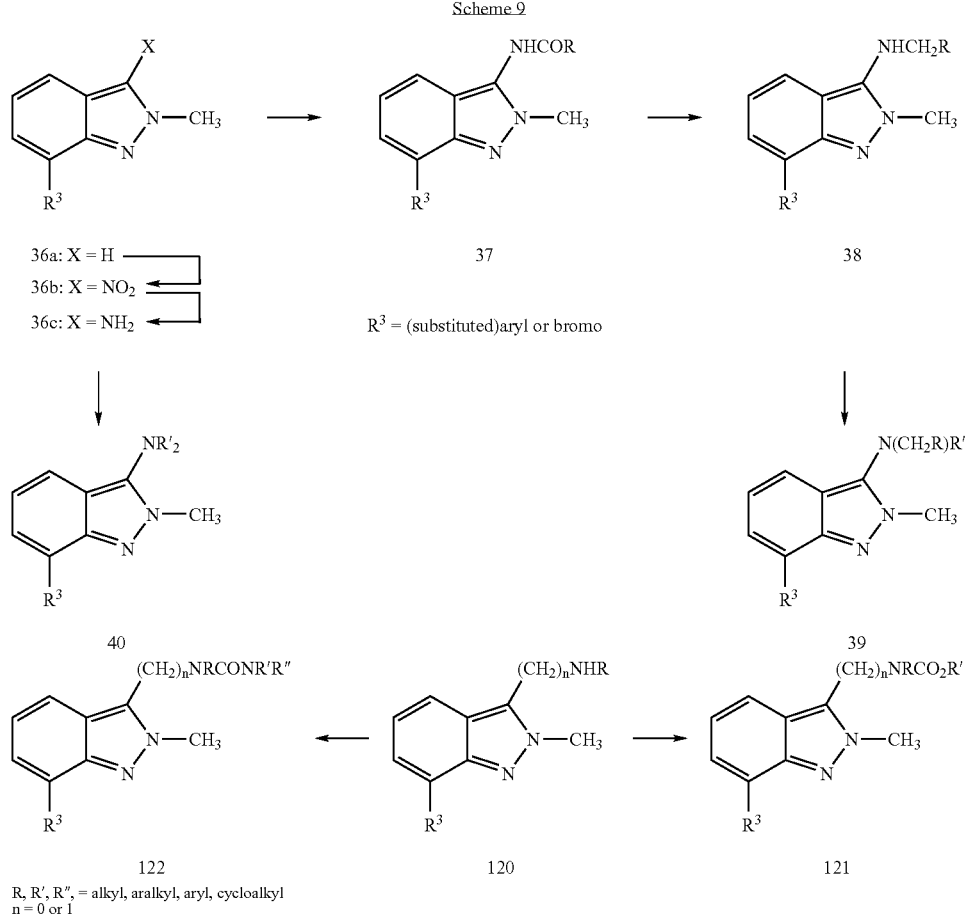

Scheme 9

$R^3$ = (substituted)aryl or bromo

R, R', R", = alkyl, aralkyl, aryl, cycloalkyl
n = 0 or 1

Conversion of amine such as 36c into amides can be achieved by a variety of methodologies (supra). Reduction of the amide 37 with borane-THF complex, or other reducing agents, (J. March supra, pp 445-446; A. G. M. *Barrett Reduction of Carboxylic Acid Derivatives to Alcohols, Ethers and Amines in Comprehensive Organic Synthesis* vol. 8, I. Fleming (Ed) 1991 248-251) affords the secondary amine 38 that can be further transformed to the tertiary amine 39 by reductive amination or via a second acylation and reduction sequence. The process allows for the introduction of two different alkyl groups on to an amine. When a tertiary amine with two identical alkyl groups is desired reductive amination can be used (Scheme 8). Reductive amination is preferably carried out by combining an amine and carbonyl compound in the presence of a complex metal hydride such as sodium borohydride, lithium borohydride, sodium cyanoborohydride, zinc borohydride, sodium triacetoxyborohydride or borane/pyridine conveniently at a pH of 1-7 optionally in the presence of a dehydrating agent such groups which are cleaved again by conventional methods after the reaction. Reductive amination procedures have been reviewed: R. M. Hutchings and M. K. Hutchings *Reduction of C=N to CHNH by Metal Hydrides* in *Comprehensive Organic Synthesis* col. 8, I. Fleming (Ed) Pergamon, Oxford 1991 pp. 47-54.

Amines C3 and C4 are prepared by metal hydride reduction of a carboxamide compound 35 (X=NH-alkyl or N(alkyl)$_2$). 3-Aminomethyl compounds can also be prepared from 3-formyl compounds by reductive amination. Acylation of 3-amino and 3-aminomethyl compounds can be accomplished as described above.

Carbamates 121 and ureas 122 are prepared by acylation a 3-amino (40, R=H) or 3-aminomethyl compound (120, n=1) with an alkoxychloroformate, a alkylaminocarbonyl chloride or related derivatives well-known in the art. Acylation with an alkoxychloroformate (e.g., ethoxychloroformate) or aryloxy chloroformate affords carbonate compounds (3: Y=O-alkyl or —O-aryl). Carbonates are formally diesters of carbonic acid and are accessible from phosgene or its equivalents. Typically phosgene is introduced into a reaction mixture at low temperature containing an alcohol and base. N,N-dialkylamines or quaternary ammonium salts catalyze the reaction. The reaction can be stopped at the intermediate alkoxy chloroformate stage. The alkoxy chloroformate can then be used to make unsymmetrical carbonate esters. Condensation of alkoxychloroformates are carried out in a solvent such as methylene chloride, chloroform, carbon tetrachloride, ether, tetrahydrofuran, dioxane, benzene, toluene, acetonitrile, dimethylformamide, optionally in the presence of an inorganic or organic base (e.g., triethylamine or pyridine) at temperatures between −20 and 200° C., but preferably at temperatures between −10 and 80° C. Alternatives to the toxic gaseous phosgene include trichloromethylchloroformate (diphosgene) and bis-(trichloromethyl)carbonate (triphosgene) (H. Eckert and A. Nestl, *Functions Containing a Carbonyl Group and at least one Chalcogen (but no Halogen)* in *Comprehensive Organic Functional Group Transformations*, B. Trost (ed) Vol 6, E. Winterfeldt (volume editor) Pergamon Press Oxford, UK, 1995, pp 460-462; J. March, *Advanced Organic Chemistry*, John Wiley & Sons, NY, 1992 p. 392) Acylation with alkylaminocarbonyl chloride, (hetero)arylaminocarbonyl chloride, or with the correspond isocyanates, affords carbamate compounds (H. Eckert and A. Nestl, supra, pp. 484-485).

pounds 22. Oxidation with one or two equivalents of MCPBA or equivalent oxidizing agent affords the sulfoxide (23, n=1) or the sulfone (23: n=2) respectively (Scheme 10). Sulfonyl chlorides 123 are prepared by oxidizing the thiobenzyl ether (22, R=Me, R'=CH₂Ph) to a sulfonyl chloride (Th. Zincke and H. Rose, *Ann.* 1914 406:127; R. H. Baker et al., *J. Am. Chem. Soc.* 1946 68:2636-2639). Alternatively a sulfonyl chloride can be prepared by direct sulfonylation of an indazole with trimethylsilyl chlorosulfonate and treating the resulting sulfonic acid with thionyl chloride and a catalytic quantity of DMF. Sulfonamides are prepared by condensing the sulfonyl chloride with a (di) alkylamine. The unsubstituted sulfonamide (125, $R^j=R^k=H$) were prepared by reduction of a sulfonyl azide. 3-(Alkyl) aminosulfonamides (127) were prepared in analogous manner from 3-aminoindazoles (126).

Dosage and Administration

The compounds of the present invention may be formulated in a wide variety of oral administration dosage forms and carriers. The pharmaceutically acceptable carriers may be either solid or liquid. Oral administration can be in the form of tablets, coated tablets, dragees, hard and soft gelatin capsules, solutions, emulsions, syrups, or suspensions. Compounds of the present invention are efficacious when admin-

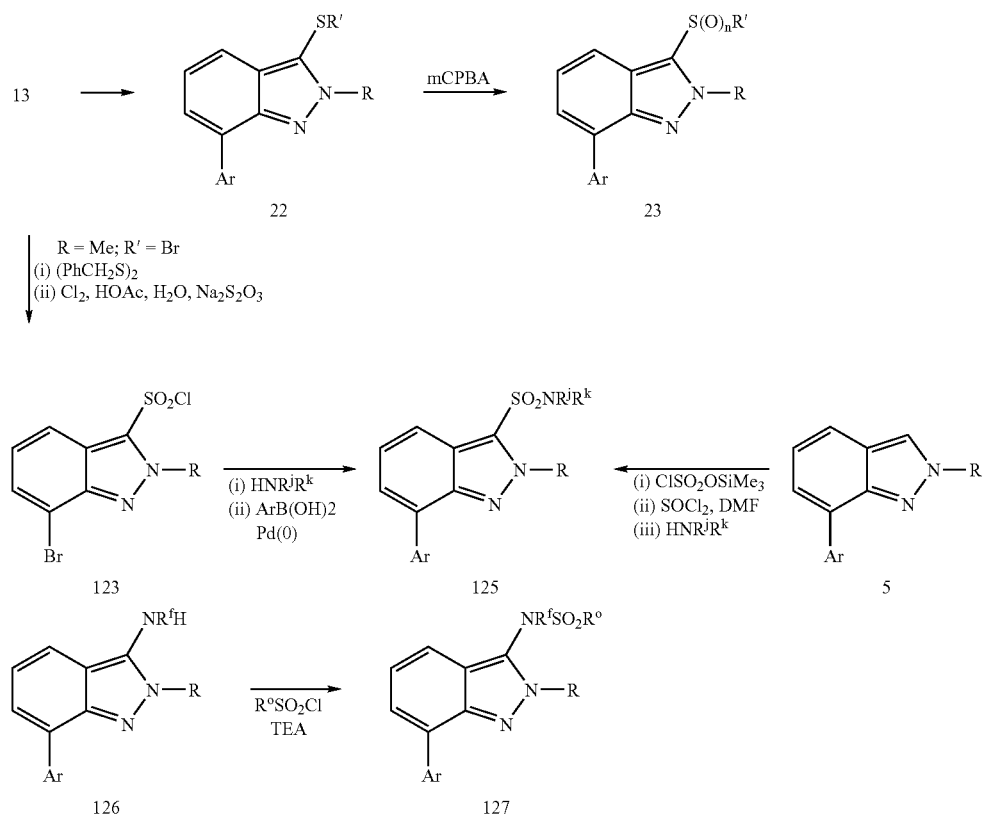

3-Alkylthio-, 3-alkylsulfinyl- and 3-alkylsulfonyl substituted indazoles are prepared by contacting the 3-lithioindazole with disulfides which affords 3-alkylthio comistered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w).

The term "excipient" as used herein refers to a compound that is useful in preparing a pharmaceutical composition, generally safe, non-toxic and neither biologically nor otherwise undesirable, and includes excipients that are acceptable for veterinary use as well as human-pharmaceutical use. The term "excipient" as used herein includes both one and more than one such excipient.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The term "preparation" or "dosage form" as used herein is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Liquid formulations also are suitable for oral administration include liquid formulation including emulsions, syrups, elixirs, aqueous solutions, aqueous suspensions are also suitable forms for oral administration. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the fatter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and expcipients are described in *Remington: The Science and Practice of pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions in Example 21 are given to enable those skilled in the art to more clearly understand and to practice the present invention. They should not be considered as limiting the scope of the invention, but merely as being illustrative and representative thereof.

Example 1

7-Bromo-2H-indazole

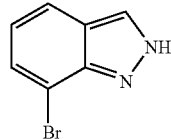

(3)

Step 1

3-Bromo-2-nitrotoluene (Scheme 1; 1c)—A mixture of copper(II) bromide (3.52 g, 15.7 mol) in 20 mL dry acetonitrile was heated to 65° C. under an $N_2$ atmosphere. t-Butyl nitrite (2.35 mL, 2.03 g, 19.7 mmol) was added all at once. A solution of 3-methyl-2-nitroaniline (1b; 2.00 g, 13.1 mmol; *J Org Chem.* 1976 41(21):3357) in 15 mL acetonitrile was added to the above solution at a rate to sufficient to maintain gentle reflux. After addition the mixture was heated at a gentle reflux for an additional 15 m. The reaction mixture was cooled to rt and partitioned between 6N HCl solution (150 mL) and ether (150 mL). The ethereal solution was separated and washed with brine, then dried over $MgSO_4$. Evaporation of the solvent afforded 2.76 g of impure material, which was flash chromatographed on $SiO_2$ and eluted with 10% acetone in hexane which afforded 1.62 g (57%) of 1c as a pale yellow-green liquid.

Step 2

2-Bromo-6-methylaniline (2a)—A mixture of tellurium (21.6 g, 169.4 mmol) and NaBH$_4$ (15.0 g, 396 mmol) in 575 mL of absolute EtOH was heated at reflux under an atmosphere of N$_2$ for 1 hr, then allowed to cool to rt. A solution of 3-bromo-2-nitrotoluene (1c; 7.32 g, 33.8 mmol) in 25 mL EtOH was added all at once and the mixture allowed to stir at room temperature for 2 hrs. The reaction mixture was filtered through a CELITE® pad and the filtrate evaporated under reduced pressure. The residue was taken up in Et$_2$O (about 200 mL), washed with brine then dried over MgSO$_4$. Evaporation of the solvent afforded 2.66 g (42%) of 2a as a dark liquid.

Step 3

(2-Bromo-6-methylphenlazo)-t-butylsulfide (2b)—2-Bromo-6-methylaniline (2a; 1.18 g, 6.34 mmol) and 3.4 mL 6N HCl was heated in an oil bath at 60° for 30 m, then cooled to 0°. A solution of NaNO$_2$ (481 mg, 6.97 mmol) in 1.5 mL H$_2$O was added dropwise then stirred in the cold for an additional hr. The reaction mixture was buffered to a pH between 4 and 5 with saturated NaOAc solution, then added all at once to an ice-cold solution of t-butyl mercaptan (0.80 mL, 629 mg, 6.97 mmol) in 14 mL EtOH. The mixture was allowed to warm to rt overnight. The reaction mixture was partitioned between EtOAc (50 mL) and H$_2$O (50 mL). The aqueous layer was re-extracted with EtOAc (50 mL). The combined EtOAc extracts were washed with brine and dried over MgSO$_4$. Evaporation of the solvent afforded 1.46 g (80%) of 2b.

Step 4

7-Bromoindazole (3)—A solution of (2-bromo-6-methylphenylazo)-t-butylsulfide (2b; 880 mg, 3.06 mmol) in 10 mL dry DMSO was added dropwise to a solution of potassium t-butoxide (3.44 g, 30.6 mmol) in 25 mL dry DMSO under Ar. The reaction mixture was stirred at room temperature for 2 hr, then poured into 150 g ice and 150 mL 2 N HCl solution. The mixture was extracted with ether (2×150 mL). The combined ethereal extracts were washed with brine and dried over MgSO$_4$. Evaporation of the solvent afforded 581 mg (96%) of 3 as a beige solid.

Example 2

7-(2,4-Dichloro-phenyl)-2-methyl-2H-indazole

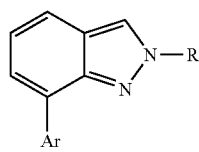

5 (Ar=2,4-dichlorophenyl; R=Me)

Step 1

A solution of 7-bromo-1H-indazole (3; 1.01 g, 5.13 mmol) and tetrakis(triphenylphosphine) palladium(0) (0.176 g, 0.152 mmol) in 15 mL of ethylene glycol dimethyl ether was stirred for 30 m. To the solution was added 2,4-dichlorophenyl boronic acid (1.93 g, 10.1 mmol) and a 2 M aqueous Na$_2$CO$_3$ solution (7.1 mL, 14.2 mmol). The orange-yellow mixture was stirred at 80° C. for 19 h, allowed to cool, then partitioned between 50 mL of ethyl acetate and 50 mL of water. The organic layer was dried over MgSO$_4$, filtered, and concentrated to an orange oil. Column chromatography (0→10% EtOAc/hexanes) afforded of 7-(2,4-dichloro-phenyl)-1H-indazole as a pale yellow foamy solid (4; 1.12 g, 83%).

Step 2

A solution of 7-(2,4-dichloro-phenyl)-1H-indazole (4; 1.12 g, 4.27 mmol) and dimethyl sulfate (0.405 mL, 4.28 mmol) in 15 mL of toluene was stirred at 110° C. for 17 h, allowed to cool, then chilled at 0-5° C. The mixture was carefully washed with 15 mL of a saturated aqueous NaHCO$_3$ solution, dried over MgSO$_4$, filtered (rinsing with diethyl ether), and concentrated to an orange oil Column chromatography (0→33% EtOAc/hexanes) afforded 7-(2,4-dichloro-phenyl)-2-methyl-2H-indazole as a viscous yellow oil (5; 0.92 g, 78%).

Step 3—Hydrochloride Salt

To a solution of 7-(2,4-dichloro-phenyl)-2-methyl-2H-indazole (5; 0.056 g, 0.20 mmol) in 2 mL of diethyl ether was added 0.2 mL of a 2.0 M solution of HCl in ether. The resulting mixture was stirred for 30 m and filtered to afford 0.041 g (65%) of 7-(2,4-dichloro-phenyl)-2-methyl-2H-indazole; hydrochloride: m.p. 133-147.

The following compounds were prepared in a similar fashion as for 7-(2,4-Dichloro-phenyl)-2-methyl-2H-indazole and purified by reverse-phase HPLC:

7-(2,4-Dichloro-phenyl)-2-ethyl-2H-indazole; compound with trifluoro-acetic acid 2-Benzyl-7-(2,4-Dichloro-phenyl)-2-2H-indazole, compound with trifluoroacetate;

[7-(2,4-Dichloro-phenyl)-indazol-2-yl]-acetic acid ethyl ester; compound with trifluoro-acetic acid Example 3

7-(2,4-Dichloro-phenyl)-2,3-dimethyl-2H-indazole; hydrochloride

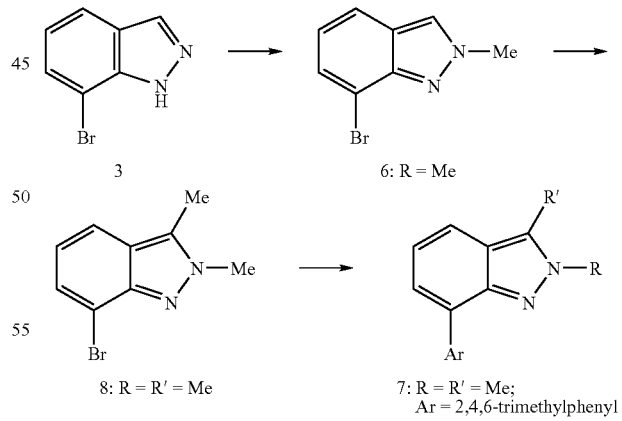

Step 1

A solution of 7-bromo-1H-indazole (3; 1.71 g, 8.67 mmol) and dimethyl sulfate (0.90 mL, 9.5 mmol) in 30 mL of toluene was stirred at 110° C. for 4 h, then allowed to cool. The mixture was carefully washed with 30 mL of a saturated aqueous NaHCO$_3$ solution, dried over MgSO$_4$, filtered (rinsing with diethyl ether), and concentrated to an orange oil Column chromatography (0→50% EtOAc/hexanes) afforded 7-bromo-2-methyl-2H-indazole (6: R=Me; 1.33 g, 73%) as a light tan solid.

Step 2

To a solution of 7-bromo-2-methyl-2H-indazole (5.49 g, 26.0 mmol) in 100 mL of THF at −78° C. was added a 2.0 M solution of lithium diisopropylamide in THF/heptane/ethylbenzene (19.5 mL, 39.0 mmol). The resulting dark orange solution was stirred at 0-5° C. for 15 m, then rechilled at −78° C. for 15 m. Iodomethane (2.5 mL, 40 mmol) was added, and the orange solution allowed to slowly warm to RT over 17 h period with stirring. Water (100 mL) was added, and the mixture was extracted with 100 mL of ether. The organic layer was washed with 200 mL of a saturated aqueous NaCl solution, dried over $MgSO_4$, filtered, and concentrated to an orange solid. Column chromatography (0→50% EtOAc/hexanes) afforded 7-bromo-2,3-dimethyl-2H-indazole (8: R=R"=Me; 5.28 g, 90%) of as a yellow-stained white solid that was used without further purification.

Step 3

A flask containing 7-bromo-2,3-dimethyl-2H-indazole (3.23 g, 14.4 mmol), 2,4,6-trimethylphenyl boronic acid (3.51 g, 21.4 mmol), freshly ground potassium phosphate (6.04 g, 28.5 mmol), 2-dicyclohexylphosphino-2'-(N,N-dimethylamino)biphenyl (0.225 g, 0.572 mmol), and palladium(II) acetate (0.032 g, 0.14 mmol) was evacuated and back-filled with nitrogen. Toluene (50 mL) was added, and the yellow-orange mixture was stirred at 100° C. for 22 h then allowed to cool. Ether (200 mL) was added, and the yellow solution was decanted from a dark granular solid. The organic layer was sequentially washed with 200 mL of a 10% aqueous NaOH solution and 200 mL of a saturated aqueous NaCl solution, dried over $MgSO_4$, filtered, and concentrated to a pale yellow solid. Column chromatography (0→33% EtOAc/hexanes) afforded 2,3-dimethyl-7-(2,4,6-trimethyl-phenyl)-2H-indazole as an off-white solid (7: R=R'=Me, Ar=2,4,6-trimethylphenyl; 3.03 g, 79%; m.p. 162-164).

The following compounds were prepared from 7-bromo-2,3-dimethyl-2H-indazole in a similar fashion as for 2,3-dimethyl-7-(2,4,6-trimethyl-phenyl)-2H-indazole (using the appropriate electrophiles and/or phenylboronic acids) Compounds named "with trifluoroacetic acid" were purified by reverse-phase HPLC and isolated as the TFA salt):

7-(2,4-Dichloro-phenyl)-2,3-dimethyl-2H-indazole; hydrochloride;
3-Chloro-7-(2,4-dichloro-phenyl)-2-methyl-2H-indazole;
7-(2,4-Dichloro-phenyl)-3-(2-methoxyethoxymethyl)-2-methyl-2H-indazole;
7-(2,4-Dichloro-phenyl)-2-methyl-2H-indazole-3-carboxylic acid methyl ester;
7-(2,4-Dichloro-phenyl)-2-ethyl-2H-indazole-3-carboxylic acid methyl ester (synthesized from 7-bromo-2-ethyl-3-methyl-2H-indazole);
1-[7-(2,4-Dichloro-phenyl)-2-methyl-2H-indazol-3-yl]-ethanol;
7-(3-methoxy-phenyl)-2-methyl-2H-indazole-3-carboxylic acid methyl ester; compound with trifluoro-acetic acid;
7-(2-phenoxy-phenyl)-2-methyl-2H-indazole-3-carboxylic acid methyl ester; compound with trifluoro-acetic acid;
2-Methyl-7-m-tolyl-2H-indazole-3-carboxylic acid methyl ester; compound with trifluoro-acetic acid;
7-(3,5-dimethyl-phenyl)-2-methyl-2H-indazole-3-carboxylic acid methyl ester; compound with trifluoro-acetic acid;
7-(6-Methoxy-2-methyl-pyridin-3-yl)-2-methyl-2H-indazole-3-carboxylic acid methyl ester; compound with trifluoro-acetic acid;
7-(2,5-dimethoxy-phenyl)-2-methyl-2H-indazole-3-carboxylic acid methyl ester; compound with trifluoro-acetic acid;
2-Methyl-7-(4-phenoxy-phenyl)-2H-indazole-3-carboxylic acid methyl ester; compound with trifluoro-acetic acid;
2-Methyl-7-thiophen-3-yl-2H-indazole-3-carboxylic acid methyl ester; compound with trifluoro-acetic acid;
7-Furan-3-yl-2-methyl-2H-indazole-3-carboxylic acid methyl ester; compound with trifluoro-acetic acid;
7-(2,4-Dimsthoxy-phenyl)-2-methyl-2H-indazole-3-carboxylic acid methyl ester; compound with trifluoro-acetic acid;
7-(4-isopropyl-phenyl)-2-methyl-2H-indazole-3-carboxylic acid methyl ester; compound with trifluoro-acetic acid;
7-(2,5-Dichloro-phenyl)-2-methyl-2H-indazole-3-carboxylic acid methyl ester; compound with trifluoro-acetic acid;

Example 4

7-(2,4-Dichloro-phenyl)-2-methyl-2H-pyrazolo[3,4-c]pyridine; hydrochloride

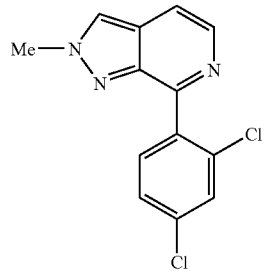

Step 1

A mixture of 2-chloro-4-methyl-3-nitropyridine (28; 1.08 g, 6.24 mmol), 2,4-dichlorophenyl boronic acid (1.26 g, 6.62 mmol), $(Ph_3P)_4Pd(0)$ (0.405 g, 0.350 mmol), 40 mL of DMF, and 20 mL of a 2 M aqueous $K_2HPO_4$ solution was stirred at 70° C. for 40 h. The mixture was partitioned between 200 mL of diethyl ether and 200 mL of water. The organic layer was sequentially washed with 200 mL of water and 200 mL of a saturated aqueous NaCl solution, dried over $MgSO_4$, filtered, and concentrated to a yellow oil mixed with white solid. Column chromatography (0→20% EtOAc/hexanes) afforded slightly impure 2-(2,4-dichloro-phenyl)$_4$-methyl-3-nitro-pyridine (29; 1.19 g; 68%) as a yellow oil that was used without further purification.

Step 2

To a mixture of 2-(2,4-dichloro-phenyl)$_4$-methyl-3-nitropyridine (29; 1.15 g, 4.05 mmol), 10 mL of ethanol, 2.5 mL of water, and 0.5 mL of a concentrated HCl solution at 85° C. was added iron powder (1.37 g, 24.6 mmol). The grey suspension was stirred for 1 h, allowed to cool, and filtered through CELITE® 521 and the residual pad was washed well with methanol. The filtrate was concentrated, and the reddish-orange residue was partitioned between 50 mL of ethyl acetate and 50 mL of a saturated aqueous $NaHCO_3$ solution. The organic layer was washed with 50 ML of a saturated aqueous NaCl solution, dried over $MgSO_4$, filtered, and concentrated to a yellow oil. To the oil was added 10 mL of toluene and acetic anhydride (0.41 mL, 4.35 mmol), and the yellow solution was stirred at 100° C. for 23 h then concentrated to a dark yellow residue. Column chromatography (50→66% EtOAc/hexanes) afforded of N-[2-(2,4-dichloro-phenyl)-4-methyl-pyridin-3-yl]-acetamide (30; 0.815 g; 68%) as an off-white solid.

Step 3

To a mixture of N-[2-(2,4-dichloro-phenyl)-4-methyl-pyridin-3-yl]-acetamide (30; 0.787 g, 2.67 mmol), 30 mL of benzene, acetic anhydride (0.780 mL, 8.27 mmol), and potassium acetate (0.330 g, 3.36 mmol) at 78° C. was added isoamyl nitrite (0.572 mL, 4.27 mmol), and the yellow mixture was stirred for 22 h. After cooling, the mixture was filtered and concentrated to an orange oil. To the oil was added 21 mL of ethanol, 7 mL of water, and lithium hydroxide monohydrate (0.339 g, 8.80 mmol). The orange mixture was stirred for 3 h, then concentrated to remove ethanol. The orange residue was partitioned between 50 mL of diethyl ether and 50 mL of a 10% aqueous NaOH solution, and the aqueous layer was extracted with 50 mL of diethyl ether. The combined organic layers were washed with 100 mL of a saturated aqueous NaCl solution, dried over MgSO$_4$, filtered, loaded onto silica gel and concentrated. Column chromatography (0→20% EtOAc/hexanes) afforded of 7-(2,4-dichloro-phenyl)-1H-pyrazolo[3,4-c]pyridine (31; 0.484 g; 67%) as a foamy pale yellow solid.

Step 4

A mixture of 7-(2,4-dichloro-phenyl)-1H-pyrazolo[3,4-c]pyridine (31; 0.107 g; 0.405 mmol), 4 mL of THF, and 60% sodium hydride/mineral oil (0.020 g, 0.50 mmol sodium hydride) was stirred for 3 h. To the green solution was added dimethyl sulfate (0.040 mL, 0.42 mmol). The resulting yellow, cloudy solution was stirred for 30 m, then quenched with silica gel and concentrated. Column chromatography (0→50% EtOAc/hexanes) afforded of 7-(2,4-dichloro-phenyl)-2-methyl-2H-pyrazolo[3,4-c]pyridine as a white solid (32; 0.029 g; 26%).

To a solution of 7-(2,4-dichloro-phenyl)-2-methyl-2H-pyrazolo[3,4-c]pyridine (0.029 g, 0.10 mmol) in 1 mL of diethyl ether was added 0.100 mL of a 2 M solution of HCl in ether. The resulting white suspension was stirred for 15 m then concentrated to afford 0.031 g of 7-(2,4-dichloro-phenyl)-2-methyl-2H-pyrazolo[3,4-c]pyridine hydrochloride (32 HCl) as an off-white solid: m.p. 191-196.

Example 5

7-(3,5-Dichloro-pyridin-2-yl)-2-methyl-2H-indazole; hydrochloride

Step 1

DMSO (5 mL) under nitrogen was degassed by three freeze-pump-thaw sequences. To it was added 7-bromo-2-methyl-2H-indazole (0.100 g, 0.474 mmol), bis(pinacolato)diboron (0.132 g, 0.520 mmol), potassium acetate (0.138 g, 1.41 mmol), and [1.1'-bis(diphenylphosphino)ferrocene]dichloropalladium(II) (0.012 g, 0.015 mmol), and the mixture was subjected to one more freeze-pump-thaw sequence. The mixture was stirred for 19 h at 80° C., allowed to cool, and 20 mL of water were added. The mixture was extracted with three 5 mL portions of ethyl acetate. The combined organic layers were dried over Na$_2$SO$_4$, filtered, and concentrated to a brown solid. Column chromatography (0→90% EtOAc/hexanes) afforded slightly impure 2-methyl-7-(4,4,5,5-tetramethyl-[1,3,2]dioxaborolan-2-yl)-2H-indazole that was used without further purification (10; 0.062 g, 51%).

Step 2

A mixture of 2-methyl-7-(4,4,5,5-tetramethyl-[1,3,2]dioxaborolan-2-yl)-2H-indazole (0.040 g, 0.15 mmol), 2,3,5-trichloropyridine (0.274 g, 1.50 mmol), (Ph$_3$P)$_4$Pd(0) (0.019 g, 0.017 mmol), 2 mL of DMF, and 2 mL of a 2 M K$_3$PO$_4$ solution was stirred at 65° C. for. 16 h then allowed to cool. Water (10 mL) was added, and the mixture was extracted with three 5 mL portions of ethyl acetate. The combined organic layers were dried over Na$_2$SO$_4$, filtered, and concentrated to a brown solid. Column chromatography (0→50% EtOAc/hexanes) afforded of 7-(3,5-dichloro-pyridin-2-yl)-2-methyl-2H-indazole (7:R=Me; R'=H; Ar=3,5-dichloro-pyridin-2-yl; 0.042 g; 93%).

To a solution of 7-(3,5-dichloro-pyridin-2-yl)-2-methyl-2H-indazole (0.042 g) in ether was added a 2 M solution of HCl in ether. The mixture was filtered to afford 0.039 g of 7-(3,5-Dichloro-pyridin-2-yl)-2-methyl-2H-indazole hydrochloride as a yellow solid.

2-methyl-2H-indazole (using the appropriate aryl halides for the Suzuki coupling) (those reported as compounds "with trifluoro-acetic acid" were purified by reverse-phase HPLC):

2-Methyl-7-phenyl-2H-indazole; compound with trifluoro-acetic acid 7-(3-Chloro-5-trifluoromethyl-pyridin-2-yl)-2-methyl-2H-indazole 2-(2-Methyl-2H-indazol-7-yl)-nicotinonitrile 3-Methyl-4-(2-methyl-2H-indazol-7-yl)-benzonitrile Example 6

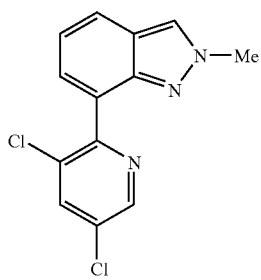

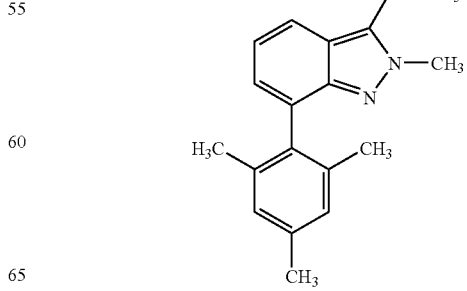

Step 1

A mixture of 7-bromo-2-methyl-2H-indazole (6: R=Me; 2.01 g, 9.53 mmol), 2,4,6-trimethylphenyl boronic acid (1.70 g, 10.4 mmol), tetrakis(triphenylphosphine)palladium (0) (0.657 g, 0.569 mmol), 70 mL of DMF, and 33 mL of a 2 M aqueous $K_2HPO_4$ solution was stirred at 69° C. for 6.5 d. The mixture was partitioned between 350 mL of diethyl ether and 350 ML of water. The organic layer was washed with 350 mL of a saturated aqueous NaCl solution, dried over $MgSO_4$, filtered, and concentrated to a pale yellow oil. Column chromatography (0→33% EtOAc/hexanes) afforded of impure 2-methyl-7-(2,4,6-trimethyl-phenyl)-2H-indazole (5: R=Me, Ar=2,4,6-trimethylphenyl; 1.44 g) as a white solid that was used without further purification.

Step 2

To a solution of the above-prepared impure 2-methyl-7-(2,4,6-trimethyl-phenyl)-2H-indazole (0.500 g) in 10 mL of THF at −78° C. was added a 2.0 M solution of lithium diisopropylamide in tetrahydrofuran/heptane/ethylbenzene (1.2 mL, 2.4 mmol). The yellow solution was stirred at 0-5° C. for 15 m, and the resulting purple solution rechilled to −78° C. for 15 m. Acetaldehyde (0.14 mL, 2.5 mmol) was added, and the resulting yellow solution was stirred for 90 m then quenched with silica gel and concentrated. Column chromatography (0→50% EtOAc/hexanes) afforded of 1-[2-methyl-7-(2,4,6-trimethyl-phenyl)-2H-indazol-3-yl]-ethanol (12a: R=Me, R'=2,4,6-trimethylphenyl, E=CH(OH)Me; 0.280 g; 48%; m.p. 246) as a white solid.

The following compounds were prepared in a similar fashion as for 1-[2-methyl-7-(2,4,6-trimethylphenyl)-2H-indazol-3-yl]-ethanol (using an appropriate electrophile):

1-[2-Methyl-7-(2,4,6-trimethyl-phenyl)-2H-indazol-3-yl]-ethanone
3-Ethylsulfanyl-2-methyl-7-(2,4,6-trimethyl-phenyl)-2H-indazole Example 7

3-Bromo-7-(2,4-dichloro-phenyl)-2-methyl-2H-indazole

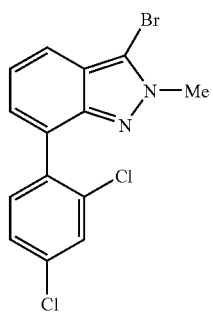

To a solution of 7-(2,4-dichloro-phenyl)-2-methyl-2H-indazole (0.659 g, 2.38 mmol) in 2 mL of acetic acid was added bromine (0.122 mL, 2.38 mmol) dropwise. The yellow-orange solution was stirred for 15 m, in which time an orange solid precipitated. The mixture was concentrated to a yellow solid, which was partitioned between 20 mL of a 10% aqueous NaOH solution and 20 mL of diethyl ether. The organic layer was washed with 20 mL of a saturated aqueous NaCl solution, dried over $MgSO_4$, filtered, and concentrated to a yellow-stained white solid. Column chromatography (0→10% EtOAc/hexanes) afforded 3-bromo-7-(2,4-dichloro-phenyl)-2-methyl-2H-indazole as a white solid (24: Ar=2,4-dichlorophenyl; 0.525 g; 62%; m.p. 137-139).

Example 8

3-chloro-7-(2,4-dichloro-phenyl)-2-methyl-2H-indazole

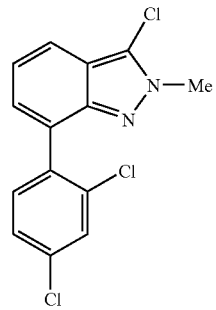

Step 1

To a solution of 7-bromo-2-methyl-2H-indazole (6: R=Me; 0.500 g, 2.37 mmol) in 5 mL of acetic acid was added sulfuryl chloride (0.29 mL, 3.6 mmol). The mixture was stirred for 5 h, then 30 mL of a 2 M aqueous NaOH solution were added. The mixture was extracted with three 30 mL portions of ethyl acetate, and the combined organic layers were dried over $Na_2SO_4$, filtered, and concentrated to a white solid. Column chromatography (0→15% EtOAc/hexanes) afforded slightly impure 7-bromo-3-chloro-2-methyl-2H-indazole (25: R=Me; 0.530 g; 90%) that was used without further purification.

Step 2

A mixture of 7-bromo-3-chloro-2-methyl-2H-indazole (0.079 g, 0.32 mmol), 2,4-dichlorophenyl boronic acid (0.122 g, 0.641 mmol), 2 mL of ethylene glycol dimethyl ether, 2 mL of a 2 M aqueous $Na_2CO_3$ solution, and tetrakis(triphenylphosphine)palladium(0) (0.011 g, 0.010 mmol) was stirred at 88° C. overnight, then diluted with 10 mL of ethyl acetate. The mixture was washed with two 5 mL portions of a saturated aqueous NaCl solution, dried, filtered, and concentrated to a yellow oil. Column chromatography (0→5% EtOAc/hexanes) afforded of 3-chloro-7-(2,4-dichloro-phenyl)-2-methyl-2H-indazole (26: R=Me; Ar=2,4-dichlorophenyl; 0.063 g; 63%) as a white solid.

Example 9

2-methyl-7-(2,4,6-trimethyl-phenyl)-3-vinyl-2H-indazole

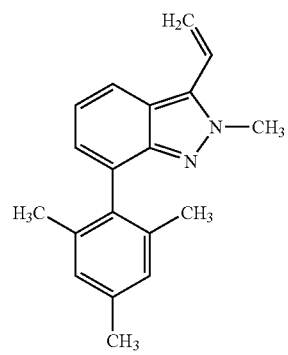

A solution of 1-[2-methyl-7-(2,4,6-trimethyl-phenyl)-2H-indazol-3-yl]-ethanol (0.263 g, 0.893 mmol) and 4-toluene-sulfonic acid hydrate (0.217 g, 1.14 mmol) in 10 mL of toluene was stirred at 103° C. for 16 h then allowed to cool. The yellow-orange solution was sequentially washed with 10 mL of a 10% aqueous NaOH solution and 10 mL of a saturated aqueous NaCl solution, dried over MgSO$_4$, filtered, and concentrated to an orange oil. Column chromatography (20% EtOAc/hexanes) afforded 2-methyl-7-(2,4,6-trimethyl-phenyl)-3-vinyl-2H-indazole (15: R$^a$=R$^b$=H, Ar=2,4,6-trimethylphenyl; 0.135 g; 55%; m.p. 84.9-95.4) as a pale yellow solid.

Example 10

7-(2,4-Dichloro-phenyl)-2-methyl-3-((E)-1-propyl-but-1-enyl)-2H-indazole

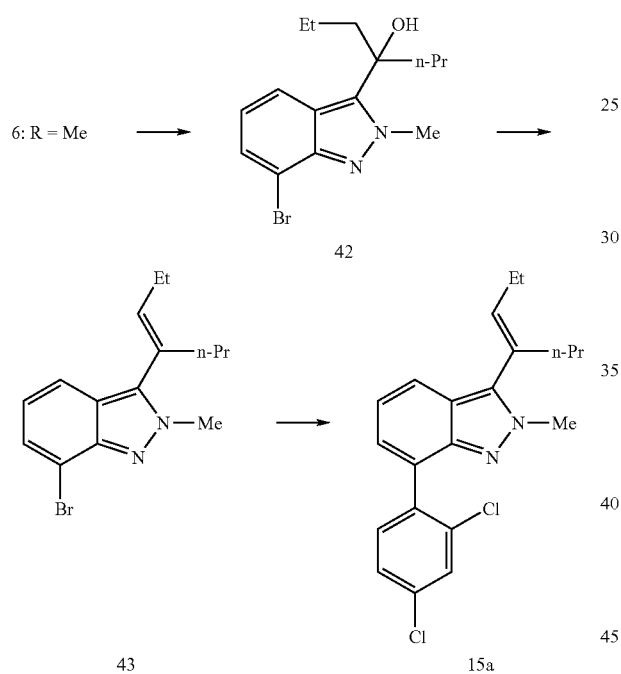

Step 1

To a solution of 7-bromo-2-methyl-2H-indazole (1.5 g, 7.1 mmol) in 18 mL of THF at −78° C. was added a 2 M solution of lithium diisopropylamide in heptane/ethylbenzene/THF (5.3 mL, 11 mmol). The solution was stirred at 0-5° C. for 10 m, then rechilled to −78° C. To it was added 4-heptanone (1.49 mL, 10.6 mmol), and the solution was stirred overnight, allowing to slowly warm to room temperature. A saturated aqueous NaHCO$_3$ solution (40 mL) was added, and the mixture was extracted with three 30 mL portions of ethyl acetate. The combined organic layers were dried over Na$_2$SO$_4$, filtered, and concentrated to a brown solid. Column chromatography (0→20% EtOAc/hexanes) afforded 4-(7-bromo-2-methyl-2H-indazol-3-yl)-heptan-4-ol (42; 1.80 g; 78%).

Step 2

A solution of 4-(7-bromo-2-methyl-2H-indazol-3-yl)-heptan-4-ol (1.75 g, 5.38 mmol), 50 mL of toluene, and 4-toluenesulfonic acid (1.23 g, 6.46 mmol) was stirred at 110° C. for 20 h, then allowed to cool. A saturated aqueous NaHCO$_3$ solution (50 mL) was added, and the mixture was extracted with three 30 mL portions of ethyl acetate. The combined organic layers were dried over MgSO$_4$, filtered, and concentrated to a brown oil. Column chromatography (0→8% EtOAc/hexanes) afforded of 7-bromo-2-methyl-3-((E)-1-propyl-but-1-enyl)-2H-indazole (43; 1.47 g; 89%).

Step 3

A mixture of 7-bromo-2-methyl-3-((E)-1-propyl-but-1-enyl)-2H-indazole (1.47 g, 4.79 mmol), 2,4-dichlorophenyl boronic acid (1.32 g, 6.94 mmol), 18 mL of ethylene glycol dimethyl ether, tetrakis(triphenylphosphine)palladium(0) (0.166 g, 0.143 mmol), and 20 mL of a 2 M aqueous Na$_2$CO$_3$ solution was stirred at 85° C. overnight, then allowed to cool. Ethyl acetate (50 mL) was added, and the mixture was washed with two 40 mL portions of a saturated aqueous NaCl solution. The combined aqueous layers were extracted with 20 mL of ethyl acetate. The combined organic layers were dried over Na$_2$SO$_4$, filtered, and concentrated to a brown oil. Column chromatography (0→5% EtOAc/hexanes) afforded 7-(2,4-dichloro-phenyl)-2-methyl-3-((E)-1-propyl-but-1-enyl)-2H-indazole (15a; 1.57 g; 88%) as a white solid.

Example 11

7-(2,4-Dichloro-phenyl)-3-ethynyl-2-methyl-2H-indazole

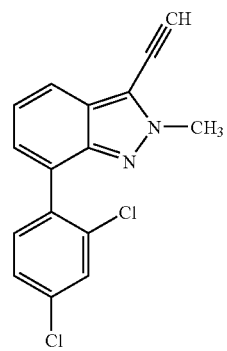

Step 1

2-methyl-7-bromoindazole (6: R=Me; 5.31 g, 25.16 mmol) in THF (100 mL) was cooled to −78° C. under an Ar atmosphere. A 2 M solution of LDA in heptane/THF/ethylbenzene (20 mL, 40 mmol) was added slowly. The mixture was then stirred at −78° C. for 10 minutes and 0° C. for 20 minutes. The solution was re-cooled to −78° C., DMF (6 mL, 77.48 mmol) was added slowly via syringe. The mixture was stirred and allowed to warm to room temperature for 19 hours. The reaction was partitioned between EtOAc and NH$_4$Cl solution. The aqueous layer was extracted with EtOAc two times. The combined organic layers were dried over MgSO4 and concentrated to almost dryness. The resulting yellow solids (3.83 g) were collected by filtration and washed with 10% EtOAc in hexanes. The filtrate was concentrated and the residue purified by SiO$_2$ chromatography and eluted with a EtOAc/hexane (5→30%) over 30 minutes to provide an additional crop of 17a (0.46 g, total yield 62%) along with the recovered starting material (0.768 g, 14%).

Step 2

A DME solution (100 mL) of the 3-formyl-7-bromoindazole (17a; 3.83 g, 16.02 mmol), boronic acid (6.10 g, 31.97 mmol) and the palladium catalyst (0.55 g, 0.47 mmol) was flushed with Ar for 5 minutes. A 2 M $Na_2CO_3$ solution (23 mL, 46 mmol) was added. The mixture was stirred at 80° C. under Ar. $Na_2CO_3$ precipitated and $H_2O$ (65 mL) was added to dissolve the salt. The reaction mixture was stirred at 80° C. for 19 hours and then cooled to room temperature. The mixture was partitioned between EtOAc and water and the organic layer was dried over $MgSO_4$. The solvent was removed to almost dryness and the solid 17b (Ar=2,4,6-trimethylphenyl; 3.36 g) was collected by filtration, the filtrate provided a second crop of product (0.90 g, combined yield of 86%; mp: 153.4-156.4° C.).

Step 3

A MeOH/THF solution (70 mL/55 mL) of 17b (Ar=2,4, 6-trimethylphenyl; 1.56 g, 5.11 mmol) and 1-(dimethoxyphosphoryl)-2-oxo-propane-1-diazonium (1.27 g, 6.13 mmol) was treated with $K_2CO_3$ (1.41 g, 10.20 mmol) under nitrogen. The mixture was stirred for 6 hours and the reaction was monitored by tlc until complete. The mixture was partitioned between EtOAc and water and the organic layer was dried over $MgSO_4$. The solvent was removed and the residue purified by SiO2 chromatography and eluted with 8% EtOAc in hexanes to give 18 (Ar=2,4,6-trimethylphenyl) as an off white solid (1.176 g, 76%; mp 129.9-130.9° C.).

Example 12

7-(2,4-Dichloro-phenyl)-2-methyl-2H-indazole-3-carbonitrile

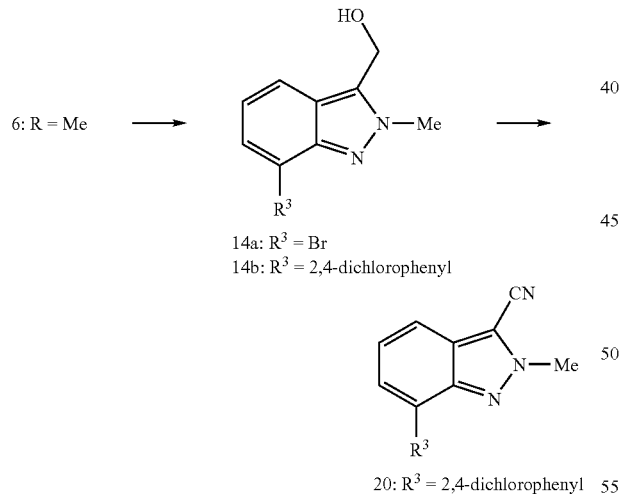

Step 1

To a solution of 7-bromo-2-methyl-2H-indazole (6: R=Me; 0.578 g, 2.93 mmol) in 15 mL of THF at −78° C. was added a 2.0 M solution of lithium diisopropylamide in tetrahydrofuran/heptane/ethylbenzene (1.8 mL, 3.6 mmol). The yellow-orange solution was stirred at 0-5° C. for 15 m, then rechilled to −78° C. for 15 m. Paraformaldehyde (0.92 g) was added, and the orange mixture was rapidly stirred at −78° C. for 75 m then at room temperature for 100 m. The mixture was loaded onto silica gel and concentrated. Column chromatography (0→66% EtOAc/hexanes) afforded 0.662 g of impure (7-bromo-2-methyl-2H-indazol-3-yl)-methanol (14a).

Step 2

A solution of impure (7-bromo-2-methyl-2H-indazol-3-yl)-methanol (0.642 g) and tetrakis(triphenylphosphine)palladium(0) (0.089 g, 0.077 mmol) in 25 mL of ethylene glycol dimethyl ether was stirred for 30 m. To the solution was added 2,4-dichlorophenylboronic acid (1.00 g, 5.27 mmol) then 3.8 mL of a 2 M aqueous $Na_2CO_3$ solution, and the yellow mixture was stirred at 78° C. for 15 h. The mixture was partitioned between 50 mL of ethyl acetate and 50 mL of water. The organic layer was washed with 50 mL of a saturated aqueous NaCl solution, dried over $MgSO_4$, filtered, and concentrated to an orange oil. Column chromatography (0→50% EtOAc/hexanes) followed by crystallization from benzene afforded 0.203 g ("25%") of 7-(2,4-dichloro-phenyl)-2-methyl-2H-indazol-3-yl]-methanol (14b).

To a solution of [7-(2,4-dichloro-phenyl)-2-methyl-2H-indazol-3-yl]-methanol from step 2 (0.153 g) in 2 mL of THF was added a 2 M ammonia in IPA solution (1.0 mL, 2.0 mmol), $MgSO_4$ (0.910 g, 7.56 mmol), and 85% activated $MnO_2$ (0.771 g, 7.54 mmol). The dark mixture was stirred for 2 d, then filtered thru CELITE® 521 (rinsing with dichloromethane) and concentrated to a yellow solid. Column chromatography (0→10% EtOAc/hexanes) afforded 7-(2,4-dichloro-phenyl)-2-methyl-2H-indazole-3-carbonitrile (20: $R^3$=2,4-dichlorophenyl; 0.058 g; 39%; m.p. 137-139) as a white solid:

Example 13

3-Ethanesulfonyl-2-methyl-7-(2,4,6-trimethyl-phenyl)-2H-indazole

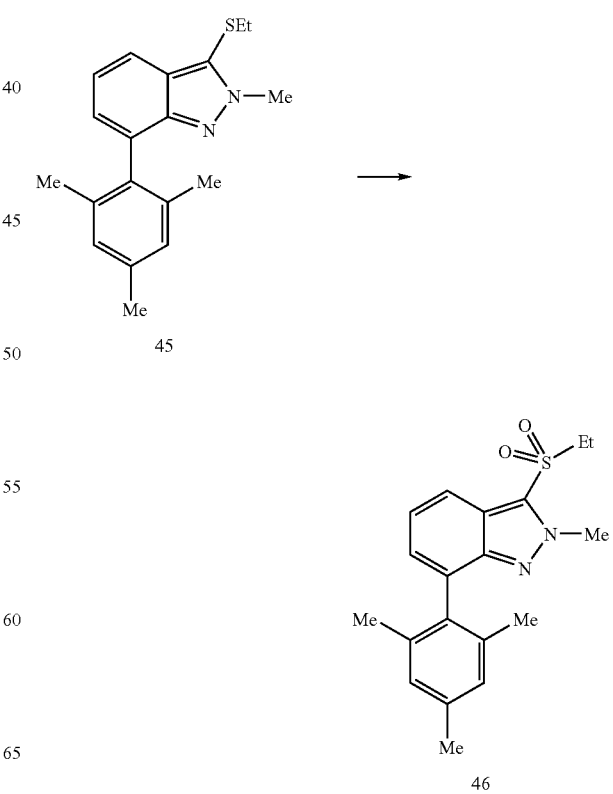

To a solution of 3-ethylsulfanyl-2-methyl-7-(2,4,6-trimethyl-phenyl)-2H-indazole (45; 0.034 g, 0.11 mmol) in 1 mL of dichloromethane was added 3-chloroperbenzoic acid (0.083 g of 57-86% pure material, from Aldrich chemical company). The colorless solution was stirred for 16 h, then diluted with 5 mL of dichloromethane and washed with 5 mL of a 10% aqueous NaOH solution. The aqueous solution was extracted with 5 mL of dichloromethane, and the combined organic layers were dried over $MgSO_4$, filtered, and concentrated to a yellow oil. Column chromatography (0→20% EtOAc/hexanes) afforded 3-ethanesulfonyl-2-methyl-7-(2,4,6-trimethyl-phenyl)-2H-indazole (46; 0.017 g; 45%) as a white solid.

Example 14

7-(2,4-Dichloro-phenyl)-2-methyl-2H-indazole-3-carboxylic acid cyclopropylmethyl-propyl-amide

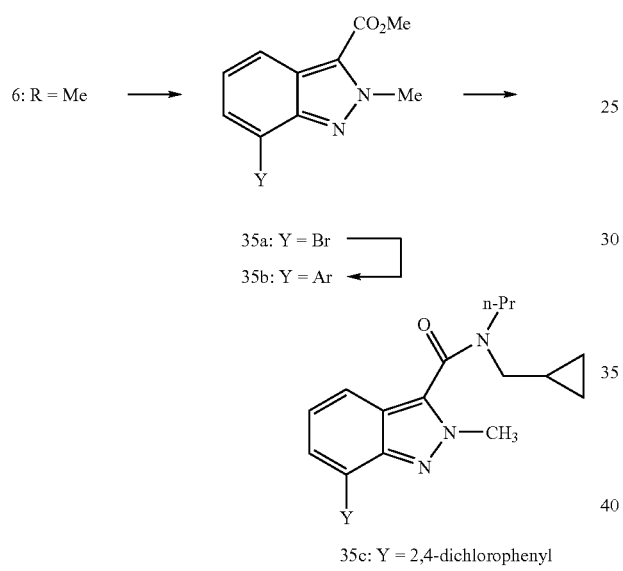

Step 1

To a solution of 7-bromo-2-methyl-2H-indazole (6: R=Me, 1.50 g, 7.12 mmol) in 50 mL of THF at −78° C. was added a 2 M solution of lithium diisopropylamide in THF/heptane/ethylbenzene (4.3 mL, 8.6 mmol). The solution was stirred at 0-5° C. for 15 m, then rechilled to −78° C. To the solution was added methyl chloroformate (0.66 mL, 8.5 mmol) all at once, and the mixture was stirred while slowly warmed to room temperature over 19 h. The reaction was quenched with silica gel and concentrated. Column chromatography (0→20% EtOAc/hexanes) afforded of 7-bromo-2-methyl-2H-indazole-3-carboxylic acid methyl ester (35a: 1.52 g; 79%; m.p. 131-132) as a pale yellow solid.

Step 2

A mixture of 35a (0.750 g, 2.79 mmol), 2,4-dichlorophenyl boronic acid (1.06 g, 5.57 mmol), 10 mL of ethylene glycol dimethyl ether, tetrakis(triphenylphosphine) palladium(0) (0.097 g, 0.084 mmol), and 10 mL of a 2 M aqueous $Na_2CO_3$ solution was stirred at 85° C. overnight, then allowed to cool. Ethyl acetate (50 mL) was added, and the mixture was washed with 30 mL of a saturated aqueous NaCl solution, dried over $MgSO_4$, filtered, and concentrated to a yellow oil. Column chromatography (0→10% EtOAc/hexanes) afforded of 7-(2,4-dichloro-phenyl)-2-methyl-2H-indazole-3-carboxylic acid methyl ester (35b: 0.582 g; 62%; m.p. 128-131) as a white solid:

Step 3

To a solution of N-propylcyclopropanemethyl amine (0.69 mL, 4.8 mmol) in 12 mL of benzene was slowly added a 2M solution of trimethylaluminum in heptane (2.4 mL, 4.8 mmol), and the solution was stirred for 75 m. The solution was transferred with a pipette to a solution of 35b (0.200 g, 0.597 mmol) in 10 mL of benzene. The solution was heated to 79° C., stirred for 2 d, then cooled to 0-5° C. A 2 M aqueous NaOH solution (20 mL) was slowly added, and the mixture was extracted with three 20 mL portions of dichloromethane. The combined organic layers were washed with 40 mL of a saturated NaCl solution, dried over $MgSO_4$, filtered, and concentrated to a brown oil. Column chromatography (0→20% EtOAc/hexanes) afforded 7-(2,4-dichloro-phenyl)-2-methyl-2H-indazole-3-carboxylic acid cyclopropylmethyl-propyl-amide (35c: 0.117 g; 47%) as an oil.

Example 15

7-(2,4-Dichloro-phenyl)-2-methyl-2H-indazole-3-carboxylic acid methylamide

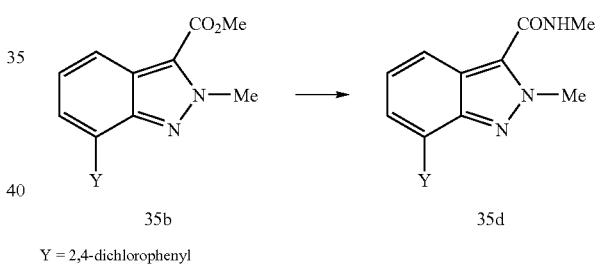

A solution of 7-(2,4-dichloro-phenyl)-2-methyl-2H-indazole-3-carboxylic acid methyl ester (35b; 0.050 g, 0.15 mmol) in 4 mL of a 2 M solution of methylamine in methanol was stirred for 6 d, then concentrated to a white solid. Column chromatography (0→45% EtOAc/hexanes) afforded of 7-(2,4-dichloro-phenyl)-2-methyl-2H-indazole-3-carboxylic acid methylamide (35d; 0.044 g; 88%).

Example 16

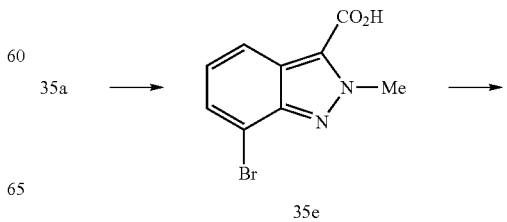

-continued

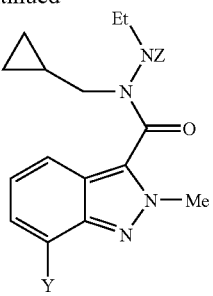

35f: Y = Br; Z = Boc
35h: Y = 2,4-dichlorophenyl; Z = H₂⁺Cl⁻
35g: Y = 2,4-dichlorophenyl; Z = Boc Step 1

A mixture of 7-bromo-2-methyl-2H-indazole-3-carboxylic acid methyl ester (35a; 0.215 g, 0.799 mmol), 8 mL of a 2 M aqueous NaOH solution, and 6 mL of ethanol was stirred at 55° C. overnight, then concentrated to remove ethanol. The remaining aqueous layer was acidified with a 10% aqueous HCl solution and extracted with three 20 mL portions of ethyl acetate. The combined organic layers were dried over Na₂SO₄, filtered, and concentrated to afford crude 7-bromo-2-methyl-2H-indazole-3-carboxylic acid (35e; 0.193 g; 94%) which was used without further purification.

Step 2

To a mixture of 35e (0.075 g, 0.29 mmol) in 3 mL of chloroform was added thionyl chloride (0.058 mL, 0.79 mmol) and 1 drop of DMF. The mixture was stirred at reflux for 3 h, then concentrated. Chloroform (2.5 mL) was added, followed by N'-cyclopropylmethyl-N-ethyl-hydrazinecarboxylic acid tert-butyl ester (0.062 g, 0.29 mmol) in 0.5 mL of chloroform. The solution was stirred overnight, then diluted with 40 mL of dichloromethane, sequentially washed with a 2 M aqueous sodium hydroxide solution and a saturated aqueous NaCl solution, dried over Na₂SO₄, filtered, and concentrated to an oil. Column chromatography (0→10% EtOAc) afforded N-(7-bromo-2-methyl-2H-indazole-3-carbonyl)-N'-cyclopropylmethyl-N-ethyl-hydrazinecarboxylic acid tert-butyl ester (35f: 0.025 g; 20%).

Step 3

A mixture of 35f (0.025 g, 0.055 mmol), 2,4-dichlorophenyl boronic acid (0.024 g, 0.11 mmol), tetrakis(triphenylphosphine)palladium(0) (0.002 g, 0.002 mmol), 1 mL of ethylene glycol dimethyl ether, and 1 mL of a 2 M aqueous Na₂CO₃ solution was stirred at 85° C. overnight. Ethyl acetate (50 mL) was added, and the mixture was washed with two 20 mL portions of a saturated aqueous NaCl solution, dried over Na₂SO₄, filtered, and concentrated to a clear oil. Column chromatography (0→15% EtOAc/hexanes) afforded N-cyclopropylmethyl-N'-[7-(2,4-dichlorophenyl)-2-methyl-2H-indazole-3-carbonyl]-N-ethyl-hydrazinecarboxylic acid tert-butyl ester (35 g; 0.020 g; 70%).

Step 4

A methanolic HCl solution was prepared by slow addition of 1 mL of acetyl chloride to 4 mL of methanol. This solution was added to 35 g (0.020 g, 0.039 mmol) and the solution was stirred overnight then concentrated to afford crude 7-(2,4-dichloro-phenyl)-2-methyl-2H-indazole-3-carboxylic acid N-cyclopropylmethyl-N'-ethyl-hydrazide (35h) which was purified by reverse-phase HPLC.

Example 17

N'-Cyclopropylmethyl-N-ethyl-hydrazinecarboxylic acid tert-butyl ester

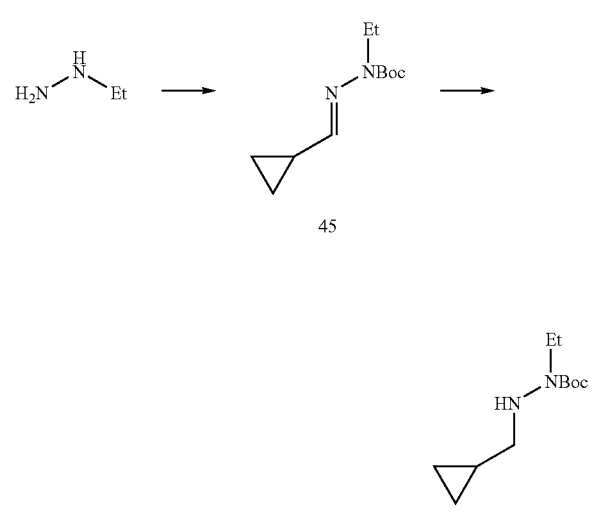

Step 1

To a solution of ethyl hydrazine oxalate (1.03 g, 0.686 mmol) and di-tert-butyl dicarbonate (1.05 g, 4.81 mmol) in 50 mL of methanol was added triethylamine (1.86 mL, 13.4 mmol). The solution was stirred for 1 h, cyclopropane carboxaldehyde (0.425 mL, 5.69 mmol) was added, and the solution was stirred for 2 h then concentrated. EtOAc (50 mL) was added, and the mixture was sequentially washed with two 20 mL portions of a 2 M aqueous NaOH solution and 20 mL of water, dried over Na₂SO₄, filtered, and concentrated to a clear oil. Column chromatography (0→20% EtOAc/hexanes) afforded N'-[1-cyclopropyl-meth-(E)-ylidene]-N-ethyl-hydrazinecarboxylic acid tert-butyl ester (45; 0.780 g; 77%).

Step 2

A mixture of sodium cyanoborohydride (0.276 g, 4.39 mmol), 5 mL of THF, and TMSCl (0.56 mL, 4.4 mmol) was stirred for 10 m, then 45 (0.780 g, 3.67 mmol) in 10 mL of THF was slowly added. The mixture was stirred for 1 h, then 15 mL of a 2 M aqueous NaOH solution were added. The mixture was extracted with 40 mL of diethyl ether, and the organic layer was washed with two 20 mL portions of a saturated aqueous NaCl solution, dried over Na₂SO₄, filtered, and concentrated. Column chromatography (0→20% EtOAc/hexanes) afforded N'-cyclopropylmethyl-N-ethyl-hydrazinecarboxylic acid tert-butyl ester (46; 0.323 g; 41%).

Example 18

[7-(2,4-Dichloro-phenyl)-2-methyl-2H-indazole-3-yl]-dipropyl-amine hydrochloride

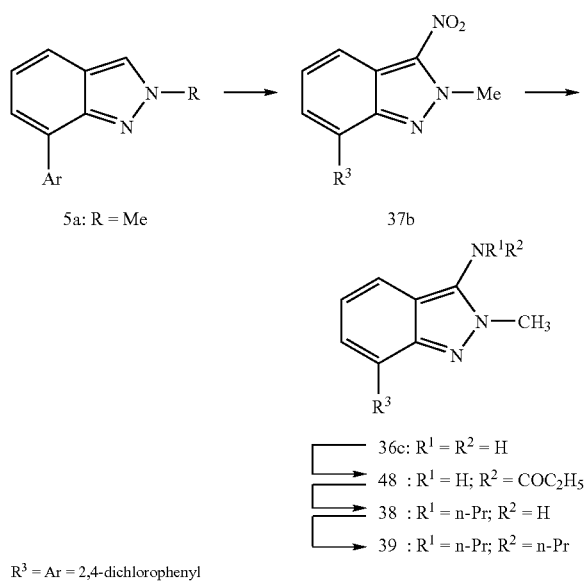

$R^3$ = Ar = 2,4-dichlorophenyl

Step 1

7-(2,4-Dichlorophenyl)-2-methyl-indazole (5a; 0.293 g, 1.05 mmol) was dissolved in 3.0 mL of glacial HOAc and 0.3 mL of acetic anhydride then cooled in an ice bath. 90% Nitric acid (0.070 mL; 1.48 mmol) was added all at once and allowed to stir at rt for 1 hr, then heated in an oil bath at 50° for 2 hr. The reaction mixture was cooled to rt then treated with ice (~10 g). The mixture was extracted with ether (2×40 mL). The combined ethereal extracts were washed with sat'd NaHCO$_3$ solution (2×50 mL), then dried over MgSO$_4$. Evaporation afforded a mixture of 3 isomers which were separated by silica gel flash chromatography (EtOAc:hexane, 1:9) which afforded 37b (0.077 g; 22%).

Step 2

Nitroindazole 37b and 10 mg of 10% Pd on C were combined in 7 mL of MeOH then stirred under a hydrogen atmosphere (1 atm) overnight. Filtration of the catalyst and evaporation of the solvent afforded 36c (0.070 g), which was used in the next step without further purification.

Step 3

Amine 36c (70 mg, 0.23 mmol) and TEA (0.037 mL, 26 mg, 0.26 mmol) were dissolved in methylene chloride (3 mL) under a N$_2$ atmosphere and cooled in an ice bath. Propionyl chloride (0.022 mL, 24 mg, 0.26 mmol) was added and then allowed to warm to room temp. When the reaction was complete, the mixture was evaporated and the residue flash chromatographed (EtOAc:hexane, 1:1) to afford 48 (0.068 g; 82%).

Step 4

Amide 48 (0.068 mg, 0.19 mmol) was dissolved in 5 mL dry THF under a N$_2$ atmosphere. A 1M BH$_3$-THF solution (0.40 mL, 0.40 mmol) was added all at once and the mixture heated at reflux for 2 hr, cooled to rt and 1 mL 6N HCl was cautiously added, and the mixture was reheated at reflux for 1 hr, and then cooled to rt. The mixture was made basic with 6N NaOH solution, then extracted with methylene chloride (2×25 mL). The combined extracts were washed with brine and dried over Na$_2$SO$_4$. Evaporation of the solvent afforded 38 (0.071 g) as a light brown viscous liquid, which was used without further purification.

Step 5

Amine 38 and propionaldehyde (0.032 mL, 26 mg, 0.44 mmol) were combined in 3 mL of DCE under nitrogen and allowed to stir at rt for 10 m. Na(OAc)$_3$BH (102 mg, 0.48 mmol) was added all at once and the reaction mixture stirred at rt overnight. The reaction mixture was diluted with 20 mL methylene chloride and washed with dilute NH$_4$OH solution. The CH$_2$Cl$_2$ solution was separated and dried (Na$_2$SO$_4$). Evaporation of the solvent afforded a residue which was purified by flash chromatography (EtOAc:hexane, 1:9) to afford 27.4 mg of the free base of 39 as a viscous liquid. The free base was dissolved in 1 mL ether and treated with 0.1 mL 2M HCl in ether solution which afforded 39 (0.022 g) as a white solid.

Example 19

3-Allyl-7-(2,4-dichloro-phenyl)-2-methyl-2H-indazole

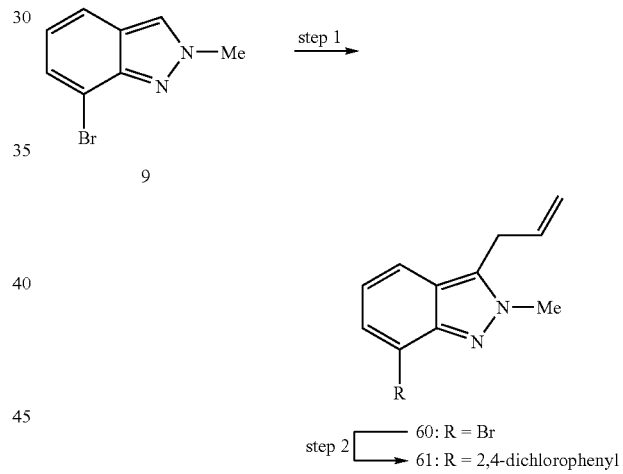

Step 1

To a solution of 7-bromo-2-methyl-indazole (9, 0.200 g, 0.948 mmol) and dry THF (1.5 mL) which was cooled to −78° C. and maintained under an N$_2$ atmosphere was added dropwise LDA (947.5 µL, 1.90 mmol, 2.0M solution in heptane/THF/ethylbenzene). After the addition was completed the reaction mixture was stirred for 10 min and warmed to 0° C. for 10 min. The dark red solution was cooled to −78° C. and allyl bromide (123.0 µL, 1.42 mmol) was added dropwise. The solution was allowed to warm to RT and stirred over the weekend. The reaction was quenched by the addition of saturated NH$_4$Cl (10 mL) and the resulting solution was twice extracted with EtOAc. The combined extracts were dried (MgSO$_4$), filtered and evaporated. The crude product was purified by flash chromatography on SiO$_2$ (0 to 40% EtOAc/heptane in a linear gradient over 20 min) to afford 60 (0.032 g) as a yellow solid. Also recovered from the column was 0.078 g of starting material.

Step 2

A round bottom flask was charged with 61 (0.032 g, 0.127 mmol), 2,4-dichlorobenzeneboronic acid (0.049 g, 0.254 mmol), Pd(PPh₃)₄ (0.0042 g, 0.0038 mmol), DME (30.0 μL) and 2M Na₂CO₃ (300.0 μL). The reaction mixture was heated to 80° C. overnight. The reaction mixture was cooled to room temperature and diluted with H₂O and twice extracted with EtOAc and the combined organic phases were dried (MgSO₄), filtered and concentrated in vacuo. The crude product was purified by flash chromatography on SiO₂ (0 to 10% EtOAc/heptane in a linear gradient over 20 min) to afford 62 (0.015 g) as a yellow oil.

Example 20

7-(2,4-Dichloro-phenyl)-3-methoxymethyl-2-methyl-2H-indazole

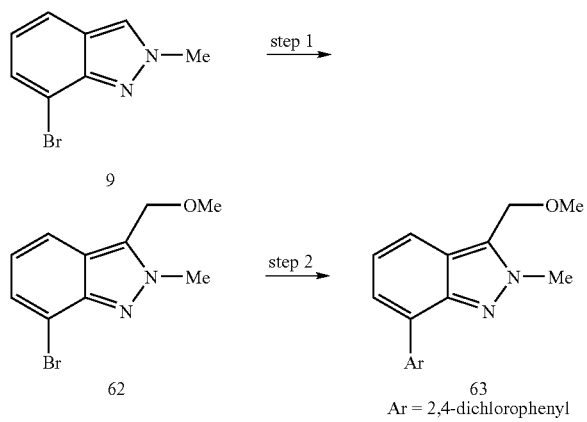

Step 1

A solution of 7-bromo-2-methyl indazole (9, 0.050 g, 0.24 mmol) and THF (1 mL) was cooled to −78° C. and a solution of LDA (0.17 μL, 2.0M in THF/heptane/ethylbenzene) was added via syringe. The reaction was stirred for 15 min at −78° C. and 25 mL of chloromethyl methyl ether was added dropwise. After an additional 10 min the reaction was warmed to RT and the volatile solvents were removed in vacuo. The residue was partitioned between DCM (10 mL) and water. The organic solution was washed with brine, dried (MgSO₄), filtered and evaporated. The crude product was purified by flash chromatography on SiO₂ (50% EtOAc/hexane) which afforded 62 (0.052 g) contaminated with a small amount of starting material.

Step 2

A KIMAX® tube was charged with 7-bromo-3-methoxymethyl-2-methylindazole (62, 50 mg, 0.12 mmol) from step 1, dichlorobenzeneboronic acid (46 mg, 0.12 mmol), 2M aqueous Na₂CO₃ (1 mL) and DME (1 mL). The tube was flushed with N₂ and Pd(PPh₃)₄ (0.008 g, 0.007 mmol) was added and the tube was sealed. The reaction mixture was warmed to 85° C. and stirred for 12 h. The reaction mixture was cooled to RT and diluted with 5 mL of EtOAc, washed twice with brine and dried (Na₂SO₄). The organic phase was filtered and evaporated in vacuo and the crude product purified by flash chromatography on SiO₂ (0 to 25% EtOAc/hexane) to afford 63.

Example 21

Carbamic acid 7-(2,4-dichloro-phenyl)-2-methyl-2H-indazol-3-ylmethyl ester

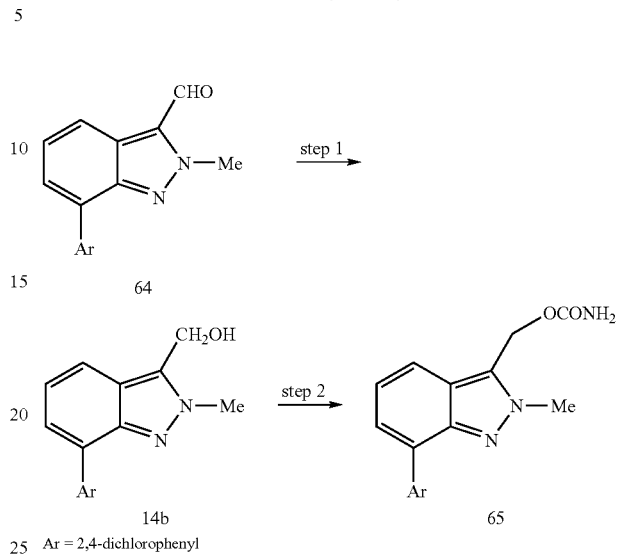

Ar = 2,4-dichlorophenyl

Step 1

Aldehyde 64 (3.00 g, 9.83 mmol) was suspended in MeOH (50 mL) at 0° C. and solid NaBH₄ (0.41 g, 10.84 mmol) was added portionwise over 10 min. The resulting mixture was stirred at 0° C. for 30 min then at RT for another 10 min. The reaction was quenched by the addition of ice. Methanol was removed by rotary evaporation. The residue was partitioned between EtOAc and H₂O. The aqueous layer was twice extracted with EtOAc. The combined organic layers were dried (MgSO₄), filtered and evaporated to afford 14b (2.92 g, 9.51 mmol, 97%).

Step 2

To a suspension of 14b (310 mg, 1.01 mmol) in benzene (2 mL) was added NaOCN (0.130 g, 2.00 mmol). TFA (0.16 mL, 2.08 mmol) was then added slowly. The mixture was stirred at RT overnight and partitioned between EtOAc and water. The organic layer was dried (MgSO₄) and concentrated in vacuo. The crude product was purified by flash chromatography on SiO₂ (20 to 30% EtOAc/hexane in a linear gradient over 30 min) to afford 65 (0.94 g, 27% theory).

Example 22

Dimethyl-carbamic acid 7-(2,4-dichloro-phenyl)-2-methyl-2H-indazol-3-ylmethyl ester

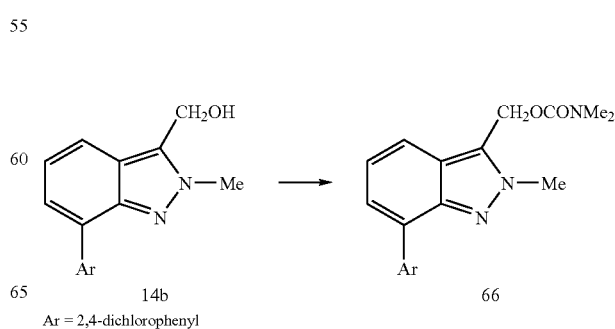

Ar = 2,4-dichlorophenyl

To a solution of alcohol 14b (0.045 g, 0.146 mmol) and benzene (1 mL) was added NaH (10 mg, 0.25 mmol, 60% mineral oil dispersion) and the reaction mixture was stirred for 10 min. Carbamoyl chloride (0.02 mL, 0.22 mmol) was added and the mixture was stirred at RT overnight. Analysis of the reaction indicated the reaction was not complete. Additional carbamoyl chloride (0.02 mL, 0.22 mmol) was added and the mixture was stirred at 80° C. overnight. The reaction was cooled to RT and partitioned between EtOAc and $H_2O$. The organic layer was dried over $MgSO_4$ and concentrated in vacuo. The residue was purified on a preparative TLC (2 mm thickness, 50% EtOAc/hexanes, 3 elutions) to afford 66 (0.023 g, 42% theory).

Example 23

3-Chloro-7-(2,4-dichloro-phenyl)-2-yl)-2-methyl-2H-indazole

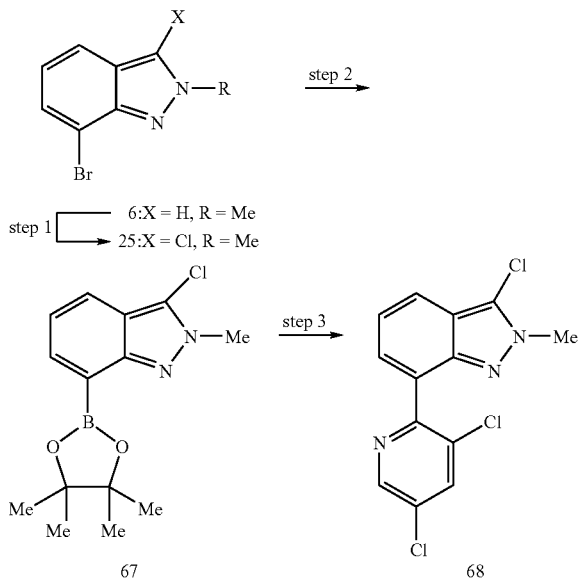

Step 1

A solution of 6 (R=Me, 0.5 g, 2.4 mmol), HOAc (5 mL) and sulfuryl chloride (0.29 mL, 0.490 g, 3.6 mmol) was stirred for 4 h under an $N_2$ atmosphere. The reaction mixture was added to 2M NaOH (30 mL) and thrice extracted with EtOAc (30 mL). The combined extracts were dried ($Na_2SO_4$) and evaporated. The crude product was purified by flash chromatography over SiO2 (0 to 15% EtOAc/hexane) to afford 25 (R=Me, 530 mg; 90% theory).

Step 2

To DMSO (1.3 mL, thrice degassed) maintained under a $N_2$ atmosphere was added pinacol borane (0.056 g, 0.22 mmol), KOAc (0.059 g, 0.60 mmol), $PdCl_2(dppf)$ (0.005 g, 0.006 mmol) and 25 (R=Me, 0.050 g, 0.200 mmol). The reaction mixture was heated to 85° C. for 1 h then cooled to RT. $H_2O$ (10 mL) was added and the solution stirred for 1 min and thrice extracted with EtOAc (5 mL). The combined extracts were dried ($Na_2SO_4$), filtered and concentrated in vacuo. The crude product was purified by flash chromatography over $SiO_2$ (0 to 30% EtOAc/hexane to afford impure 67 (0.065 g).

Step 3

A KIMAX® tube was charged with 67 (65 mg, 0.23 mmol) from step 2,2,3,5-trichloropyridine (420 mg, 0.2.3 mmol), 2N aqueous $K_2PO_4$ (2 mL) and DMF (2 mL). The tube was flushed with $N_2$ and $Pd(PPh_3)_4$ (2.9 mg, 0.025 mmol) was added and the tube was sealed. The reaction mixture was warmed to 65° C. for 16 h, cooled to RT and diluted with $H_2O$ (15 mL). The solution was thrice extracted with EtOAc (5 mL) and the combined extracts dried ($Na_2SO_4$), filtered and concentrated in vacuo. The crude product was purified by flash chromatography over $SiO_2$ (0 to 20% EtOAc/hexane) to afford impure 68 (0.059 g) which was further purified by a second chromatography using the same conditions. The product was dissolved in $Et_2O$ and a 2M solution of HCl in $Et_2O$ was added and the precipitated hydrochloride salt was filtered and dried in vacuo.

Example 24

3-Bromo-7-(3,5-dichloro-pyridin-2-yl)-2-methyl-2H-indazole

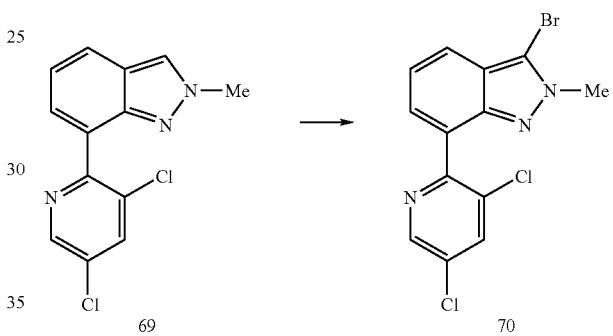

To a solution of 69 (131 mg, 0.47 mmol) and HOAc (5 mL) was added bromine (75 mg, 0.47 mmol) via syringe. The reaction was stirred for 1 h and the solution concentrated in vacuo and diluted with $H_2O$ (10 mL). The resulting solution was twice extracted with EtOAc (5 mL) and the combined extracts dried (MgSO4), filtered and evaporated to afford a brown oil. The crude product was purified by flash chromatography over $SiO_2$ (0 to 50% EtOAc/hexane) to afford 70 (0.096 g).

Example 25

[7-(2,4-Dichloro-phenyl)-2-methyl-2H-indazol-3-yl]-acetonitrile

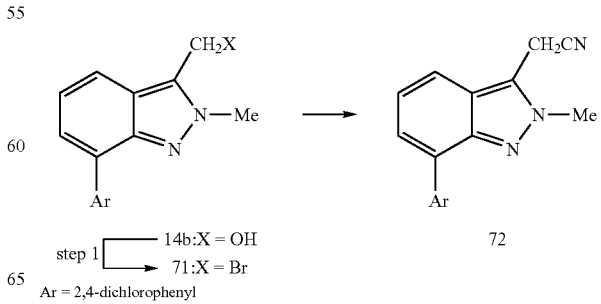

Step 1

The alcohol 14b (257 mg, 0.836 mmol) was suspended in $CHCl_3$ (5 mL) and cooled to 0° C. and $PBr_3$ (0.09 mL, 0.947 mmol) was added slowly. The mixture was stirred at 0° C. for 3.5 h and quenched with ice-water. The mixture was twice with EtOAc and the combined extracts were washed with water, dried ($MgSO_4$). The solvent was removed in vacuo to afford 71 (315 mg, 100% theory) which was used in the next step without further purification.

Step 2

Bromide 71 (0.315 g, 0.85 mmol) was dissolved in NMP (5 mL) and cooled to 0° C. To the solution was added NaCN (0.210 g, 4.29 mmol) and the reaction was stirred for 2 h and quenched with ice-water. The mixture was twice extracted with EtOAc and the combined extracts were washed with brine for four times, dried ($MgSO_4$), filtered and concentrated in vacuo. The crude product was purified by flash chromatography on $SiO_2$ (20 to 30% EtOAc/hexane in a linear gradient over 30 min) to afford 72 (0.096 g, 36% theory).

Example 26

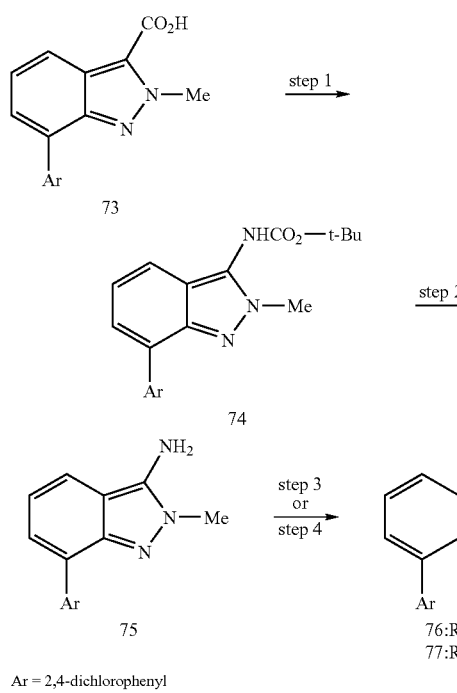

Ar = 2,4-dichlorophenyl

Step 1

A flask was charged with 3-carboxy-7-(2,4-dichlorophenyl)-2-methyl indazole (73, 1.386 g, 4.32 mmol), toluene (12.5 mL) and tert-butanol (12.5 mL). To the resulting solution was added TEA (1.80 mL, 12.95 mmol) and diphenylphosphoryl azide (2.79 mL, 12.95 mmol). The reaction mixture was heated at 100° C. for 22 h, cooled and diluted with EtOAc (50 mL). The resulting solution was twice washed with water and once with brine (50 mL). The resulting organic phase was dried ($MgSO_4$), filtered and evaporated to afford a brown oil which was purified by flash chromatography on $SiO_2$ (0-30% EtOAc/hexane) to afford 74 (1.28 g, 70% theory)

Step 2

A solution of 74 (0.5 g, 1.28 mmol), TFA (3 mL) and DCM (5 mL) was stirred at RT for 7 h. To the solution was added 1M NaOH (10 mL) and 50% NaOH (5 mL). The resulting solution was thrice extracted with DCM (20 mL), dried ($MgSO_4$), filtered and evaporated to afford 75 (346.2 g, 93% theory) as a white solid.

Step 3

To a solution of 75 (0.100 g, 0.35 mmol) and DCM (2 mL) and pyridine (0.1 mL) was added methanesulfonyl chloride (0.43 g, 0.37 mmol). The reaction was stirred for 5 h and the reaction was quenched with $H_2O$ (10 mL). The resulting solution was twice extracted with EtOAc (25 mL) and the combined extracts were dried ($MgSO_4$), filtered and evaporated. The crude product was purified by flash chromatography on $SiO_2$ (0-50% EtOAc/hexane) to afford 76 (89 mg, 70% theory).

Step 4

To a solution of 75 (0.100 g, 0.35 mmol) and dichloroethane (2 mL) was added (35 mg, 0.37 mmol) via syringe. The reaction mixture was stirred overnight at RT and quenched by addition of saturated $NaHCO_3$ (10 mL). The resulting solution was thrice extracted with EtOAc (30 mL) and the combined extracts were dried ($MgSO_4$), filtered and evaporated. The crude product was purified by flash chromatography on $SiO_2$ (0-50% EtOAc/hexane) to afford 77.

Example 27

[7-(2,4-Dichloro-phenyl)-2-methyl-2H-indazol-3-yl]-urea. (75) and 3-[7-(2,4-Dichloro-phenyl)-2-methyl-2H-indazol-3-yl]-1,1-dimethyl-urea (76)

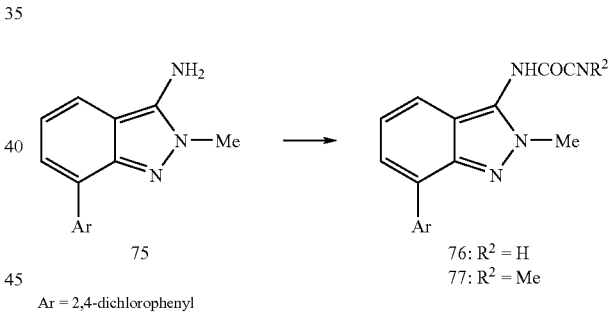

Ar = 2,4-dichlorophenyl

76: $R^2$ = H
77: $R^2$ = Me

A solution of 7-(2,4-dichloro-phenyl)-2-methyl-2H-indazol-3-ylamine (0.050 g, 0.17 mmole) in DCM (5 mL) was treated with trichloroacetyl isocyanate (0.022 mL, 0.035 g, 0.188 mmole) and the solution was stirred at RT under a nitrogen atmosphere for 1 h. The reaction mixture was concentrated in vacuo the residue was dissolved in MeOH (5 mL) and $K_2CO_3$ (0.1 g, 0.72 mmole) was added and the heterogeneous mixture stirred at RT for 1 h. The solvent was evaporated and $H_2O$ (30 mL) was added and the precipitated solid was filtered, and dried. Crystallization from MeOH/$Et_2O$ afforded 76 (0.049 g, 49% theory, m.p. >300° C.) as a white solid.

A suspension of 75 (0.100 g, 0.342 mmole) and 10 mL of toluene under a nitrogen atmosphere was treated with $AlMe_3$ (0.46 ml, 0.92 mmole, 2M in toluene) and the solid slowly dissolved resulting in a grayish green solution. After 10 min at RT the mixture was treated with dimethylcarbamoyl chloride (0.085 ml, 0.099 g, 0.92 mmole) and heated to 100° C. for 8 h. The reaction mixture was cooled to RT, treated with H$_2$O (50 mL) and saturated NaHCO$_3$ (25 mL) solution, thrice extracted with EtOAc (25 ml). The combined extracts were washed with brine (50 mL), dried (MgSO$_4$), filtered and evaporated to dryness. The residue was purified by flash column chromatography on SiO$_2$ (acetone/CH$_2$Cl$_2$, 15:85) to afford 77 (0.085 g, 60% yield, m.p. 123-126° C.) as a brown solid.

Example 28

N-[7-(2,4-Dichloro-phenyl)-2-methyl-2H-indazol-3-ylmethyl]-N-methyl-acetamide

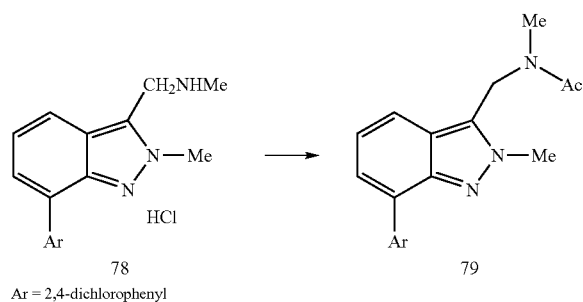

Ar = 2,4-dichlorophenyl

The amine hydrochloride 78 (0.0254 g, 0.064 mmol) was dissolved in pyridine (1 mL) and Ac$_2$O (0.2 mL, 2.12 mmol) was added. The mixture was stirred at RT for 72 h and partitioned between EtOAc and 10% aqueous HCl. The organic phase was washed with H$_2$O, brine, dried (MgSO$_4$) and concentrated in vacuo. The crude product was purified by flash chromatography on SiO$_2$ (2% MeOH in CH$_2$Cl$_2$ containing 0.15% NH$_4$OH to afford 79 (0.023 g, 99% theory).

Example 29

[7-(2,4-Dichloro-phenyl)-2-methyl-2H-indazol-3-ylmethyl]-carbamic acid methyl ester; hydrochloride

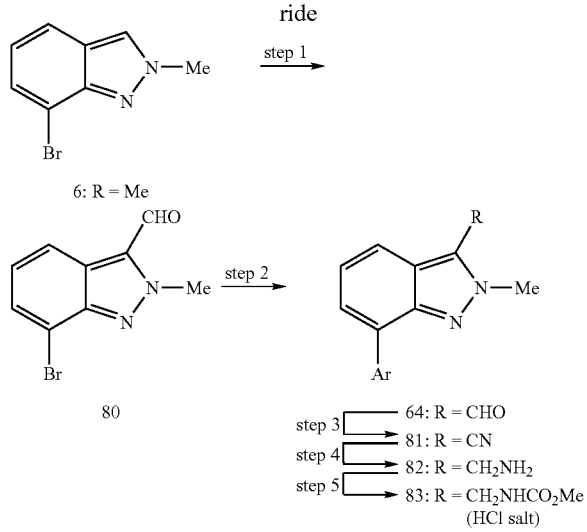

Ar = 2,4-dichlorophenyl

Step 1

To a solution of 7-bromo-2-methyl-indazole (6, R=Me, 3.20 g, 15.16 mmol) and dry THF (50 mL) which was cooled to −78° C. and maintained under an N$_2$ atmosphere was added dropwise LDA (12.0 mL, 22.74 mmol, 2.0M solution in heptane/THF/ethylbenzene). After the addition was completed the reaction mixture was stirred for 10 min and warmed to 0° C. for 20 min. The dark red solution was cooled to −78° C. and DMF (3.0 mL, 45.48 mmol) was added dropwise. The solution was allowed to warm to RT and stirred overnight. The reaction was quenched by the addition of saturated NH$_4$Cl (50 mL) and the resulting solution was twice extracted with EtOAc. The combined extracts were dried (MgSO$_4$), filtered and evaporated. The crude product was purified by flash chromatography on SiO$_2$ (0 to 40% EtOAc/heptane in a linear gradient over 20 min) to afford 0.890 g of solid which was a mixture of starting material and the desired product. The reaction was rechromatographed on SiO$_2$ (0 to 20% EtOAc/heptane in a linear gradient over 20 min) to afford pure 80 (0.470 g) as solid. A second fraction contained 1.22 g of a mixture of starting material and the desired product.

Step 2

A round bottom flask was charged with 80 (1.36 g, 5.69 mmol), 2,4-dichlorobenzeneboronic acid (1.411 g, 7.40 mmol), Pd(PPh$_3$)$_4$ (0.1972 g, 0.17 mmol), DME (35.0 mL) and 2M Na$_2$CO$_3$ (8.0 mL). The reaction mixture was heated to 80° C. overnight. During the reaction period solid Na$_2$CO$_3$ precipitated and H$_2$O was added as required to provide a homogenous solution (23 mL). The reaction mixture was cooled to room temperature and diluted with EtOAc. The aqueous phase was twice extracted with EtOAc and the combined organic phases were dried (MgSO$_4$), filtered and concentrated in vacuo. The crude product was purified by flash chromatography on SiO$_2$ (0 to 20% EtOAc/heptane in a linear gradient over 20 min) to afford 64 (1.62 g) as a yellow solid.

Step 3

A suspension of 64 (2.294 g, 2.29 mmol), ammonia (4.6 mL, 9.18 mmol, 2.0 M solution in 2-propanol), MgSO$_4$ (4.14 g, 34.4 mmol) and MnO$_2$ (2.0 g, 23.0 mmol) was stirred overnight at RT. The crude product was purified by flash chromatography on SiO$_2$ (0 to 10% EtOAc/hexane in a linear gradient over 20 min) to afford 81 (0.428 g) as a white solid.

Step 4

To a vigorously stirred ice-cold solution of 81 (0.100 g, 0.331 mmol), CoCl$_2$.6H$_2$O (0.008 g, 0.033 mmol), THF (1.0 mL) and H$_2$O (0.5 mL) was added NaBH$_4$ (0.275 g, 0.728 mmol) portionwise over a 5 min period. The reaction was allowed to come to RT and stirred for 2 h. The suspended black solid was filtered and the reaction mixture concentrated in vacuo. The residual aqueous phase was twice extracted with EtOAc and the combined organic extracts dried (MgSO$_4$), filtered and concentrated in vacuo. The crude product was purified by flash chromatography on SiO$_2$ (0 to 100% EtOAc/hexane in a linear gradient over 10 min) to afford 82 (0.073 g) as a white solid.

Step 5

To a solution of 82 (0.073 g, 0.238 mmol) and Et$_2$O (1.5 mL) was added sequentially TEA (66.0 µL, 0.478 mmol) and methyl chloroformate (27.63 µL, 0.358 mmol). The resulting mixture was stirred at RT for 2.5 h. The reaction mixture was diluted with H$_2$O and twice extracted with EtOAc (25 mL). The combined extracts were dried (MgSO$_4$), filtered and evaporated. The crude product was purified by flash chromatography on SiO$_2$ (0 to 50% EtOAc/heptane in a linear gradient over 15 min) to afford 0.049 g of white solid which was impure. The resulting solid was further purified by preparative TLC (50% EtOAc/hexane). The oil which was recovered from the preparative plate was dissolved in warm THF and 1.0 M HCl/Et$_2$O solution was added dropwise until the solution reached a nominal pH of about 1. The resulting mixture was stirred for 0.5 h and the white solid which formed was collected by filtration to afford 83 (0.017 g, m.p. 146.3-148.6° C.).

Example 30

[7-(2,4-Dichloro-phenyl)-2-methyl-2H-indazol-3-ylmethyl]-hydrazine; hydrochloride

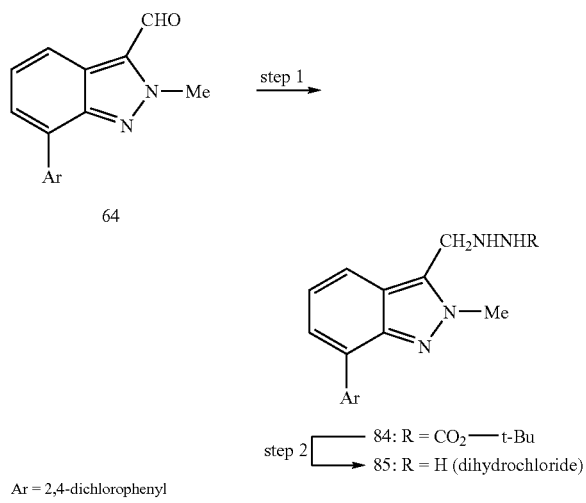

Step 1

A solution of aldehyde 64 (0.700 g, 0.657 mmol), tert-butyl carbazate (0.087 g, 0.657 mmol), THF (5 mL) and MeOH (5 mL) were stirred overnight at 65° C. After 20 h an additional aliquot of tert-butyl carbazate (0.092 g, 0.696 mmol) was added and stirring continued for another 24 h. The reaction was concentrated to a foamy orange solid, which was purified by column chromatography (0 to 50% EtOAc/hexanes) to afford the hydrazone (0.303 g) as a foamy pale yellow solid.

A mixture of NaBH$_3$CN (0.051 g, 0.81 mmol), THF (1 mL) and chlorotrimethylsilane (0.100 mL, 0.788 mmol) was stirred for 10 min. The hydrazone from the previous step was dissolved in THF (4 mL) and added. The pale yellow solution was stirred for 19 h; the reaction was not complete. A second aliquot of NaBH$_3$CN (0.073 g, 1.16 mmol), THF (1 mL), and chlorotrimethylsilane (0.150 mL, 1.18 mmol) was added to the reaction. After 1.25 h, 10% aqueous NaOH (10 mL) was slowly added, and the resulting mixture was extracted with Et$_2$O (10 mL). The organic layer was washed with 10 mL of a saturated aqueous NaCl solution, dried (MgSO$_4$), filtered, and concentrated to a yellow oil. Column chromatography (0 to 50% EtOAc/hexanes) afforded 0.097 g (45%) of slightly impure 84 as a white solid.

Step 2

Acetyl chloride (1 mL) was slowly added to MeOH (4 mL, EXOTHERMIC). The resulting solution was added to slightly impure 84 (0.097 g, 0.23 mmol), and the pale yellow solution was stirred for 17 h then concentrated to a white solid. This solid was partitioned between Et$_2$O (5 mL) and 10% aqueous NaOH solution (5 mL). The aqueous layer was extracted with Et$_2$O (5 mL), and the combined organic layers were washed with saturated brine (10 mL), dried (MgSO$_4$), filtered, and concentrated to 0.050 g of a yellow oil. This oil was dissolved in Et$_2$O (3 mL) and 2.0 M HCl in Et$_2$O (0.2 mL) was added. The resulting mixture was stirred for 30 min. then concentrated to a pale yellow solid. This solid was triturated in 5 mL of hot THF. After cooling to RT, the solid was filtered, rinsing well with Et$_2$O, and dried in air then under vacuum affording 85 (0.036 g, 40%, m.p. 172.5-176.0) as a pale yellow solid.

Example 31

7-(2,4-Dichloro-phenyl)-2-methyl-2H-indazole-3-sulfonic acid amide

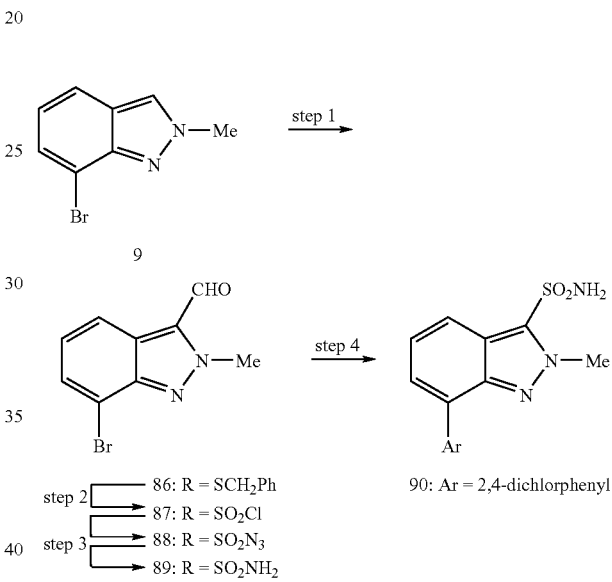

Step 1

To a solution of 7-bromo-2-methyl indazole (9, 3.330 g, 0.0158 mmol) and dry THF (50 mL) cooled to −78° C. was added dropwise LDA (11.50 mL 0.024 mmol, 2.0 M in heptane/THF/ethylbenzene). The dark red solution was stirred at −78° C. for 10 min, then stirred at 0° C. for another 20 min. The reaction mixture was re-cooled to −78° C. and a solution of dibenzyldisulfide (5.83 g, 0.24 mmol) in THF (10 mL) was added dropwise. After the addition was complete the reaction mixture was allowed to stir at RT overnight. The reaction was quenched by addition of 10% NaOH and the aqueous phase was extracted twice with Et$_2$O (25 mL). The combined organic extracts were washed with brine (25 mL), dried (MgSO$_4$), filtered and evaporated. The crude product was purified by silica gel chromatography (0-15% linear gradient over 20 min then 15-25% over 10 min) to afford 86 as a light brown solid (3.07 g).

Step 2

A 100 mL flask was charged with 86 (1.00 g, 3.0 mmol), HOAc (25 mL) and H$_2$O (2.0 mL). The reaction was cooled in an ice-water bath and Cl₂ gas was bubble through the solution via a submersed Pasteur pipette for exactly 10 s. The ice-water bath was removed and the solution was stirred for 2 min whereupon the reaction was quenched by addition of a 10% Na₂S₂O₃ solution (60 mL) was added and the aqueous phase was twice extracted with CH₂Cl₂ (60 mL). The combined extracts were washed with 10% NaOH (60 mL), dried (Na₂SO₄), filter and concentrated in vacuo. The yellow solid was dried in vacuo and chromatographed on SiO₂ (0-5% EtOAc/hexane in a linear gradient over 20 min) to afford 87 (590 mg) as a white solid.

Step 3

To a solution of the sulfonyl chloride 87 (0.725 g. 2.34 mmol), sodium azide (0.152 g, 2.34 mmol), acetone (12 mL) and H₂O (12 mL) was stirred at 0° C. for 2.5 h. The acetone was removed in vacuo and the resulting suspension twice extracted with Et₂O. The combined organic extracts were dried (MgSO₄), filtered and evaporated to afford 88 (0.689 g; m.p. 98.5-99.2° C.) as a white solid which was used in the next step without further purification.

To a solution of 88 (0.650 g, 2.05 mmol), NH₄Cl (0.2562 g, 4.79 mmol), EtOH (26 mL) and H₂O (9 mL) was added zinc metal (0.269 g, 4.112 mmol) and the reaction stirred vigorously at RT overnight. TLC analysis indicated some sulfonyl azide was still present and additional zinc metal (0.1344 g, 2.06 mmol) and NH₄Cl (0.110 g, 2.06 mmol) was added and stirring continued for an additional 24 h at which time no starting material was evident. The reaction mixture was concentrated in vacuo. The residue was diluted with 5% NH₄Cl and twice extracted with EtOAc (25 mL). The combined extracts were washed with brine, dried (MgSO₄), filtered and concentrated in vacuo. The crude product was purified by flash chromatography on SiO₂ (0 to 30% EtOAc/hexane in a linear gradient over 15 min) to afford 89 (0.461 g, m.p. 202.4-205.3° C.) as a white solid.

Step 4

A solution of 89 (0.293 g, 1.01 mmol), 2,4-dichloroboronic acid (0.3854 g, 2.02 mmol), Pd(PPh₃)₄ (0.0351 g, 0.030 mmol), DME (9.0 mL) and 2M Na₂CO₃ (2.20 mL) was heated to 80° C. overnight. An additional aliquot of H₂O (4.5 mL) was added to dissolve Na₂CO₃ which precipitated from the solution.

The reaction mixture was cooled and diluted with EtOAc and the aqueous layer was withdrawn and washed twice with EtOAc. The combined organic extracts were washed with brine, dried (MgSO₄) and concentrated in vacuo. he crude product was purified by flash chromatography on SiO₂ (0 to 15% EtOAc/heptane in a linear gradient over 30 min and isocratically at 15% thereafter) to afford 90 (0.410 g, m.p. 170.4-171.5° C.) as a white solid.

Example 32

7-(2,4-Dichloro-phenyl)-2-methyl-2H-indazole-3-sulfonic acid (2-hydroxy-ethyl)-amide

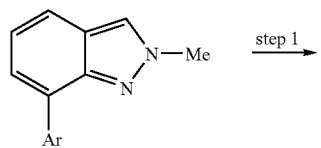

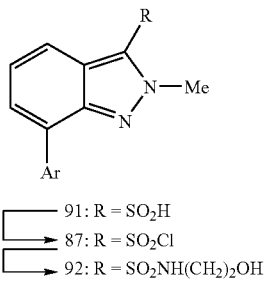

Ar = 2,4-dichlorophenyl

Step 1

A round-bottom flask was charged with 7-(2,4-dichlorophenyl)-2-methyl-indazole (5, 1.750 g, 6.0 mmol), trimethylsilyl chlorosulfonate (2.918 mL, 3.575 g, 19 mmol) and DCE (35 mL), fitted with a condenser and heated to 80° C. overnight with stirring. The reaction mixture was cooled to room temperature and concentrated in vacuo. The resulting orange oil was dissolved in SOCl₂ (10 mL) and DMF (500 µL) was added and the reaction mixture stirred at 80° C. for 2 h. The reaction mixture was concentrated in vacuo and the crude product was purified by flash chromatography on SiO₂ (0 to 15% EtOAc/hexane in a linear gradient over 20 min) to afford 87 (0.365 g) as a yellow oil.

Step 2

To a solution of the sulfonyl chloride 87 (0.030 g, 0.080 mmol) and CH₂Cl₂ (5 mL) was added ethanolamine (10.0 µL, 0.160 mmol) and the reaction mixture was stirred at RT for 1 h. The reaction mixture was concentrated in vacuo and the crude product was purified by flash chromatography on SiO₂ (0 to 80% EtOAc/hexane in a linear gradient over 15 min) to afford 92 (0.014 g, m.p. 202.4-205.3° C.) as a white solid. The product could be further purified by preparative reverse-phase chromatography with MeCN, H₂O and TFA.

The following compounds were prepared from 7-(2,4-dichloro-phenyl)-2-methyl-2H-indazole-3-sulfinyl chloride in a similar fashion by replacing ethanolamine with 2-methoxyethylamine, dimethylamine, methylamine, morpholine, N-methylpiperazine and diethanolamine.

7-(2,4-Dichloro-phenyl)-2-methyl-2H-indazole-3-sulfonic acid (2-methoxy-ethyl)-amide (D7)

7-(2,4-Dichloro-phenyl)-2-methyl-2H-indazole-3-sulfonic acid dimethylamide (D8)

7-(2,4-Dichloro-phenyl)-2-methyl-2H-indazole-3-sulfonic acid methylamide (D9)

7-(2,4-Dichloro-phenyl)-2-methyl-3-(morpholine-4-sulfonyl)-2H-indazole (D10)

7-(2,4-Dichloro-phenyl)-2-methyl-3-(4-methyl-piperazine-1-sulfonyl)-2H-indazole D(11)

7-(2,4-Dichloro-phenyl)-2-methyl-2H-indazole-3-sulfonic acid bis-(2-hydroxy-ethyl)-amide D(12)

Example 33

7-(2,4-Dichloro-phenyl)-3-methanesulfonylmethyl-2-methyl-2H-indazole

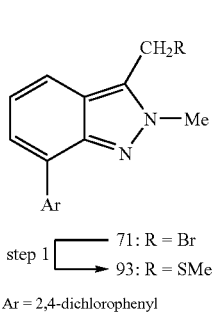 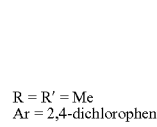 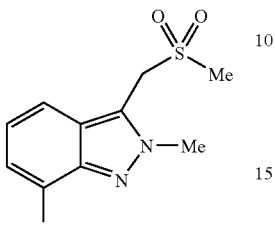

71: R = Br
step 1
93: R = SMe

Ar = 2,4-dichlorophenyl

94

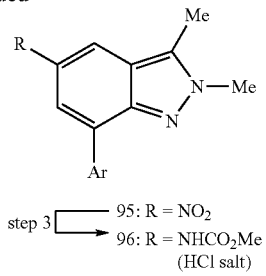

R = R' = Me
Ar = 2,4-dichlorophenyl step 3
95: R = $NO_2$
96: R = $NHCO_2Me$ (HCl salt)

Step 1

To a solution of bromide 71 (0.370 g, 1.00 mmol) and NMP (5 mL) at RT was added NaSMe (0.210 g, 3.00 mmol) and the resulting solution was stirred for 3 h and partitioned between EtOAc and $H_2O$. The aqueous layer was twice extracted with EtOAc. The combined organic extracts were dried ($MgSO_4$), filtered and concentrated in vacuo. The crude product was purified by flash chromatography on $SiO_2$ (15 to 20% EtOAc/hexane in a linear gradient over 30 min) to afford 93 (0.115 g, 34% theory) as an oil.

Step 2

To a solution of sulfide 93 (115 mg, 0.34 mmol) and $CH_2Cl_2$ (2 mL) at RT was added MCPBA (215 mg, <0.96 mmol, <77% assay) and the reaction mixture was stirred overnight. The mixture was partitioned between EtOAc and $NaHCO_3$. The aqueous phase was twice extracted with EtOAc and the combined organic layers were dried ($MgSO_4$), filtered and concentrated in vacuo. The residue was triturated with 20% EtOAc/hexanes and the resulting solid was filtered and air died to afford 94 (0.053 g, 42% theory).

Example 34

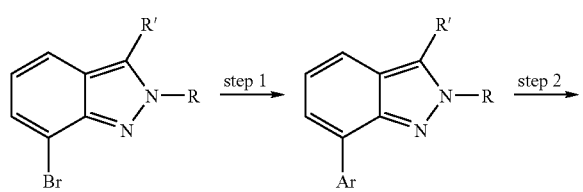

Step 1

A round bottom flask was charged with 7-bromo-2,3-dimethylindazole (8, 2.290 g, 10.17 mmol), 2,4-dichlorobenzeneboronic acid (3.883 g, 20.35 mmol), $Pd(PPh_3)_4$ (0.3525 g, 0.31 mmol), DME (25 mL) and 2M $Na_2CO_3$ (25 mL). The reaction mixture was heated to 80° C. for 72 h. The reaction mixture was cooled to room temperature and diluted with $H_2O$ and twice extracted with EtOAc and the combined organic phases were dried ($MgSO_4$), filtered and concentrated in vacuo. The crude product was purified by flash chromatography on $SiO_2$ (0 to 20% EtOAc/heptane in a linear gradient over 20 min) to afford 7 (2.05 g) as a light-brown oil.

Step 2

A solution of fuming nitric acid (5.30 mL) and $Ac_2O$ (1.8 mL) were stirred at 0° C. for 5 min. To the mixture was added 7 (0.627 g, 2.15 mmol) and the reaction mixture allowed to stir at RT for 2 h. The reaction mixture was cooled to 0° C. and carefully quenched with 50% NaOH and the aqueous layer was twice extracted with EtOAc and the combined organic phases were dried ($MgSO_4$), filtered and concentrated in vacuo to afford 95 (0.682 g) as a yellow solid.

Step 3

To a vigorously stirred mixture of 95 (0.100 g, 0.297 mmol) and tin (0.1624 g, 1.368 mmol) was added con HCl in three equal portions. After the exothermic reaction subsided, EtOH (2.0 mL) was added and the reaction was heated at 80° C. for 1 h. The reaction mixture was concentrated in vacuo and the residue was mixed carefully with 2N NaOH and twice extracted with $Et_2O$. The combined organic phases were dried ($MgSO_4$) and filtered.

To the $Et_2O$ solutions from the reduction reaction was added sequentially TEA (82.9 pt., 0.595 mmol) and methyl chloroformate (45.9 μL). The resulting mixture was stirred at RT for 3 h. The reaction mixture was neutralized with $NaHCO_3$ the resulting aqueous phase was twice extracted with EtOAc and the combined organic phases were dried ($MgSO_4$), filtered and concentrated in vacuo. The crude product was purified by flash chromatography on $SiO_2$ (0 to 30% EtOAc/heptane in a linear gradient over 20 min) to afford 0.021 g of a slightly impure yellow solid. The yellow solid was dissolved in $Et_2O$ and 1.0 M HCl/$Et_2O$ solution was added dropwise The resulting solid was collected by filtration to afford 96 (0.0107 g).

Example 35

7-(2,4-Dichloro-phenyl)-2-methyl-2H-pyrazolo[4,3-c]pyridine

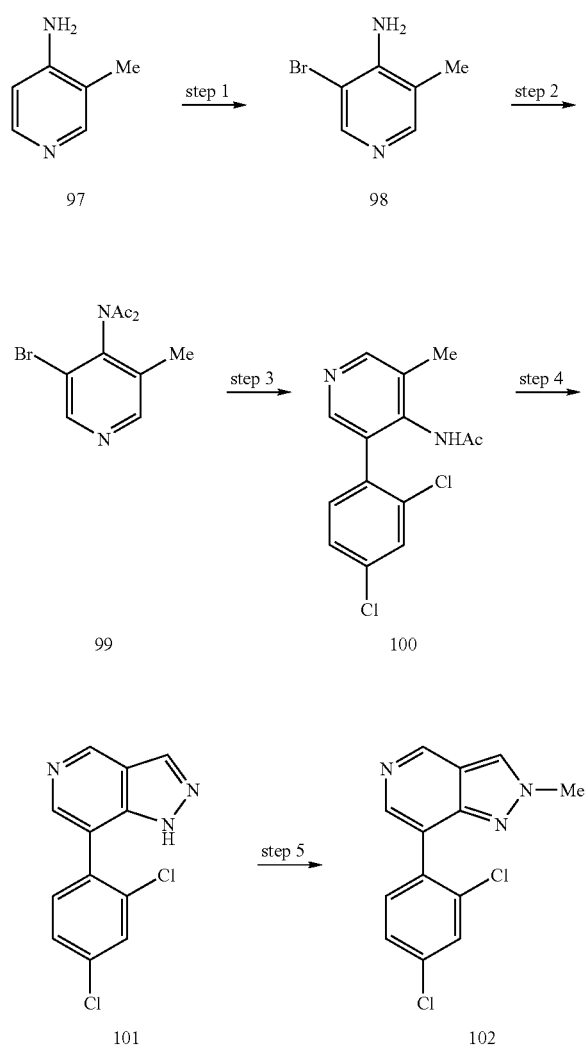

Step 1

To a solution of 4-amino-3-picoline (97, 10 g, 0.092 mmol) and HBr (50 mL) heated to 70° C. was added 15% H₂O₂ (16 mL) over a 1 h period. The reaction mixture was stirred for additional h and poured in ice (100 g). The pH of the solution was adjusted to about 5 with 50% NaOH and the resulting red precipitate was filtered. The pH was raised to about 9 and the resulting white precipitate was collected by filtration to afford 98 (13.5 g, 78% theory)

Step 2

A suspension of 98 and toluene (100 mL) was heated to 110° C. until the solid dissolved. The warm solution was added TEA (30 mL, 0.216 mmol) and acetic anhydride (20.4 mL, 22.1 g, 0.216 mmol) and the reaction was heated for 3 h. An additional 30 mL of Ac₂O was added after 3 h and an additional 30 mL of TEA was added after 6 h. The solution was concentrated in vacuo and the residue dissolved in EtOAc (500 mL) and was twice with H₂O (200 mL). The aqueous extracts were reextracted twice with EtOAc (200 mL) and the combined EtOAc extracts were dried (MgSO₄), filtered and evaporated to afford a brown oil. The crude product was purified by flash chromatography over SiO₂ (0 to 20% EtOAc/hexane) to afford an impure yellow oil which was subjected to a second flash chromatography over SiO₂ (20 to 50% EtOAc/hexane) to afford 99 (12.1 g).

Step 3

A 100 mL round bottom was charged with 99 (630 mg, 2.3 mmol) 2,4 dichlorobenzene boronic acid (662 mg, 3.5 mmol), 2N aqueous Na₂CO₃ (15 mL) and DME (15 mL). The tube was flushed with N₂ and Pd(PPh₃)₄ (79 mg, 0.07 mmol) was added. The reaction mixture was warmed to 85° C. for 24 h, cooled to RT and diluted with EtOAc (100 mL). The solution was twice washed with brine (20 mL) and the organic layer dried (Na₂SO₄), filtered and concentrated in vacuo. The crude product was purified by flash chromatography over SiO₂ (0 to 50% EtOAc/hexane) to afford pure 100 (0.154 g, 22% theory)

Step 4

To a solution of 100 (1.5 g, 5.08 mmol) and benzene (100 mL) was added to KOAc (1.4 g, 5.84 mmol) and Ac₂O (1.30 mL, 1.4 g, 13.73 mmol). The solution was warmed to 90° C. and isoamyl nitrite (1.37 mL, 10.16 mmol) was added via syringe. The reaction was heated for 5.5 h, cooled to RT and the mixture concentrated in vacuo. To the residual material was added MeOH (15 mL) and LiOH (20.32 mmol) and the resulting mixture was heated to reflux for 1 h. The reaction was allowed to age at RT overnight then heated for an additional 1 h. To the solution was added 5 g of silica gel and the solvent was evaporated. The crude product adsorbed onto silica was added to the top of a SiO2 column and purified by flash chromatography (0 to 50% EtOAc/hexane) to afford indazole 101 (0.570 g, 42% theory).

Step 5

To a solution of 101 (0.285 g, 21.08 mmol) and DMF (5 mL) was added NaH (0.060 g, 1.51 mmol, 60% in mineral oil). When gas evolution ceased, dimethyl sulfate (0.136 g, 1.08 mmol) was added and the reaction mixture stirred for an addition 0.5 h. The reaction was quenched by addition of H₂O (20 mL) and thrice extracted with EtOAc (30 mL). The combined extracts were dried (MgSO₄), filtered and evaporated to afford a brown solid which contained both isomeric N-methyl compounds. The crude product was purified by flash chromatography on SiO₂ (20-70% EtOAc/hexane). The first fraction contained the 1-methyl isomer and the second fraction contained the 2-methyl isomer. The second fraction was further purified by a second column to afford 102 (0.103 g).

Example 36

7-(2,4-Dichloro-phenyl)-2-methyl-2H-pyrazolo[4,3-b]pyridine

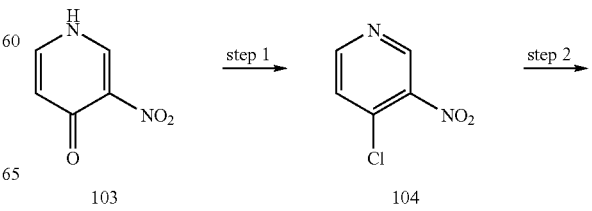

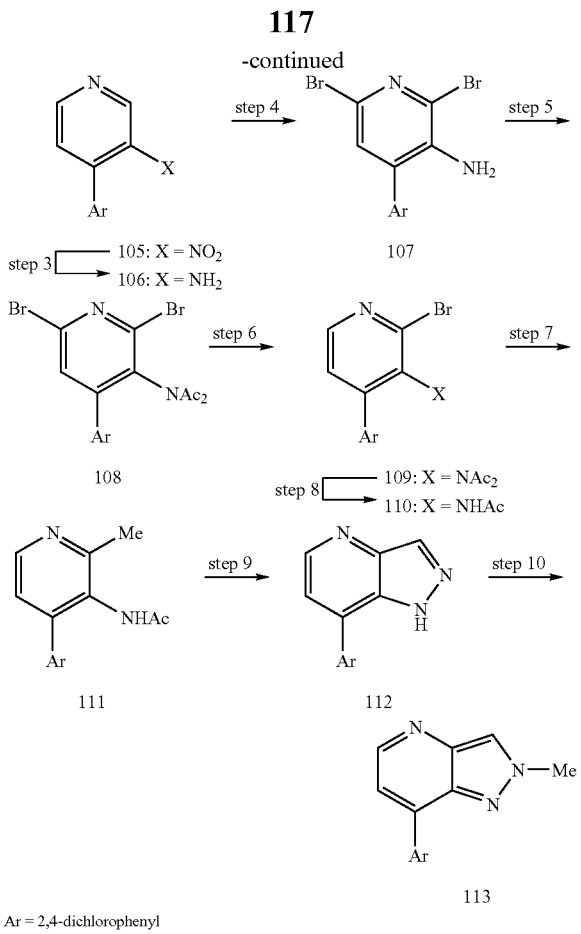

Ar = 2,4-dichlorophenyl

Step 1

A mixture of POCl₃ (22 mL) and PCl₅ (15 g) was warmed to 70° C. and 4-hydroxy-3-nitropyridine (103, 10 g) was added in small portions. A white solid formed and evolution of gas occurred. After the addition was completed the reaction was warmed to 140° C. and the reaction stirred for 5 h. The reaction mixture was cooled and concentrated in vacuo. To the residue was added carefully H$_2$O (50 mL) and the pH adjusted to 7.5 with solid Na$_2$CO$_3$. DCM was added and the two-phase mixture stirred for 30 min. The phases were separated and the aqueous phase washed twice with DCM (50 mL). The combined organic phases were dried (MgSO$_4$), filtered and evaporated to afford 104 (8.72 g, 77% theory) which was sufficiently pure to use in the next step.

Step 2

A 500 mL round bottom flask was charged with 104 (6.794 g, 42.9 mmol), 2,4-dichloroboronic acid (8.24 g, 43.2 mmol), Pd(PPh$_3$)$_4$ (2.897 g, 2.51 mmol), DMF (200 mL) and 2M K$_2$HPO$_4$ (128 mL) and the reaction mixture was warmed to 68° C. under an N$_2$ atmosphere for 21 h. The reaction mixture was diluted with H$_2$O (1 L) and the yellow precipitate was filtered, air-dried and dried under high vacuum to afford 10.07 g of crude product which was purified by flash chromatography on SiO$_2$ (20% EtOAc/hexane) to afford 6.002 g (52%) of slightly impure 105 as a yellow solid.

Step 3

A solution of 105 (5.935 g, 22.06 mmol), EtOH (26 mL) and H$_2$O (11 mL) was heated to 90° C. and iron powder (1.85 g, 33.25 mmol) and con HCl (0.4 mL) were carefully added. The reaction was stirred for 2 h and quenched with 10% NaOH solution (10 mL), then stirred an additional 10 min before being allowed to cool to room temperature. The reaction mixture was filtered through CELITE 521® and the filter pad washed thoroughly with MeOH. The filtrate was concentrated in vacuo and partitioned between H$_2$O (20 mL) and DCM (20 mL). The aqueous phase was extracted twice with DCM (20 mL) and the combined organic layers dried (MgSO4), filtered and evaporated to afford 5.809 g of crude product which contained significant quantities of starting material. The process was repeated with 7.96 g of iron powder con HCl (2 mL). The reaction was worked up as described previously to afford 106 (4.360 g) 83% impure as an orange resin.

Step 4

To a solution of 106 (2.178 g 9.11 mmol) and HOAc (20 mL) was added dropwise over ca. 1 min bromine (0.94 mL, 18 mmol). The reaction mixture was stirred for 23 h at RT and then concentrated in vacuo. The crude product was purified by flash chromatography on SiO$_2$ (10% EtOAc/hexane) to afford 107 (0.959 g) (27%) as a yellow-orange solid.

Step 5

A solution of 107 (0.050 g, 0.13 mmol), Ac$_2$O (0.5 mL) and methanesulfonic acid (1 drop) was heated at 130° C. overnight. The reaction mixture was concentrated in vacuo and dissolved in DCM (5 mL) and washed with saturated NaHCO$_3$ (5 mL), dried (MgSO$_4$) filtered and evaporated to afford 108 (0.072 g) ("118%") of a yellow oil which solidified on standing.

Step 6

A 35 mL three neck flask was fitted with a stir-bar, vacuum outlet and a hydrogen-filled balloon and charged with 108 (0.058 g, 0.121 mmol), THF (2 mL) and 10% Pd/C (0.062 g), The vessel was evacuated and filled with H$_2$. After 4 h the H$_2$ was evacuated and MeOH (1 mL) was added, then the vessel was evacuated and filled with H$_2$. After an additional 4 h the reaction was stopped by removing the H$_2$ and the reaction allowed to stand at RT overnight. The reaction mixture was filtered through a pad of CELITE 521® and washed with MeOH. The solvents were removed in vacuo and the crude product was purified by flash chromatography on SiO$_2$ (0 to 10% EtOAc/hexane) to afford 109 (0.020 g) (49% 2-step) as a white solid.

Step 7

A solution of 109 (0.410 g, 1.02 mmol), EtOH (4 mL) and pyrrolidine (1 mL) was stirred for 15 min. The volatile solvents were removed in vacuo and the resulting yellow oil was purified by flash chromatography on SiO$_2$ (0 to 33% EtOAc/hexane) to afford 110 (0.303 g) (83%) as a white solid.

Step 8

A flask was fitted with a stir bar and a condenser and charged with 110 (0.295 g, 0.819 mmol), dioxane (2.7 mL), H$_2$O (0.3 mL), K$_2$CO$_3$ (0.395 g, 2.86 mmol), PdCl$_2$(dppf) (0.068 g, 0.083 mmol) and trimethyl boroxine (0.120 mL, 0.858 mmol). The reaction mixture was heated at 93° C. for 2.5 h, cooled and the solution partitioned between H$_2$O (10 mL) and EtOAc (10 mL). The aqueous phase was extracted with EtOAc (10 mL) and the combined extracts dried (MgSO$_4$), filtered and concentrated in vacuo. The crude yellow oil was purified by flash chromatography on SiO$_2$ (100% EtOAc/hexane) to afford 111 (0.184 g, 76% theory) as a yellow oil.

Step 9

To a solution of 111 (0.180 g, 0.610 mmol), benzene (10 mL), Ac$_2$O (0.18 mL, 1.9 mmol) and KOAc (0.072 g, 0.734 mmol) heated to 79° C. was added isoamyl nitrite (0.13 mL, 0.971 mmol) and the reaction mixture stirred for 14.5 h then cooled to RT and concentrated in vacuo to afford a yellow solid. The residue was taken up in H$_2$O (2 mL), EtOH (6 mL) and LiOH—H$_2$O (0.084 g, 2.00 mmol) and heated at 79° C. for 3 h. The mixture was cooled, concentrated in vacuo and the residue partitioned between H$_2$O (5 mL) and Et$_2$O (5 mL). The aqueous phase was extracted with Et$_2$O and the combined organic extracts washed with brine (10 mL), filtered and evaporated. The resulting orange oil was purified by flash chromatography on SiO$_2$ (0 to 50% EtOAc/hexane) to afford 112 (0.096 g) (60%) as a yellow foam.

Step 10

To an ice-cold solution of 112 (0.093 g, 0.352 mmol) and THF (4 mL) was added NaH (0.020 g, 0.50 mmol). The initially bubbling solution was stirred for 15 min., then dimethyl sulfate (0.033 mL, 0.35 mmol) was added and the reaction removed from the ice-bath and stirred for 0.5 h. The reaction was quenched by addition of SiO$_2$ and concentrated in vacuo. The silica gel was placed on top of a flash column (0 to 66% EtOAc/hexane) to afford 113 as a yellow solid which solidified on standing (0.057 g, 21% theory).

Example 37

7-(2,4-Dichloro-phenyl)-2-methyl-2H-pyrazolo[3,4-c]pyridine; hydrochloride

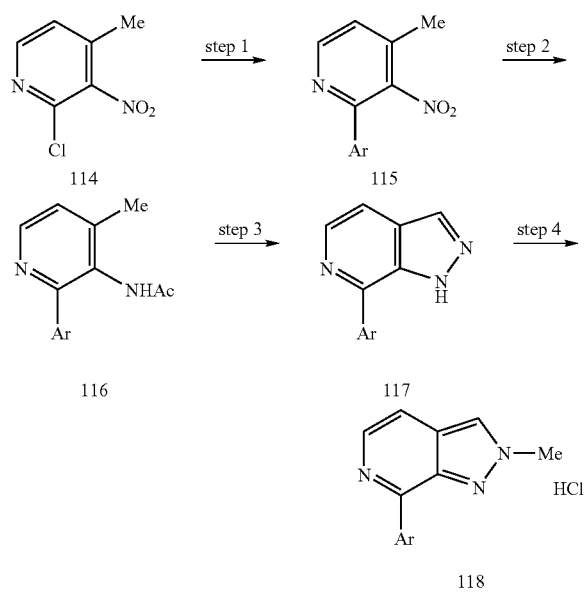

Ar = 2,4-dichlorophenyl

Step 1

A solution of 2-chloro-4-methyl-3-nitro-pyridine (114, 1.08 g, 6.24 mmol), Pd(PPh$_3$)$_4$ (0.405 g, 0.350 mmol), 2,4-dichlorobenzeneboronic acid (1.264 g, 6.62 mmol), DMF (40 mL) and 2 M K$_2$HPO$_4$ (20 mL, 40 mmol) under an N$_2$ atmosphere was heated at 70° C. for 41 h. The reaction mixture was cooled to RT and partitioned between H$_2$O (200 mL) and Et$_2$O (200 mL). The organic phase was washed with H$_2$O (200 mL), brine (200 mL), dried (MgSO$_4$), filtered and concentrated in vacuo. The resulting yellow oil was purified by flash chromatography on SiO$_2$ (0 to 20% EtOAc/hexane) to afford 115 (1.193 g) (68%) as a yellow oil which was sufficiently pure to use in the next step.

Step 2

A solution of 115 (1.148 g, 4.05 mmol) EtOH (10 mL), H$_2$O (2.5 mL) and con HCl (0.5 mL) was heated to 85° C. and iron powder (1.371 g, 24.55 mmol,) was added. The reaction mixture was stirred with continued heating for 1 h, cooled and filtered through CELITE 521®. The filter pad was washed well with MeOH and the volatile solvents removed in vacuo. The red residue was partition between EtOAc (50 mL) and saturated NaHCO$_3$ (50 mL). The organic phase was washed with brine (50 mL), dried (MgSO$_4$), filtered and evaporated. The residue was dissolved in toluene (10 mL) and acetic anhydride (0.41 mL) and heated at 100° C. for 22 h. The reaction mixture was cooled and the volatile solvents removed in vacuo. The dark yellow residue was purified by flash chromatography on SiO$_2$ (50 to 66% EtOAc/hexane) to afford 116 (0.815 g 68%) as a white solid.

Step 3

To a solution of 116 (0.787 g, 2.67 mmol), benzene (30 mL), Ac$_2$O (0.780 mL, 8.27 mmol) and HOAc (0.330 g, 3.36 mmol) was heated to 78° C. and isoamyl nitrite (0.572 mL, 4.27 mmol) was added. The reaction mixture was heated for 22 h, cooled, filtered and concentrated in vacuo. The resulting oil (1.063 g) was dissolved in EtOH (21 mL), H$_2$O (7 mL) and LiOH—H$_2$O (0.339 g, 8.08 mmol) was added. The reaction mixture was heated to 80° C. for 3 h, cooled and concentrated in vacuo. The orange residue was partition between Et$_2$O (50 mL) and 10% NaOH (50 mL). The aqueous phase was extracted with Et$_2$O (50 mL) and the combined organic extracts were washed with brine (100 mL), dried (MgSO$_4$), filter and concentrated in vacuo. The crude product was purified by flash chromatography on SiO$_2$ (0 to 20% EtOAc/hexane) to afford 117 (0.484 g, 69%) as a pale yellow foam.

Step 4

To a solution of 117 (0.107 g, 0.405 mmol) and THF (4 mL) was added NaH (0.020 g, 0.50 mmol, 60% mineral oil dispersion). After stirring for 3 h, dimethyl sulfate (0.040 mL, 0.42 mmol) was added and the mixture stirred for 0.5 h. The reaction was quenched with SiO$_2$ and concentrated in vacuo. The SiO2 was placed on a flash column (0 to 50% EtOAc/hexane) to afford 118 (0.029 g) (26%) as a milky film. The product was dissolved in Et$_2$O (1 mL) and 2.0 M HCl/Et$_2$O solution was added. The resulting white suspension was stirred for 15 min, concentrated and dried in vacuo overnight to afford the hydrochloride salt of 118 (0.031 g) as an off-white solid.

Example 38

35S-TBPS Binding Assay

The binding assay is based on the assay reported by K. Gee et al., *Eur. J. Pharmacol.* 1987 136:419-423.

Homogenate preparation: Membrane preparations of HEK293 cells containing either GABA$_A$ $\alpha_1\beta_2\gamma_2$ or GABA$_A$ $\alpha_2\beta_3\gamma_2$ constructs were performed according to a modified procedure previously described by Gee et al. (supra). Whole HEK 293 cells in D-PBS (calcium/magnesium free) buffer adjusted to pH 7.4 were centrifuged at 7,280×g for 20 m.

After discarding the supernatant, the pellet was resuspended in the buffer and centrifuged at 1,820×g for 10 m. Afterwards, the supernatant was discarded and the pellet resuspended in ice-cold preparation buffer (50 mM Tris HCl pH 7.4, 4° C. and 150 mM KCl), homogenized for 30 sec using a Brinkmann Polytron PT3000 (setting 6) and centrifuged at 48,000×g for 30 m at 4° C. The centrifugation and homogenization procedure was repeated two more times for a total of 3 times before resuspending the membranes at a final protein concentration of 0.5 mg/mL. Aliquots (30 mL) of the final membrane preparation were then centrifuged at 48,000×g for 30 m, and the resulting pellets were stored at −80° C. until required.

$^{35}$S-TBPS binding assay. Membrane pellets containing either $GABA_A$ $\alpha_1\beta_2\gamma_2$ or $GABA_A$ $\alpha_2\beta_3\gamma_2$ constructs were thawed on ice, resuspended in 10 mL of 50 mM Tris HCl pH 7.4, 4° C. and 150 mM KCl and centrifuged at 48,000×g, 30 m at 4° C. After discarding the supernatant, the pellet was resuspended in 30 mL incubation buffer (50 mM Tris HCl pH 7.4, 25° C. and 150 mM KCl) at approximately 0.5 mg/mL protein concentration. In $^{35}$S-TBPS competition studies, HEK293 membranes were incubated with $^{35}$S-TBPS (5 nM final) and GABA (1 µM) in the absence or presence of competitor at concentrations ranging from 0.01 nM to 10 µM in 125 µL incubation buffer for 2 hours at room temperature (~22° C.). Non-specific binding was assayed with picrotoxin (100 µM final concentration). The binding reaction was terminated by vacuum filtration through GF/B filters previously soaked in 0.1% polyethylenimine followed by 3×1 mL washes with ice cold wash buffer (50 mM Tris HCl pH7.4, 4° C. and 150 mM KCl). Measurement of bound radioactivity was performed using a Packard Microplate 96 well topcount scintillation counter. Analysis of competition curves and estimation of $pIC_{50}$ values of test compounds were performed using the software programs ActivityBase and/or Prism (version 3.0).

| compound | $pIC_{50}$ | |
|---|---|---|
| | $\alpha_1\beta_2\gamma_2$ | $\alpha_2\beta_3\gamma_2$ |
| A27 | 6.24 | 7.87 |
| A14 | 6.53 | 7.51 |
| A17 | 5.93 | 7.58 |

Example 39

Pharmaceutical compositions containing the subject compounds for administration via several routes are prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
| --- | --- |
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various modifications may be made to adapt a particular situation, compound, composition, process, process step or steps, to the objective spirit and scope of the present invention as defined in the claims. Such modifications may be made without departing from the true spirit and scope of the invention which should be determined with reference to the following claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound of Formula I:

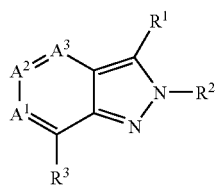

(I)

wherein:
$R^1$ is $CHR^fR^g$, $C_{2-10}$ alkynyl, $C_{1-6}$ haloalkyl, halogen, cyano, —C(=Z)R°, —X²C(=O)X¹R^f, —NR^fSO_2R°, —N[C(=O)OR^m]_2, —N=CR^fNR^jR^k, —S(O)_mR^b, CONR^iNHR° or $C_{1-10}$ alkyl wherein 2 or 3 nonadjacent carbon atoms in the alkyl chain can be replaced with —O—, —S— or —NR^f;
$R^2$ is hydrogen, $C_{1-6}$ alkyl, $C_{3-6}$ cycloalkyl, $C_{3-6}$ cycloalkyl-$C_{1-3}$ alkyl, $C_{1-3}$alkoxycarbonyl-$C_{1-3}$ alkyl, $C_{1-6}$ haloalkyl, or aralkyl;
$R^3$ is aryl or heteroaryl, each optionally substituted with one or more substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —NR^{a''}R^{b''}, where R^{a''} and R^{b''} are each independently selected from the group consisting of hydrogen, $C_{1-9}$ alkyl, and $C_{1-9}$ alkylcarbonyl;
$R^f$ is hydrogen or $C_{1-10}$ alkyl;
$R^g$ is $C_{2-10}$ alkenyl, —NHNH_2, cyano, —OC(=O)R^f, —S(O)^nR^b or —X²(C=O)X¹R^f;
$R^h$ is $C_{1-6}$ alkyl, $C_{1-6}$ heteroalkyl, $C_{2-6}$ alkenyl, NR^jR^k or phenyl optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen;
$R^i$ is R°, hydrogen, $C_{3-6}$ cycloalkyl or $C_{3-6}$ cycloalkyl-$C_{1-3}$ alkyl;
$R^j$ and $R^k$ are (i) independently hydrogen, $C_{1-6}$ alkyl, $C_{1-6}$ heteroalkyl, or (ii) taken together along with the nitrogen atom to which they are attached are $C_{4-6}$ alkylene or $(CH_2)_2X^1(CH_2)_2$;
$R^m$ is $C_{1-10}$ alkyl;
$R°$ is $C_{1-6}$ alkyl, $C_{2-6}$ alkenyl or phenyl optionally substituted with one or more substituents independently selected from the group consisting of $C_{1-6}$ alkyl, haloalkyl, $C_{1-6}$ alkoxy, amino, $C_{1-6}$ alkylamino, $C_{1-6}$ dialkylamino, hydroxyalkyl, cyano, acylamino, alkylsulfonyl, alkylsulfonyloxy, and halogen;
$X^1$ and $X^2$ are independently —O— or —NR^{f1}— wherein at each occurrence R^{f1} is an independently selected R^f radical, or if R^f and R^{f1} are attached to the same nitrogen atom, R^f and R^{f1} can, in addition, be taken together as $C_{4-6}$ alkylene or $(CH_2)_2X^1(CH_2)_2$;
Z is O or NOR°;
m is an integer from 0 to 2;
$A^1$, $A^2$ and $A^3$ are independently CH or N with the proviso that at least two of $A^1$, $A^2$ and $A^3$ are $CH^4$; and,
individual isomers, racemic or non-racemic mixtures of isomers, solvates, hydrates or pharmaceutically acceptable salts thereof.

2. A compound of claim 1 wherein:
$R^1$ is $CHR^fR^g$, $C_{2-10}$ alkynyl, $C_{1-6}$ haloalkyl, halogen, cyano, —C(=Z)R°, —NR^fSO_2R°, —S(O)_mR°, CONR^iNHR° or $C_{1-10}$ alkyl wherein 2 or 3 nonadjacent carbon atoms in the alkyl chain can be replaced with —O—, —S— or —NR^f;
$R^2$ is hydrogen, $C_{1-6}$ alkyl, $C_{3-6}$ cycloalkyl, $C_{3-6}$ cycloalkyl-$C_{1-3}$ alkyl, $C_{1-3}$alkoxycarbonyl-$C_{1-3}$ alkyl, $C_{1-6}$ haloalkyl, or aralkyl;
$R^3$ is aryl or heteroaryl, each optionally substituted with one or more substituents independently selected from the group consisting of $C_{1-6}$ alkyl, $C_{1-6}$ alkoxy, $C_{1-6}$ alkylthio, $C_{1-6}$ alkylsulfonyl, aminosulfonyl, monoalkylaminosulfonyl, dialkylaminosulfonyl, halogen, haloalkyl, cyano, nitro, and —NR^{a''}R^{b''}, where R^{a''} and R^{b''} are each independently selected from the group consisting of hydrogen, $C_{1-9}$ alkyl, and $C_{1-9}$ alkylcarbonyl;

$R^f$ is hydrogen or $C_{1-10}$ alkyl;

$R^g$ is $C_{2-10}$ alkenyl;

$R^o$ is $C_{1-6}$ alkyl, $C_{2-6}$ alkenyl or; phenyl optionally substituted with one or more substituents independently selected from the group consisting of $C_{1-6}$ alkyl, haloalkyl, $C_{1-6}$ alkoxy, amino, alkylamino, dialkylamino, hydroxyalkyl, cyano, acylamino, alkylsulfonyl, alkylsulfonyloxy, and halogen;

$R^i$ is $R^o$, hydrogen, $C_{3-6}$ cycloalkyl or $C_{3-6}$ cycloalkyl-$C_{1-3}$ alkyl;

Z is O or $NOR^o$;

m is an integer from 0 to 2.

3. The compound of claim 1 wherein $R^1$ is $CHR^fR^g$, $C_{2-10}$ alkynyl, $C_{1-6}$ haloalkyl, or halogen; $R^2$ is hydrogen or $C_{1-6}$ alkyl; and $R^3$ is optionally substituted aryl.

4. The compound of claim 1 wherein $R^1$ is —$S(O)_mR^h$ or —$X^2C(\!\!=\!\!O)X^1R^f$, $X^2$ is $NR^{f1}$, $R^2$ is hydrogen or a $C_{1-6}$ alkyl, $R^3$ is optionally substituted aryl; and m is 2.

5. The compound of claim 1 wherein $R^1$ is $CHR^fR^g$, $R^g$ is $X^2C(\!\!=\!\!O)X^1R^f$, $R^2$ is hydrogen or a $C_{1-6}$ alkyl and $R^3$ is optionally substituted aryl.

* * * * *